United States Patent

Matsumoto et al.

[11] Patent Number: 6,064,477
[45] Date of Patent: *May 16, 2000

[54] METHOD OF AND APPARATUS FOR INSPECTING RETICLE FOR DEFECTS

[75] Inventors: Shunichi Matsumoto; Hiroaki Shishido, both of Yokohama, Japan

[73] Assignee: Hitachi, Ltd., Tokyo, Japan

[*] Notice: This patent is subject to a terminal disclaimer.

[21] Appl. No.: 08/644,740

[22] Filed: May 10, 1996

Related U.S. Application Data

[63] Continuation of application No. 08/192,036, Feb. 4, 1994, abandoned.

[30] Foreign Application Priority Data

Feb. 26, 1993 [JP] Japan ................................ 5-037816

[51] Int. Cl.$^7$ .................................................. G01N 21/88
[52] U.S. Cl. ................................... 356/237; 356/239
[58] Field of Search ......................... 356/239, 338, 356/445, 446, 336, 337, 394; 250/563, 572

[56] References Cited

U.S. PATENT DOCUMENTS

| | | | |
|---|---|---|---|
| 4,816,686 | 3/1989 | Hara et al. | 356/237 |
| 4,952,058 | 8/1990 | Noguchi et al. | 356/237 |
| 5,046,847 | 9/1991 | Nakata et al. | 356/338 |
| 5,098,191 | 3/1992 | Noguchi et al. | 356/239 |
| 5,225,886 | 7/1993 | Koizumi et al. | 356/338 |

FOREIGN PATENT DOCUMENTS

| | | |
|---|---|---|
| 56-132549 | 10/1981 | Japan . |
| 58-62543 | 4/1983 | Japan . |
| 59-65428 | 4/1984 | Japan . |
| 60-38827 | 2/1985 | Japan . |
| 60-154634 | 8/1985 | Japan . |
| 61-014659 | 5/1986 | Japan . |
| 61-104242 | 5/1986 | Japan . |
| 61-104244 | 5/1986 | Japan . |
| 60-154635 | 8/1986 | Japan . |
| 1-117024 | 5/1989 | Japan . |
| 1-153943 | 6/1989 | Japan . |
| 54-101390 | 8/1989 | Japan . |

*Primary Examiner*—Hoa Q. Pham
*Attorney, Agent, or Firm*—Antonelli, Terry, Stout & Kraus, LLP

[57] ABSTRACT

A reticle inspecting apparatus for inspecting a reticle for defects has a transparent of translucent substrate, a circuit pattern formed on the front surface of the substrate, and a phase shifter formed of a light-transmissive film on the front surface of the substrate. In the apparatus, a detection optical system is disposed so as not to gather directly reflected light and directly transmitted light and so as to gather scattered light and diffracted light which has been scattered and diffracted, respectively, by the reticle. This detection optical system enables separation of the gathered light by direction of illumination using detectors and spatial filters disposed respectively on Fourier transform planes to intercept light diffracted by straight edges of the circuit pattern, so as to form images of gathered light on the detectors. A signal processing system having a signal processing unit calculates defects on the basis of the output signals of the detectors and displays the calculated data on a display.

22 Claims, 35 Drawing Sheets

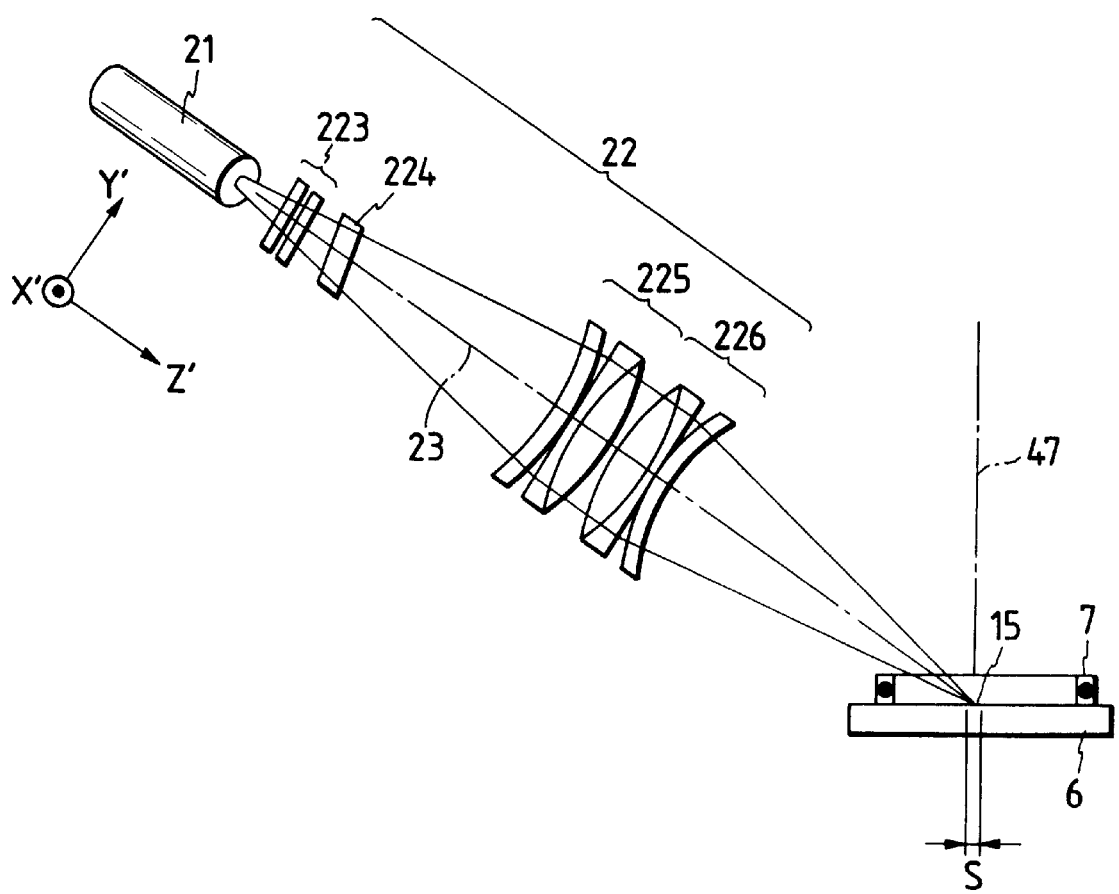

BACK ILLUMINATION MODE

FRONT ILLUMINATION MODE

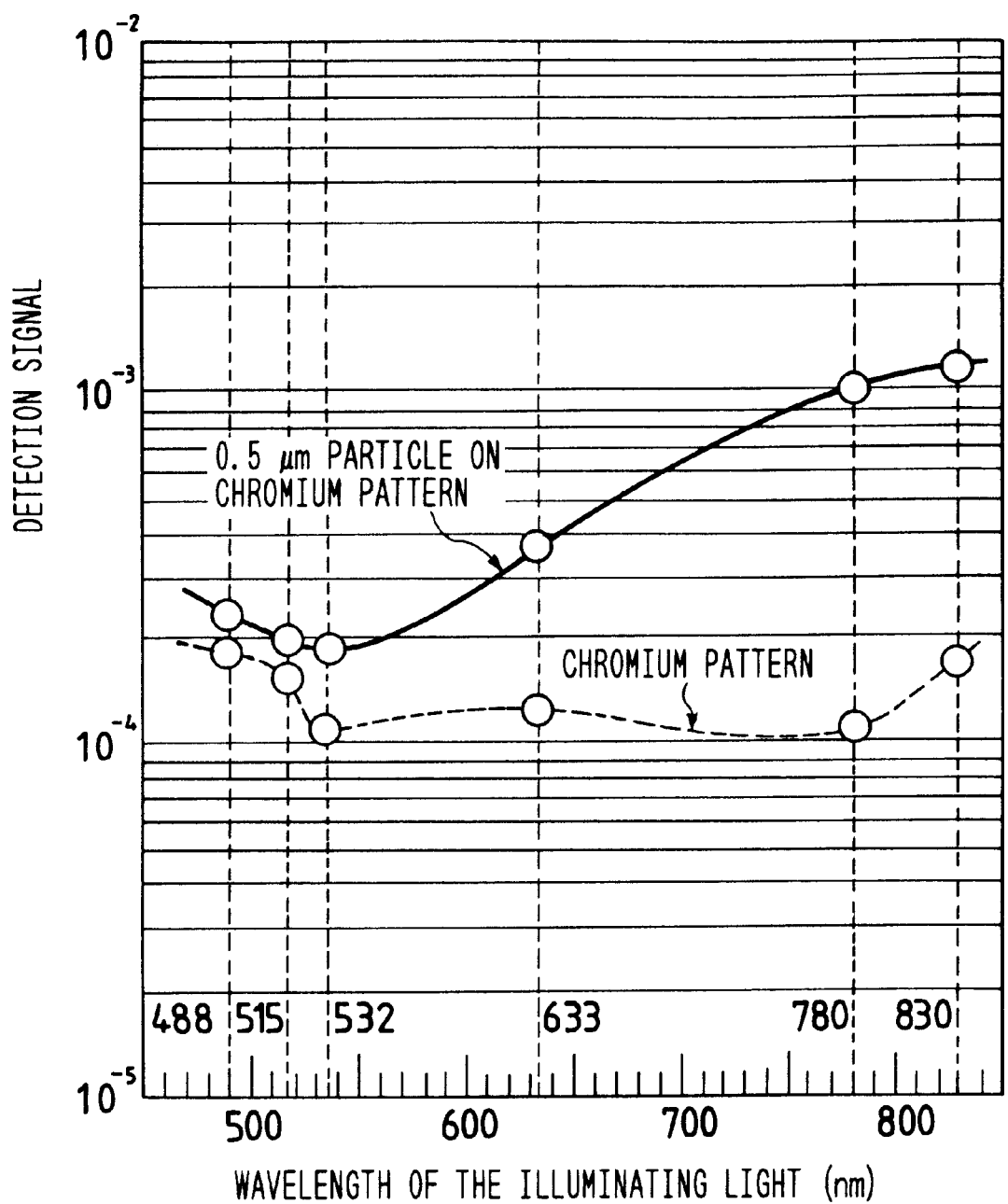

MEASURED RESULT OF SHADING

COMPENSATED DATA OF SHADING

DETECTED SIGNAL FROM A COMPENSATED DETECTOR

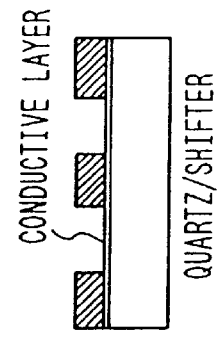
FIG. 42(A)
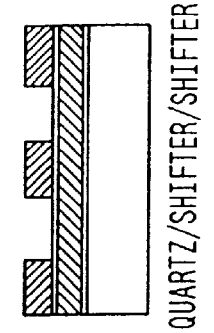
FIG. 42(B)
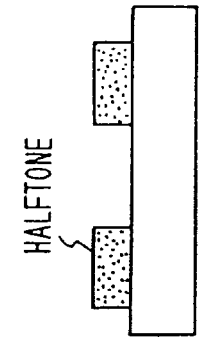
FIG. 42(C)
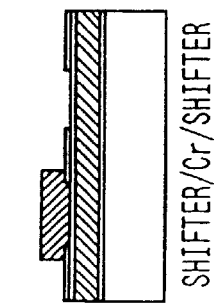
FIG. 42(D)
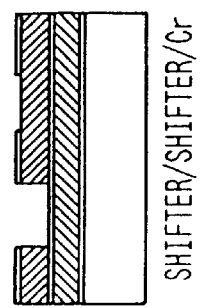
FIG. 42(E)
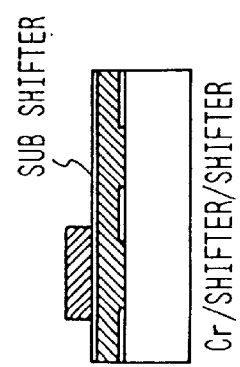
FIG. 42(F)
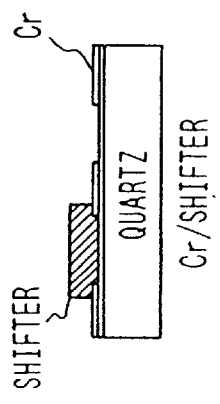
FIG. 42(G)
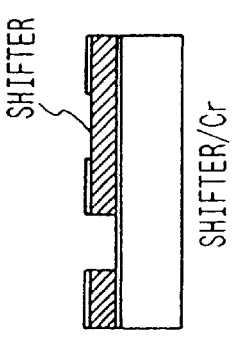
FIG. 42(H)
FIG. 42(I)

METHOD OF AND APPARATUS FOR INSPECTING RETICLE FOR DEFECTS

This application is a continuation of Ser. No. 08/192,036, filed Feb. 4, 1994, now abandoned.

BACKGROUND OF THE INVENTION

The present invention relates to a method of inspecting a reticle or a photomask (hereinafter referred to inclusively as a "reticle"), provided with a circuit pattern and a phase shifter formed of a light-transmissive film for defects, such as foreign particles adhering to the reticle; and, more particularly, to a method of inspecting a reticle provided with a phase shifter for defects, such as foreign particles, having sizes in the submicron range before printing the reticle on a wafer, and a reticle inspecting apparatus for carrying out the same reticle inspecting method.

When fabricating LSI chips or printed wiring boards, a reticle having a circuit pattern is inspected for defects before printing the reticle on wafers by a photographic process. If the reticle has minute foreign particles having sizes in the submicron range thereon, the reticle cannot be correctly printed on wafers; and, consequently, LSI chips fabricated by using such wafers become defective. Problems attributable to the minute foreign particles adhering to the reticle have become more and more significant with the recent progressive increase in the degree of integration of LSIs, and the existence of foreign particles even having sizes in the submicron range on the reticle is not permissible.

The inspection of the reticle for foreign particles before printing the reticle on a wafer is indispensable to prevent defective reticle printing, and various techniques for inspecting the reticle for foreign particles have been proposed. A prevalent method of inspecting a reticle for foreign particles, which is employed widely because of its capability of quick and highly sensitive inspection, irradiates the reticle obliquely with a light beam having a high directivity, such as a laser beam, and detects light scattered by foreign particles. However, since the light beam is diffracted at the edges of the pattern of the reticle, the diffracted light and the light scattered by foreign particles must be discriminated from each other. Various technical means for discriminating between the diffracted light and the scattered light have been proposed.

A first previously proposed technical approach is exemplified by an inspecting apparatus disclosed in, for example, Japanese Patent Laid-open (Kokai) No. 54-101390. This inspecting apparatus comprises a laser that emits a linearly polarized laser beam, an irradiating means for irradiating a circuit pattern obliquely with the linearly polarized laser beam so that the linearly polarized laser beam falls on the circuit pattern at a given incidence angle, and an oblique focusing optical system including a polarizing plate and lenses. When the circuit pattern is irradiated with the linearly polarized laser beam, the light diffracted by the circuit pattern and the light scattered by foreign particles differ from each other in the plane of polarization, i.e., the plane of vibration; therefore, the light scattered by the foreign particles can be discriminated and detected.

A second previously proposed technical approach is exemplified by an inspecting apparatus disclosed in, for example, Japanese Patent Laid-open (Kokai) No. 59-65428, 1-117024 or 1-153943. This inspecting apparatus comprises a scanning arrangment for scanning an object with a laser beam obliquely projected on the object, a first lens disposed above the object to condense scattered laser light so that the point of irradiation of the laser beam coincides substantially with the condensing point, a filter plate disposed on the Fourier transform image plane of the first lens to filter regular diffracted light diffracted by the circuit pattern of the object, a second lens for the inverse Fourier transform of the light scattered by the foreign particles and transmitted through the screen plate, a slit plate disposed at the focal point of the second lens to screen scattered light from portions of the object other than a portion corresponding to the point of irradiation with the laser beam, and a light receiving device for receiving the light scattered by the foreign particles and which passes through the slit of the slit plate. This inspecting apparatus operates on the basis that, generally, the elements of a circuit pattern are extended in a single direction or in several directions, so that the diffracted light diffracted by the elements of the circuit pattern extending in a specified direction can be filtered by a spatial filter disposed on the Fourier transform image plane, making it possible to detect only the light scattered by the foreign particles.

A third previously proposed technical approach is exemplified by an arrangement disclosed in, for example, Japanese Patent Laid-open (Kokai) No. 58-62543. This arrangement operates on the basis that light diffracted by the edges of a circuit pattern is directional light, while light scattered by foreign particles is not directional and identifies foreign particles on the basis of the logical product of the outputs of a plurality of obliquely arranged detectors.

A fourth previously proposed technical approach is exemplified by an arrangement disclosed in, for example, Japanese Patent Laid-open (Kokai) No. 60-154634 or 60-154635. This arrangement is based on the fact that light diffracted by the edges of a circuit pattern converges only along a specific direction, while light scattered by foreign particles is scattered in all directions and identifies foreign particles from the outputs of a plurality of detectors.

Apparatuses and methods relating to the inspection of objects for minute foreign particles, such as a schlieren method, a phase-contrast microscope and a technique relating to a diffraction image having a finite size are disclosed in, for example, Hiroshi Kubota, "Oyou Kogaku", Iwanami Zensho, pp. 129–136.

In an array type detector, such as a one-dimensional solid-state imaging device provided with an array of solid-state image sensors, an output signal representing a foreign particle is distributed to a plurality of pixels if the foreign particle corresponds to a plurality of elements of the detector; and, consequently, the output of the detector is reduced, and therefore, there is the possibility that the detector fails in detecting the foreign particle. An invention made to obviate such a possibility, disclosed in Japanese Patent Laid-open (Kokai) No. 61-104242, disposes an array type detector at an angle to the direction of the scanning of an inspection table.

Other inventions made for the same purpose, disclosed in Japanese Patent Laid-open (Kokai) Nos. 61-104244 and 61104659, employ an array type detector having a unique shape and provided with elements arranged in a unique arrangement.

Irregular illumination and the variation of illumination adversely affects the repeatability and accuracy of detection. An invention disclosed in Japanese Patent Laid-open (Kokai) No. 60-038827 calibrates the intensity of scattered light automatically by using a standard sample having known characteristics.

Japanese Patent laid-open (Kokai) No. 56-132549 discloses a n invention for obviating th e misidentifying of a large amount of light scattered by a comparatively large foreign particle as light scattered by a plurality of comparatively small foreign particles.

As mentioned above, failure in finding foreign particles which adversely affect the quality of LSI chips has become a significant problem with the reduction of the size of foreign particles to be detected. The first previously proposed technical approach, for example, the invention disclosed in Japanese Patent Laid-open (Kokai) No. 54-101390, is unable to detect minute foreign particles because the difference between the plane of polarization of the light scattered by minute foreign particles and the plane of polarization of the light diffracted by the edges of the circuit pattern is small.

The second previously proposed technical approach, for example, the inventions disclosed in Japanese Patent Laid-open (Kokai) Nos. 59-65428, 1-117024 and 1153943, detect only the light scattered by foreign particles by separating the light scattered by foreign particles from the light diffracted by the circuit pattern with the filter plate and the slit plate. Although these inventions use a detecting mechanism for detecting foreign particles by a simple binary method having a simple configuration to their advantage, the light diffracted by the intersection of the elements of the circuit pat tern does not travel unidirectionally like the light diffracted by the straight edge of the circuit pattern, and hence, the spatial filter is unable to filter the light diffracted by the intersection of the elements of the circuit pattern perfectly. Furthermore, since the light diffracted by a minute circuit pattern having a size in the micron range for a LSI having a very high degree of integration is analogous in behavior to the light scattered by foreign particles, it is practically difficult to discriminate between the circuit pattern and foreign particles by a simple binary method.

The apparatus proposed as the third previously proposed technical arrangement in, for example, Japanese Patent Laid-open (Kokai) No. 58-62543 and those proposed as the fourth previously proposed technical arrangement in, for example, Japanese Patent Laid-open (Kokai) Nos. 60-154634 and 60-154635 have difficulty in employing an optical system having a sufficiently high condensing ability because of their configurations; and hence, it is practically difficult for these apparatuses to detect faint light scattered by foreign particles.

The apparatuses disclosed as the fifth previously proposed technical arrangement in, for example, Japanese Patent Laid-open (Kokai) Nos. 61-104242 and 61-104244 requires a special detector and a special optical system, which are costly.

The apparatus disclosed as the sixth previously proposed technical arrangement in, for example, Japanese Patent Laid-open (Kokai) No. 60-038827 has drawbacks in application to an array type detector suitable for quick detection and in structural accuracy for detecting minute foreign particles.

The apparatus disclosed as the seventh previously proposed technical arrangement in, for example, Japanese Patent Laid-open (Kokai) No. 56-132544 detects only a single point on a large foreign particle; and hence, the apparatus is unable to recognize the shape of an elongate foreign particle accurately.

A reticle recently developed to improve resolution in transferring a circuit pattern formed on the reticle is provided with a transparent or translucent thin film, which is called a phase shift film or a phase shifter, having a thickness equal to an odd number of times half the wavelength of the light used for exposure and formed so as to cover spaces between the elements of the circuit pattern. Although this thin film is transparent or translucent, the thickness of this thin film is several times the thickness (on the order of 0.1 $\mu$m) of the circuit pattern. Consequently, the intensity of the light diffracted by the edges of the thin film is several to several tens of times the intensity of the light diffracted by the edges of the circuit pattern, thus reducing the foreign particle detecting sensitivity significantly.

SUMMARY OF THE INVENTION

Accordingly, it is an object of the present invention to provide a method of inspecting a reticle, such as a reticle fabricated by forming a circuit pattern and a phase shift film for improving the transfer resolution on a transparent or translucent substrate for defects, such as minute foreign particles having sizes in the submicron range adhering to the circuit pattern, which reticle is capable of separating the defects from the circuit pattern and of stably detecting the defects, and an apparatus for carrying out the method.

A reticle inspecting apparatus in a first aspect of the present invention for inspecting a reticle, such as a photomask, fabricated by forming a circuit pattern on a substrate, for defects, such as foreign particles adhering to the substrate, comprises: an inspection stage for supporting the reticle, capable of optionally moving in directions along an X-axis, a Y-axis and a Z-axis; a first illuminating unit having first and second light sources disposed opposite to each other on the side of the front surface of the reticle so as to project beams of light of about 780 nm in wavelength obliquely on the circuit pattern formed on the front surface of the reticle supported on the inspection stage; a second illuminating unit having third and fourth light sources disposed opposite to each other on the side of the back surface of the reticle so as to project beams of light of about 488 nm in wavelength obliquely on the circuit pattern through the substrate of the reticle supported on the inspection stage; a focusing optical system having a high NA (numerical aperture) of 0.4 or above, disposed on the side of the front surface of the substrate so as not to gather directly reflected light and directly transmitted light and so as to gather only light scattered by a portion of the circuit pattern and light diffracted by the same portion of the circuit pattern, capable of separating the gathered light by direction and wavelength, provided with spatial filters disposed respectively on Fourier transform image planes to filter the light diffracted by the straight portions of the circuit pattern and detectors, and capable of forming images on the detectors; and a signal processing system having a signal processing unit which calculates data concerning defects in the circuit pattern on the basis of the respective outputs of the detectors and the output of a binary circuit set for a threshold and which displays the results of calculation.

A reticle inspecting method in accordance with the present invention inspects a reticle, fabricated by forming a circuit pattern of an opaque or light-transmissive film on a substrate, for defects in the reticle by using the foregoing reticle inspecting apparatus in the first aspect of the present invention.

A reticle inspecting apparatus in a second aspect of the present invention for inspecting a reticle, fabricated by forming a pattern of an opaque or light-transmissive film on a transparent or translucent substrate, for defects, such as foreign particles adhering to the substrate, comprises: an inspection stage unit comprising an inspection stage for supporting the reticle, capable of optionally moving in directions along an X-axis, a Y-axis and a Z-axis, and a stage control system for controlling the movement of the inspection stage; an illuminating unit for the transmitted illumination and reflected illumination of the pattern; a detection optical system disposed so as not to gather directly reflected light and directly transmitted light and so as to gather only scattered light and diffracted light which has been scattered and diffracted, respectively, by the substrate, and provided with spatial filters disposed respectively on Fourier transform image planes to filter light diffracted by straight portions of the pattern and detectors on which the scattered light and the diffracted light are focused; and a signal processing system which calculates the defect data of the defects on the substrate on the basis of the outputs of the detectors and which displays the results of calculation.

A reticle inspecting method in accordance with the present invention inspects a reticle, fabricated by forming a pattern of an opaque or light-transmissive film on a transparent or translucent substrate, for defects in the reticle by using the foregoing reticle inspecting apparatus in the second aspect of the present invention.

A reticle inspecting apparatus in a third aspect of the present invention for inspecting a reticle, fabricated by forming a pattern of an opaque or light transmissive film on a transparent of translucent substrate, for defects, such as foreign particles adhering to the substrate, comprises: an inspection stage unit including an inspection stage for supporting the reticle, capable of optionally moving in directions along an X-axis, a Y-axis and a Z-axis, and a stage control system for controlling the movement of the inspection stage; an illuminating unit which projects a beam of light of about 780 nm in wavelength obliquely on the pattern from the side of the front surface of the reticle and projects a beam of light of about 488 nm in wavelength obliquely on the pattern through the substrate from the side of the back surface of the substrate; a detection optical system disposed so as not to gather directly reflected light and directly transmitted light and so as to gather only scattered light and diffracted light which has been scattered and diffracted, respectively, by the substrate, capable of separating the gathered light by direction and wavelength, provided with spatial filters disposed respectively on Fourier transform image planes to filter light diffracted by straight portions of the pattern and detectors, and capable of forming images on the detectors; and a signal processing system, capable of calculating the data of defects on the substrate on the basis of the detectors and of displaying the results of calculation.

A reticle inspecting method in accordance with the present invention inspects a reticle, fabricated by forming a pattern of an opaque or light-transmissive film on a transparent or translucent substrate, for defects in the reticle by using the foregoing reticle inspecting apparatus in the third aspect of the present invention.

A reticle inspecting apparatus in a fourth aspect of the present invention for inspecting a reticle, fabricated by forming a pattern of an opaque or light-transmissive film on a transparent or translucent substrate, for defects, such as foreign particles adhering to the substrate, comprises: an inspection stage unit including an inspection stage for supporting the reticle, capable of optionally moving in directions along an X-axis, a Y-axis and a Z-axis, and a stage control system for controlling the movement of the inspection stage; a first illuminating unit disposed on the side of the front surface of the substrate so as to project a beam of light of about 780 nm in wavelength obliquely on the pattern formed on the front surface of the substrate; a detection optical system disposed on the side of the front surface of the substrate so as not to gather directly reflected light and so as to gather scattered light and diffracted light which has been scattered and diffracted, respectively, by the substrate, provided with spatial filters disposed on Fourier transform image planes to filter the light diffracted by a straight portion of the pattern and detectors, and capable of forming images on the detectors; a second illuminating unit disposed on the side of the back surface of the substrate so as to project a beam of light of about 488 nm in wavelength obliquely on the pattern through the substrate; and a signal processing system capable of calculating data concerning the defects on the substrate on the basis of the outputs of the detectors and of displaying the results of calculation.

A reticle inspecting method in accordance with the present invention inspects a reticle, fabricated by forming a pattern of opaque or light-transmissive film formed on a transparent or translucent substrate, for defects in the reticle by using the foregoing reticle inspecting apparatus in the fourth aspect of the present invention.

A reticle inspecting apparatus in a fifth aspect of the present invention for inspecting a reticle, fabricated by forming a pattern of an opaque or light-transmissive film on a transparent or translucent substrate, for defects, such as foreign particles adhering to the substrate, comprises: an inspection stage unit including an inspection stage for supporting the reticle, capable of optionally moving in directions along an X-axis, a Y-axis and a Z-axis, and a stage control system for controlling the movement of the inspection stage; an illuminating unit for the reflected illumination of the pattern with a beam of light having a wavelength of about 1.6 d, where d is the size of the smallest defects among those to be detected, and for the transmitted illumination of the pattern with a beam of light having a wavelength of 1.0 d; a detection optical system disposed so as not to gather directly reflected light and directly transmitted light and so as to gather scattered light and diffracted light which has been scattered and diffracted, respectively, by the substrate, capable of separating the gathered light by direction, provided with spatial filters for filtering the light diffracted by a straight portion of the pattern and detectors, and capable of forming images on the detectors; and a signal processing system capable of calculating the data of the defects on the substrate on the basis of the outputs of the detectors and of displaying the results of calculation.

A reticle inspecting method in accordance with the present invention inspects a reticle, fabricated by forming a pattern of an opaque or light-transmissive film on a transparent or translucent substrate, for defects in the reticle by using the foregoing reticle inspecting apparatus in the fifth aspect of the present invention.

A reticle inspecting apparatus in a sixth aspect of the present invention for inspecting a reticle, fabricated by forming a pattern of an opaque or light-transmissive film on a transparent or translucent substrate, for defects, such as foreign particles adhering to the substrate, comprises: an inspection stage unit including an inspection stage for supporting the reticle, capable of optionally moving in directions along an X-axis, a Y-axis and a Z-axis, and a stage control system for controlling the movement of the inspection stage; an illuminating unit for obliquely illuminating the pattern from the side of the front surface of the substrate with a single beam of light having a wavelength in the range of 600 nm to 800 nm, or a plurality of beams of light having different wavelengths in the range of 600 nm to 800 nm, and for obliquely illuminating the pattern through the substrate from the side of the back surface of the substrate with a single beam of light having a wavelength in the range of 450 nm to 550 nm, or a plurality of beams of light having different wavelengths in the range of 450 nm to 550 nm; a detection optical system disposed on the side of the front surface of the substrate so as not to gather directly reflected light and directly transmitted light and so as to gather scattered light and diffracted light which has been scattered and diffracted, respectively, by the substrate, capable of separating the gathered light by direction and wavelength, provided with spatial filters disposed on Fourier transform image planes to filter the light diffracted by straight portions of the pattern and detectors, and capable of forming images on the detectors; and a signal processing system, capable of calculating the data of the defects on the substrate on the basis of the outputs of the detectors and of displaying the results of calculation.

A reticle inspecting method in accordance with the present invention inspects a reticle, fabricated by forming a pattern of an opaque or light-transmissive film on a transparent or translucent substrate, for defects in the reticle by using the reticle inspecting apparatus in the sixth aspect of the present invention.

A reticle inspecting apparatus in a seventh aspect of the present invention for inspecting a reticle, fabricated by forming a pattern of an opaque or light-transmissive film on a substrate, for defects, such as foreign particles adhering to the substrate, comprises: an inspection stage unit including an inspection stage for supporting the reticle, capable of optionally moving in directions along an X-axis, Y-axis and a Z-axis, and a stage control system for controlling the movement of the inspection stage; a first illuminating unit for obliquely illuminating the pattern formed on the front surface of the substrate with a beam of light having a wavelength in the range of 600 nm to 800 nm, or a plurality of beams of light having different wavelengths in the range of 600 nm to 800 nm; a first detection optical system disposed on the side of the front surface of the substrate so as not to gather directly reflected light and so as to gather scattered light and diffracted light which has been scattered and diffracted, respectively, by the substrate, provided with spatial filters for filtering the light diffracted by straight portions of the pattern, and capable of forming images; a second illuminating unit for obliquely illuminating the pattern through the substrate from the side of the back surface of the substrate with a beam of light having a wavelength in the range of 450 nm to 550 nm, or a plurality of beams of light having different wavelengths in the range of 450 nm to 550 nm; a second detection optical system disposed on the side of the back surface of the substrate so as not to gather directly transmitted light and so as to gather scattered light and diffracted light which has been scattered and diffracted, respectively, by the substrate, provided with spatial filters disposed on Fourier transform image planes to filter the light diffracted by straight portions of the pattern and detectors, and capable of forming images on the detectors; and a signal processing system capable of calculating the data of defects on the basis of the outputs of the detectors and of displaying the results of calculation.

A reticle inspecting method in accordance with the present invention inspects a reticle, fabricated by forming a pattern of an opaque or light-transmissive film on a transparent or translucent substrate, by using the foregoing reticle inspecting apparatus in the seventh aspect of the present invention.

A substrate inspecting apparatus in an eighth aspect of the present invention for inspecting a transparent or translucent substrate for defects, such as foreign particles adhering to light-transmissive portions of the substrate, comprises: an inspection stage unit including a movable inspection stage for supporting the substrate, and a stage control system for controlling the movement of the inspection stage; an illuminating unit for effecting illumination of the substrate with a beam of light having a wavelength of 488 nm; a detection optical system disposed so as not to gather directly transmitted light, and provided with detectors for receiving scattered light and diffracted light which has been scattered and diffracted, respectively, by the substrate; and a signal processing system capable of calculating data concerning the defects on the substrate on the basis of the outputs of the detectors and of displaying the results of calculation.

A substrate inspecting method in accordance with the present invention inspects a substrate for defects in the substrate by using the substrate inspective apparatus in the eighth aspect of the present invention.

A substrate inspecting apparatus in an ninth aspect of the present invention for inspecting a transparent or translucent substrate for defects, such as foreign particles adhering to light-transmissive portions of the substrate, comprises: a movable inspection stage for supporting the substrate, and a stage control system for controlling the movement of the inspection stage; an illuminating unit for effecting illumination of the substrate with a beam of light having a wavelength of 1.0 d, where d is the size of the smallest defects among those to be detected, a detection optical system disposed so as not to gather directly transmitted light and so as to gather scattered light and diffracted light which has been scattered and diffracted, respectively, by the substrate, and provided with detectors for receiving the scattered light and the diffracted light; and a signal processing system capable of calculating data concerning the defects on the basis of the outputs of the detectors and of displaying the results of calculation.

A substrate inspecting method in accordance with the present invention inspects transparent or translucent substrates for defects by using the foregoing substrate inspecting apparatus in the ninth aspect of the present invention.

A substrate inspecting apparatus in a tenth aspect of the present invention for inspecting transparent or translucent substrate for defects, such as foreign particles adhering to light-transmissive portions of the substrate, comprises: an inspection stage unit including a movable inspection stage for supporting the substrate, and a stage control system for controlling the movement of the inspection stage; an illuminating unit for effecting illumination of the substrate with a beam of light having a wavelength in the range of 450 nm to 550 nm, or a plurality of beams of light having different wavelengths in the range of 450 nm to 550 nm; a detection optical system disposed so as not to gather directly transmitted light and so as to gather scattered light and diffracted light which has been scattered and diffracted, respectively, by the substrate and provided with detectors for receiving the gathered scattered light and diffracted light; and a signal processing system capable of calculating data concerning the defects on the basis of the outputs of the detectors and of displaying the results of calculation.

A substrate inspecting method in accordance with the present invention for inspecting a transparent or translucent substrate for defects inspects the substrate for defects by using the foregoing substrate inspecting apparatus in the tenth aspect of the present invention.

BRIEF DESCRIPTION OF THE DRAWINGS

The above and other objects, features and advantages of the present invention will become more apparent from the following description taken in connection with the accompanying drawings, in which:

FIG. 3 is a diagrammatic view of one of the symmetrically disposed illuminating units included in the reticle inspecting apparatus of FIG. 1;

FIGS. 19-1 and 19-2 are diagrammatic views for assistance in explaining the configuration of a reticle inspecting apparatus in accordance with the present invention and scattered light components which can be detected by the same reticle inspecting apparatus;

FIG. 20 is a graph showing the respective variations of detection signals provided when a 0.5 $\mu$m particle on the chromium pattern is detected and when the chromium pattern is detected, respectively, in the front illumination mode with the wavelength of the illuminating light beam;

FIGS. 42A to 42I are sectional views of various reticles with a phase shifter to be inspected by the reticle inspecting apparatus in accordance with the present invention.

DETAILED DESCRIPTION OF THE PREFERRED EMBODIMENTS

The present invention relates to U.S. patent application Ser. No. 07/902,819 and Korean patent application No. 11092/1992.

Prior to a discussion of the preferred embodiments, operations of the characteristics of the present invention will be described.

According to certain technical literature, for example, Wolf, "Principle of optics", pp. 647 to 664, when small particles are almost equal to the wave length of illumination light in size, scattered light from foreign particles is not uniform, but is distributed sharply.

The present invention is based on the fact that the aforementioned increasing problem of missing foreign particles is caused by a distribution of scattered light from those small particles.

This is because not only has no consideration been given to the numerical aperture (NA) of the detection optical system, but also, it has been considered that foreign particles can be detected even if the detection optical system cannot resolve them. Since scattered light from small particles has an irregular directivity, mentioned in the above literature, however, they may not be detected by a detection optical system with a small numerical aperture. Therefore, it is believed that this has resulted in a missing of the foreign particles.

The ideology of the present invention shows that a detection optical system having the resolution of the prior art may detect small foreign particles, but cannot detect them stably. Also, it has been ascertained that to accomplish a target for "detection of foreign particles", a resolution for resolving the size of foreign particles to be detected is necessary. The process of investigation will be described hereunder.

The physics of light scattering is extremely complicated. The simplest problem in which a plane wave is irradiated onto a single ball floating in the air was analyzed first by Gustav Mie in 1908.

The solution, which is known as a Mie's theory, is a summing up series of a mathematical function which is called spherical harmonics. It will not be referred to here because it is outside the subject of the present invention.

Figure 11:
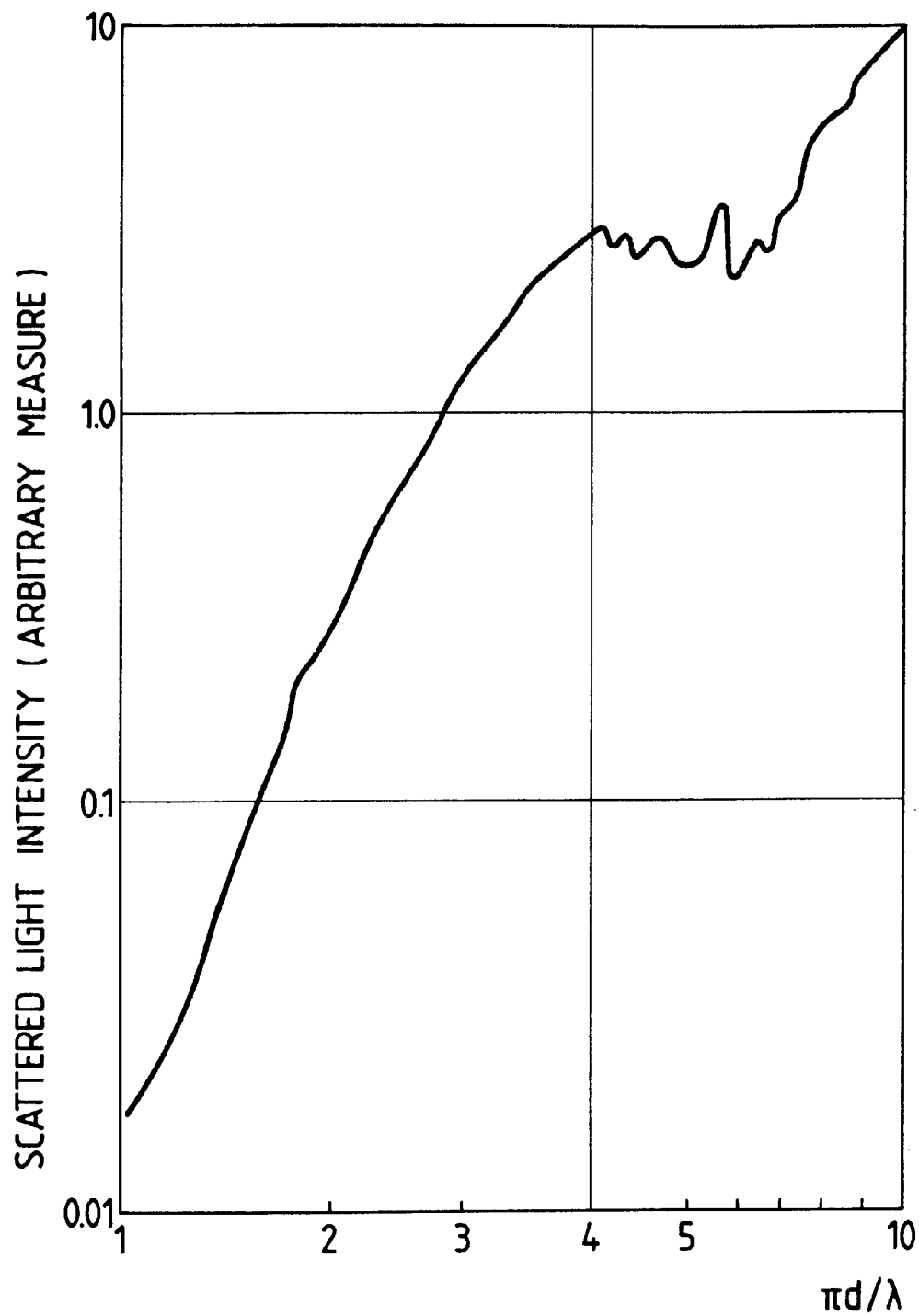
FIG. 11 is a graph showing the relation between the theoretical intensity of light scattered by particles and a nondimensional value $\pi d/1$, where d is the size of the particle and $\lambda$ is the wavelength of the illuminating light beam.

A particle, such as a latex ball, scatters the light of an incident beam by a combination of processes of reflection, refraction, absorption, and diffraction. FIG. 11 shows the intensity of scattered light from ball like foreign particles.

FIG. 11 expresses the theoretical value of scattered light intensity from the foreign particles by a dimensionless number $\pi D/\lambda$ using a wave length of $\lambda$ of a laser beam and a foreign particle diameter of D, and the theoretical value of Mie scattering is modified to that of a particle adhered onto a substrate as an application example of the present invention.

The horizontal axis indicates a dimensionless number using a wave length of $\lambda$ of the detected light (for example, 550 nm) and a detected foreign particle diameter of d.

The area wherein the value of $\pi d/\lambda$ is less than about 4 (foreign particles smaller than d=0.7 $\mu$m when $\lambda$=550 nm) is called particularly a Rayleigh scattering area, and the scattered light from foreign particles suddenly decreases in inverse proportion to the diameter to the 6th power. Therefore, detection of foreign particles in this area requires great attention to the detector sensitivity.

In the area wherein the value of $\pi d/\lambda$ is larger than about 4, the light scatters with a directivity according to a diffraction theory.

Figure 12:
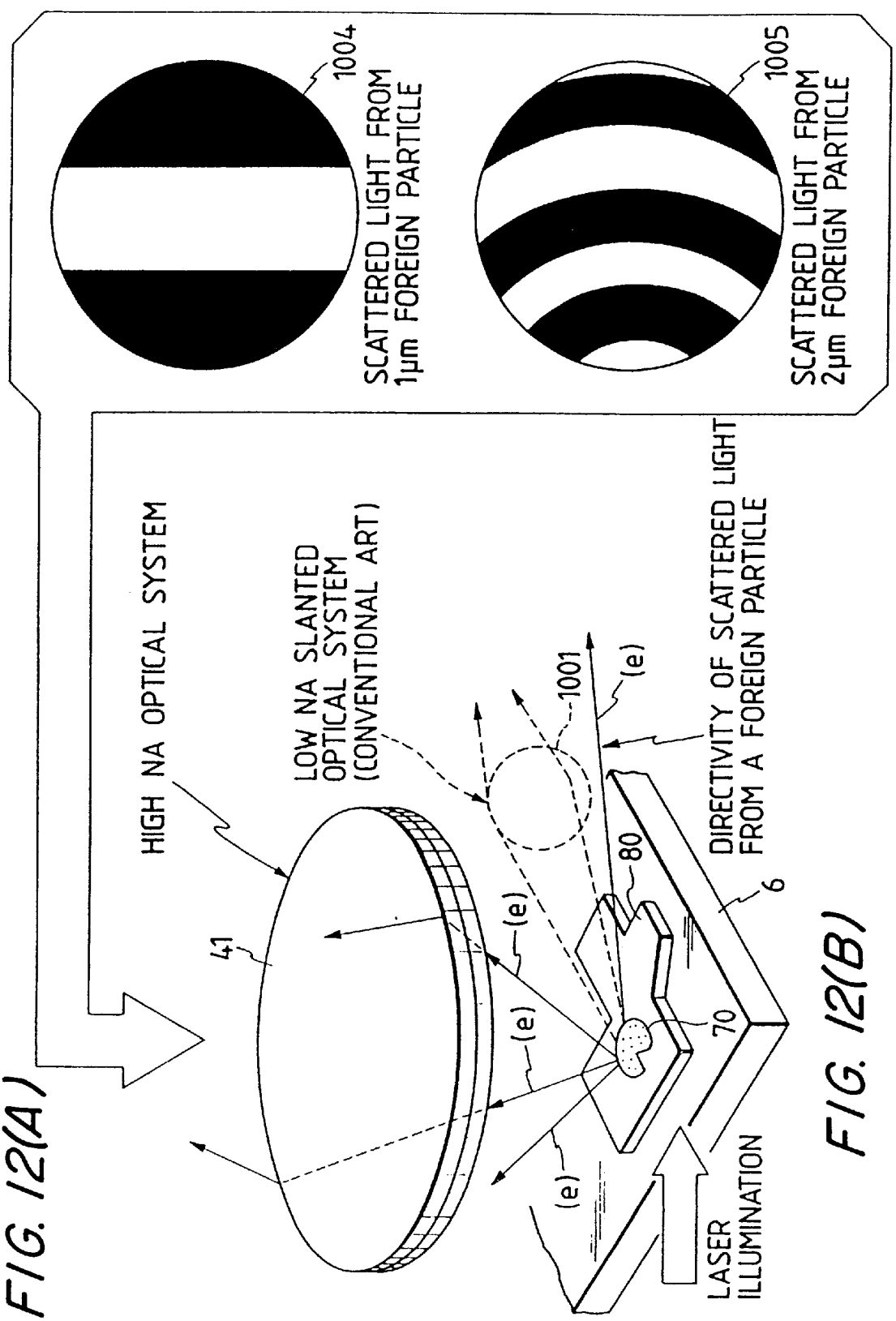
FIGS. 12(A) and 12(B) are views for assistance in explaining a method of detecting scattered light from a foreign particle by using an optical system having a high NA in accordance with the present invention.

The situation is shown in FIG. 12(A).

FIG. 12(B) is a schematic diagram showing that scattered light from foreign particles may be detected by using a high NA optical system according to the present invention. Since the scattered light from the foreign particles has a distribution, it is necessary to determine the numerical aperture (NA) of the detector in consideration of the scattered light distribution when detecting foreign particles in this area.

Figure 13:
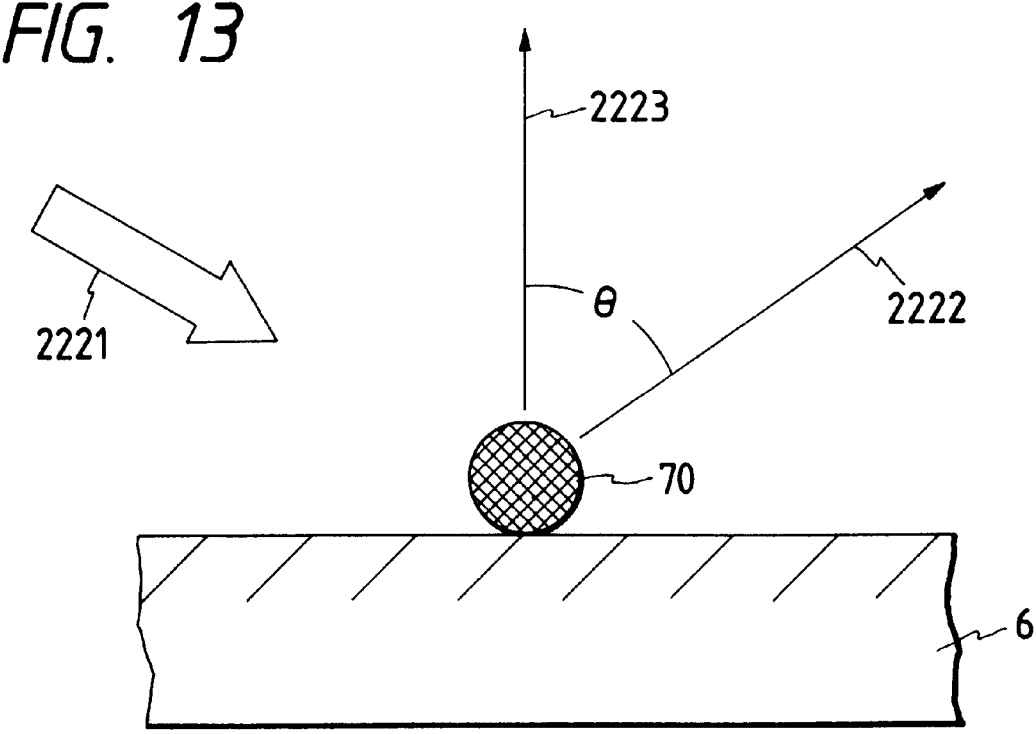
FIG. 13 is a diagrammatic view showing the direction of travel of light diffracted by a foreign particle.

FIG. 13 shows the direction of diffracted light when a laser beam 2221 is irradiated onto a foreign particle 70 on a recticle 6. The diffracted light is followed by 0-dimensional diffracted light 2222, dimensional diffracted light 2223, 2-dimensional diffracted light at an angle of $\theta$, - - - .

The 0-dimensional diffracted light 2222 is a positive reflected light of the laser beam 2221, and so detection of scattered light from foreign particles refers to detection of one-dimensional or higher-dimensional diffracted light.

The above angle $\theta$ is obtained from the diffracted light equation:

$$d_0 \cdot \sin \theta = \lambda$$

wherein, $d_0$ is defined variously, such as diameter, width, length, or mean value of diameter. The following argument is held regardless of the value of d0.

Therefore, any of the above definitions will not affect the result.

Therefore, it is assumed here that $d_0=d$ or $d_0$ indicates a foreign particle diameter.

The necessary numerical aperture (NA) of the detection optical system is obtained under the most severe condition $\pi d/\lambda=4$.

$\pi \cdot d/\lambda=4$ $d/\lambda=1.27$ $\lambda/d=0.79$

From $\sin \theta = \lambda/d$:

$$\theta = \sin^{-1} (0.79)$$
$$= 52°$$

This means that the maximum gap of diffracted light is 52°. When a detection optical system with an aperture of more than 52° is used, therefore, at lowest one-dimensional diffracted light can be detected, resulting in no missing of foreign particles.

Figure 14:
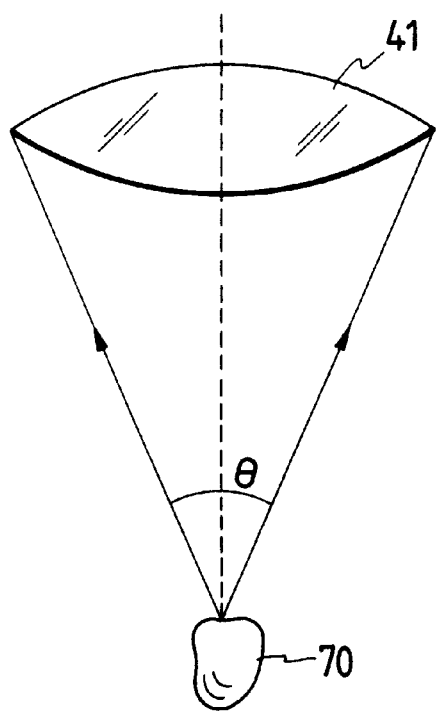
FIG. 14 is a diagrammatic view for assistance in explaining the definition of the NA of an optical system in accordance with the present invention.

FIG. 14 is a schematic view showing the definition of the numerical aperture (NA) of an optical system.

In FIG. 14, the numerical aperture (NA) of an object lens 41 of the detector system is obtained from NA=sin ($\theta$/2) (n: a refractive index of the optical path, n=1 in the air). NA=1·sin (52°/2)=0.44.

Therefore, scattered light from foreign particles can be detected without missing the particles by a detector system having NA larger than about 0.44.

In this case, as the NA increases, the detection capability also increases and foreign particles in the Rayleigh area can be detected more conveniently. When NA is close to 0.4, even if it is less than 0.44 inversely, foreign particles can be detected practically because diffracted light has a certain width. When NA is more than 0.5 inversely, scattered light from the circuit pattern enters into the detector system for a reason which will be described later, and the request for detecting only scattered light from foreign particles is turned down, causing a reduction in advantages of increasing NA especially. Therefore, NA ranging from 0.4 to 0.6 or so is practically suited.

Next, detection of foreign particles in the Rayleigh area will be described.

As mentioned above, a detection optical system having the resolution of the prior art may detect small foreign particles, but cannot detect them stably. To accomplish a target of "detection of foreign particles", a resolution for resolving the size of foreign particles to be detected or so is necessary.

The present invention has a detection optical system having the numerical aperture (NA) for resolving foreign particles to be detected. Concretely, NA is calculated from Equation (1) indicated below.

$$d=0.6 \ (\lambda/NA) \tag{1}$$

An optical system having a value close to this NA is desirable. In the above equation, the symbol d indicates the size of foreign particles to be detected, $\lambda$ the wave length of the illumination light, and NA the numerical aperture. When NA of the detector system cannot be set so as to satisfy Equation (1), it is necessary to shorten $\lambda$ of the illumination system so as to satisfy the equation (1).

In a conventional detection optical system for foreign particle inspection, it is not considered that the resolution for resolving foreign particles is necessary. The present invention is based on a new concept that a detection optical system for resolving foreign particles as shown in Equation (1) is necessary.

However, the coefficient of Equation (1) is not required to be as large as the value for calculating the general resolution, such as 0.6. The experiment conducted by the inventor for the present invention shows that when NA ranges from 0.24 to 0.6, the required foreign particle detecting precision is obtained.

Figure 15:
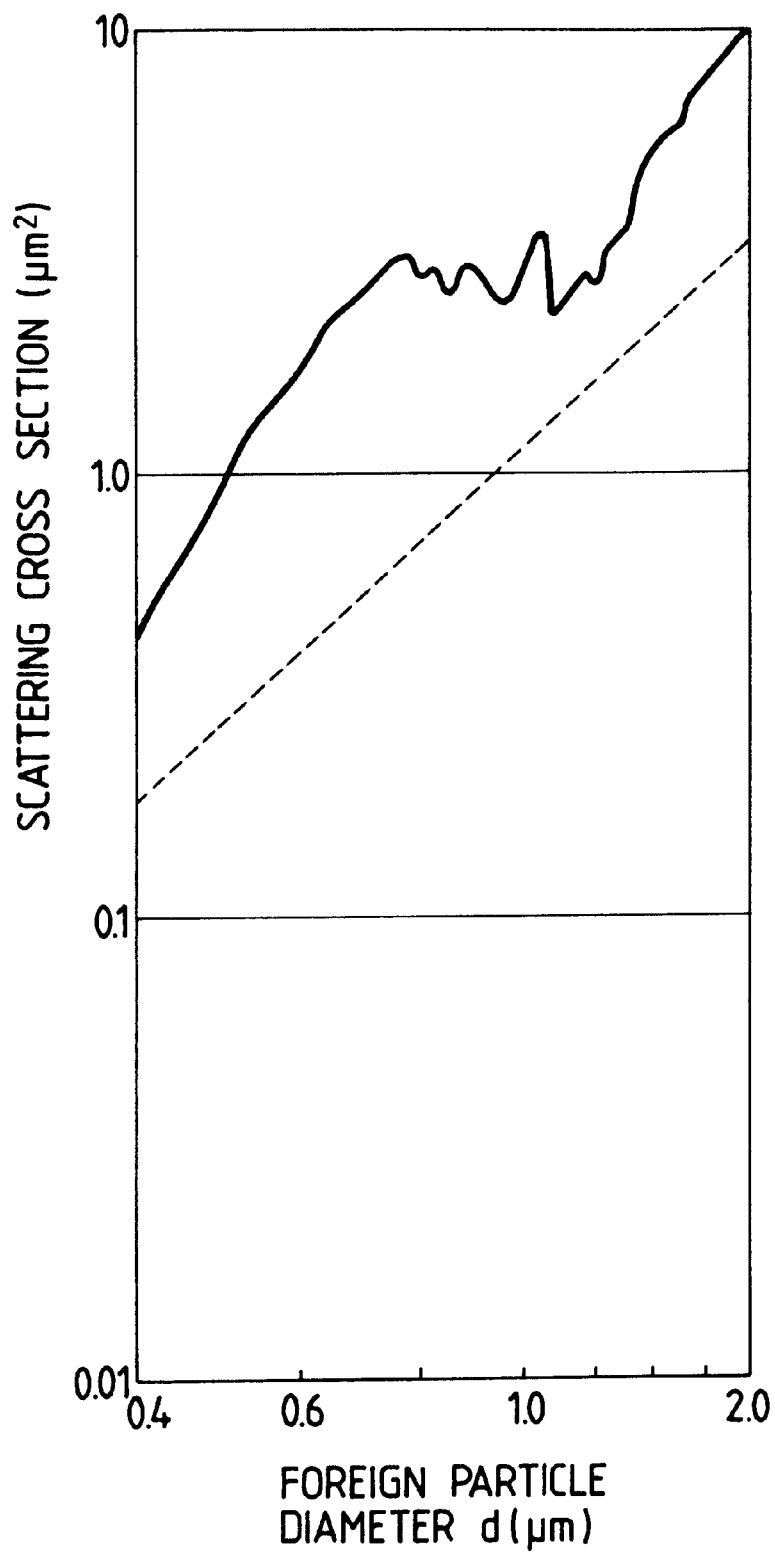
FIG. 15 is a graph showing the relation between the sectional area of scattered light proportional to the intensity of the light scattered by a foreign particle and the diameter d of the foreign particle.

FIG. 15 is a chart showing the scattering cross section, which is proportional to the scattered light intensity from foreign particles, vs the foreign particle diameter.

In FIG. 15, the horizontal axis represents the foreign particle diameter and the vertical axis represents the scattering cross section. This scattering cross section is in proportion to the scattered light generated from foreign particles and can be obtained from Mie's scattering theory. The interpretation means that, when generated scattered light is observed, it is observed as if it were scattered light generated from the foreign particles shown by the solid line in the drawing. The drawing also shows the geometrical cross section using a dashed line. The drawing shows that when a foreign particle is observed using scattered light, the observed foreign particle size is larger than the actual size. (That is just the reason why foreign particles are inspected by scattered light.) FIG. 15 shows that the ratio is 3 to 6 times or so in area ratio and hence $\sqrt{3}$ to $\sqrt{7}$ times in diameter.

In this case, Equation (1)' is expressed by thie equation.

$$\begin{aligned} d &= (.06/\sqrt{3} \ \text{to} \ \sqrt{6} \cdot (\lambda/NA) \\ &= (0.24 \ \text{to} \ 0.35) \cdot (\lambda/NA) \end{aligned} \tag{1)'}$$

The previous experiment result can be well explained by this equation.

It is said that in the case of foreign particle inspection on a reticle, the foreign particle size d to be detected is about ¼ of the minimum reticle size. Therefore, when the minimum size on the reticle is 2.5 $\mu$m (in the case of 5:1 reduction transfer, 0.5 $\mu$m on a wafer which is equivalent to 16 MDRAM), the foreign particle size is 0.6 $\mu$m, or when the minimum size on the reticle is 1.5 $\mu$m (equivalent to 64 MDRAM), the foreign particle size is 0.4 $\mu$m.

Therefore, to detect 0.4 $\mu$m foreign particles by a detection optical system with NA=0.4, which is obtained by the previous investigation, a light source with a wave length shorter than $\lambda$=660 nm to 460 nm is necessary from the following equation which is derived from Equation (1)'.

$$\lambda = d \cdot NA/(0.35 \ \text{to} \ 0.24) \tag{2}$$

Next, selection of a wave length which is suited to foreign particle inspection on a sample, such as a reticle with circuit patterns formed thereon in this wave length range, will be investigated. The principle for optically separating and detecting foreign particles from circuit patterns, which is necessary for wave length selection, will be explained first.

The present invention is based on the fact that a reticle circuit pattern comprises straight lines in three directions, such as longitudinal, transverse and slant, and the transposition parts (hereinafter called circuit pattern corners) of the above straight lines. When the above circuit pattern is irradiated by a directional laser beam slantwise at an incident angle of i (i<90°), it is well known that a Fourier transformed image of scattered light from the straight lines of the circuit pattern is condensed at a specific location on the Fourier transport plane into a narrow straight line instead of the circuit pattern location in the illumination field, and the scattered light from foreign particles is not biased to a specific location on the Fourier transform plane.

The present invention filters light scattered by straight portions of the circuit pattern by a linear filtering plate, i.e., a spatial filter, disposed on a Fourier transform image plane and detects light scattered by foreign particles. However, light scattered by corners of the circuit pattern and minute structures consisting of successive corners cannot be filtered. Therefore, the effect of the scattered light which cannot be filtered on inspection in accordance with a processing and memory unit for processing and storing the information of foreign particles detected must be examined.

Figure 36:
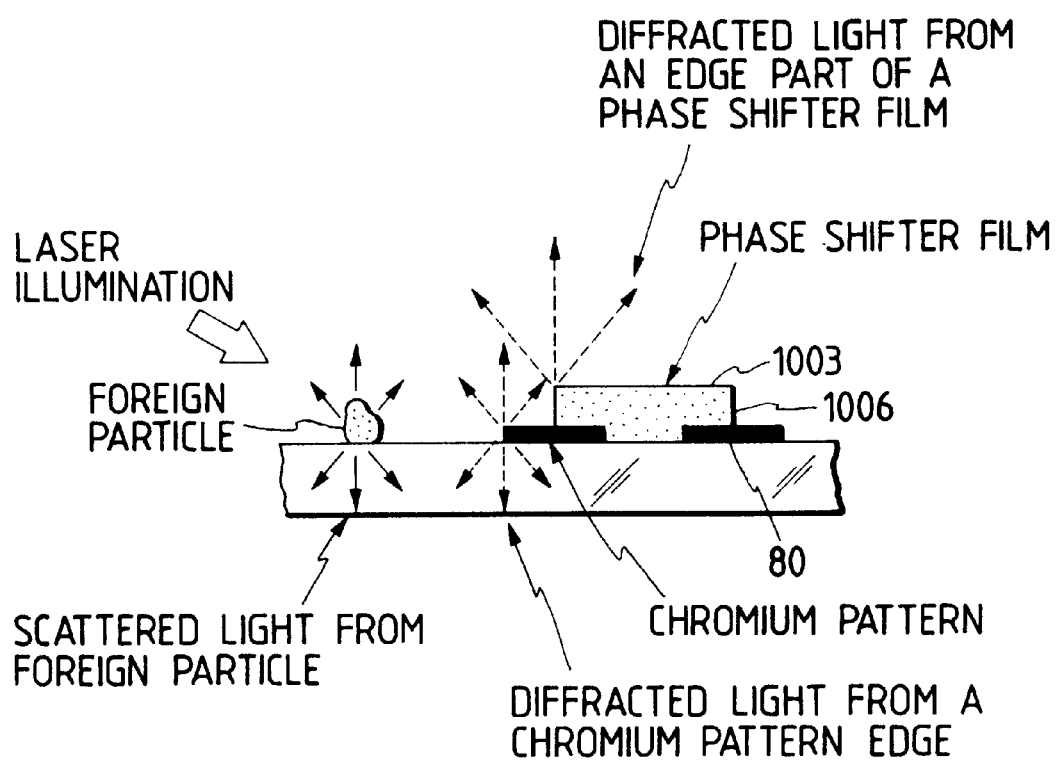
FIG. 36 is a diagrammatic view for assistance in explaining scattered light and diffracted light which has been scattered and diffracted, respectively, by a reticle provided with a phase shifter film.

A reticle as shown in FIG. 36 has been recently developed to improve resolution in transferring a circuit pattern of a metal thin film, such as a chromium thin film (hereinafter referred to as a "chromium pattern"). This recently developed reticle will be referred to as a "phase shift reticle" hereinafter. The phase shift reticle is provided with a pattern of a transparent or translucent thin film (hereinafter referred to as a "phase shift pattern"), which is called a phase shift film or a phase shifter, having a thickness equal to an odd number of times half of the wavelength of light emitted by an exposure light source. The film forming the phase shift pattern is transparent or translucent and has a thickness several times the thickness (on the order of 0.1 $\mu$m) of the chromium pattern.

Figure 16:
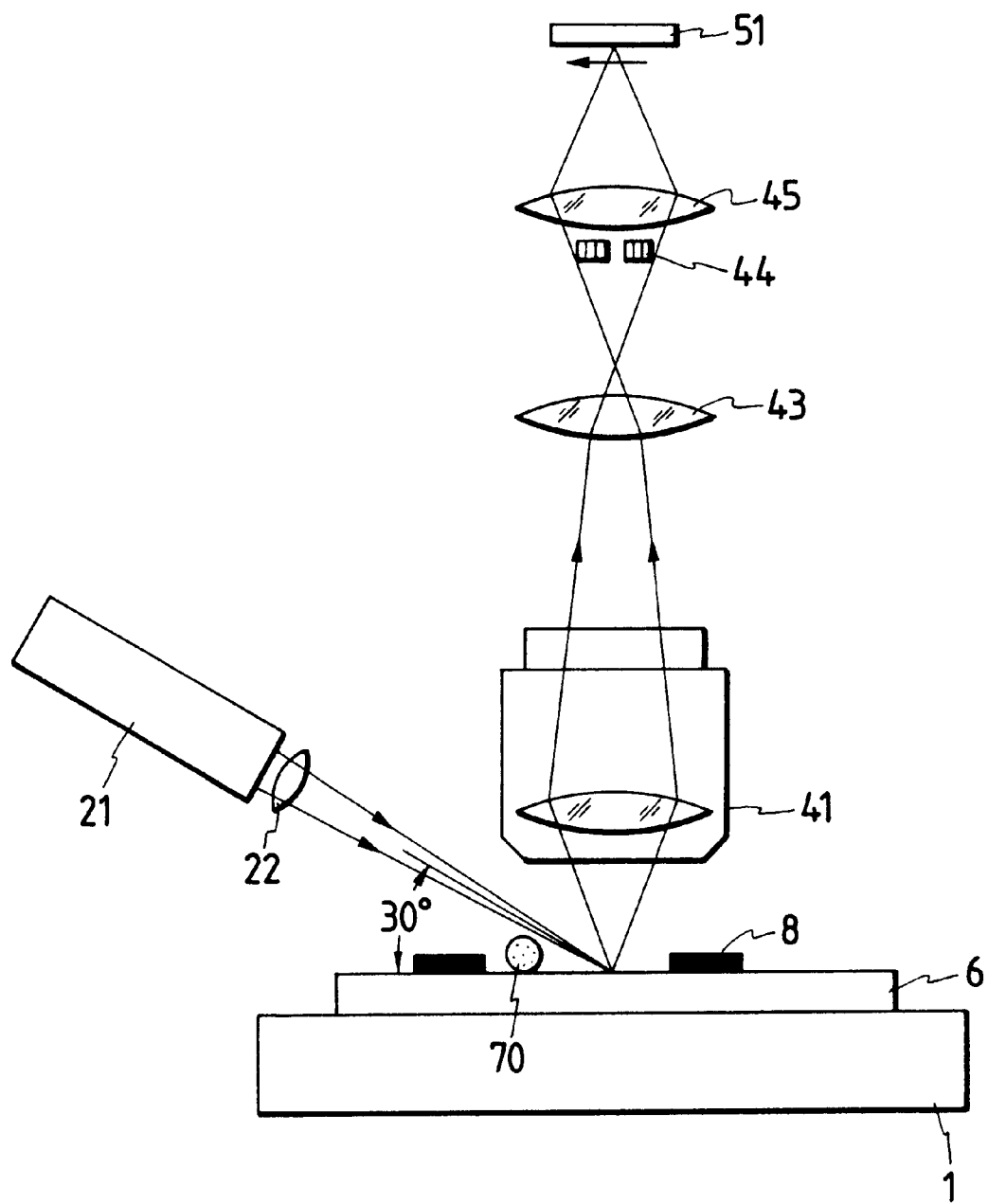
FIG. 16 is a diagrammatic view showing the configuration of a prior art reticle inspecting apparatus.

When inspecting a reticle by the conventional reticle inspecting apparatus, the front surface of the reticle on which the chromium pattern is formed is illuminated and scattered light is gathered by a detection optical system disposed on the side of the front surface (FIG. 16, front illumination mode). When the phase shift reticle is inspected for foreign particles in this front illumination mode, there arises a problem that light scattered by edges of the phase shifter pattern, which is several times to several tens of times greater than light diffracted by edges of the chromium pattern, reduces the foreign particle detection sensitivity greatly.

This invention utilizes a fact that the edges of the phase shifter pattern extend onto the chromium pattern of an opaque film to solve the problem. When the illuminating light is projected from the side of the back surface of the reticle and the scattered light is gathered by the detection optical system disposed on the side of the front surface of the reticle (FIG. 17, back illumination mode), the illuminating light traveling toward the edges of the phase shift pattern is intercepted by the chromium pattern of an opaque film of the phase shift reticle and, consequently, the foreign particle detection sensitivity is not reduced because the illuminating light is not scattered by the phase shift pattern.

The back illumination mode is able to detect only foreign particles in the light-transmissive portions, i.e., portions in which any elements of the chromium pattern are not formed. Practically, foreign particles on the chromium pattern also need to be detected. Accordingly, it is desirable to illuminate the reticle in both the front illumination mode and the back illumination mode in combination. The front illumination mode and the back illumination mode will be described hereinafter in terms of foreign particles and the intensity of the light scattered by the front surface of the reticle.

Figure 18:
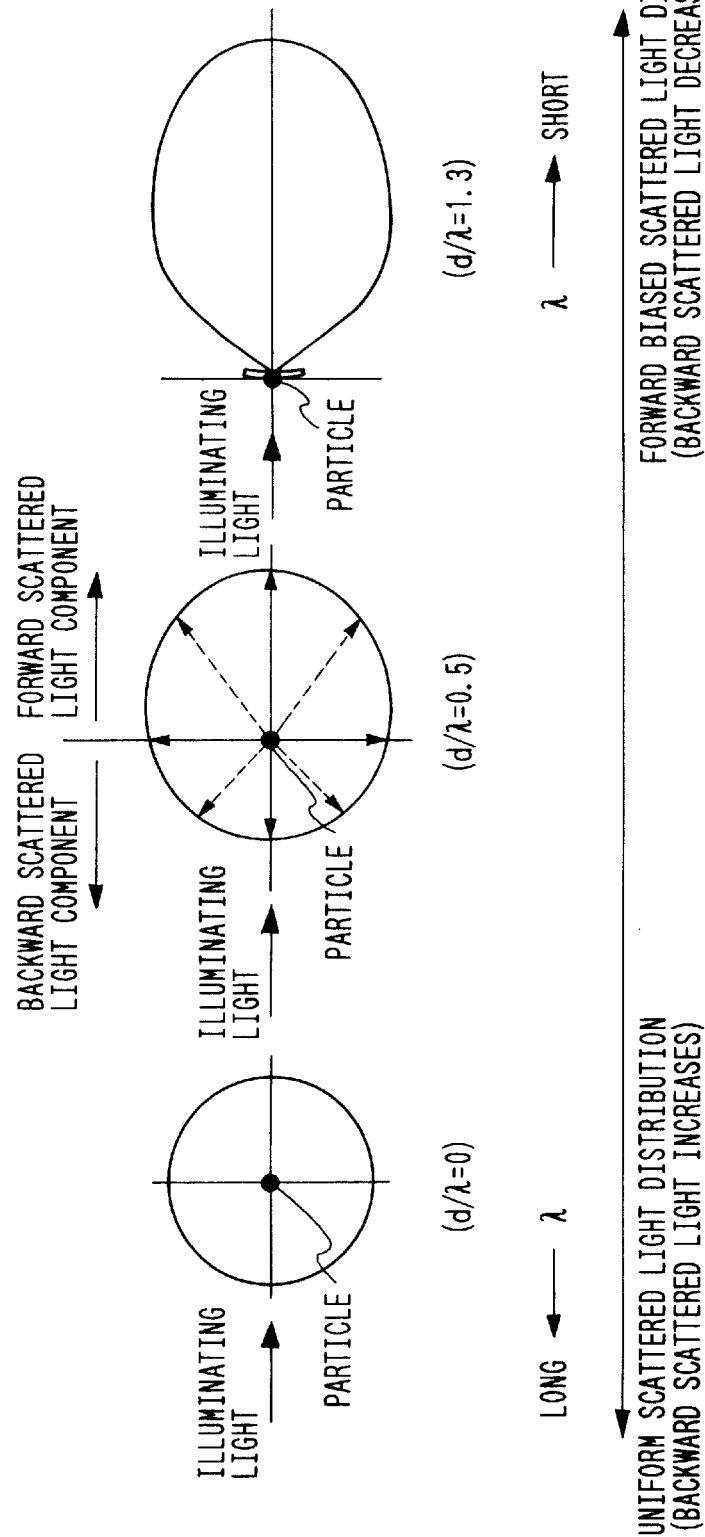
FIG. 18 is a diagrammatic view showing the relation between the distribution of components of light scattered by a particle and d/$\lambda$, where d is the size of the particle and $\lambda$ is the wavelength of the illuminating light beam.

According to the light scattering theory, light scattered by particles is in similar correspondence in respect of the relation between wavelength and particle size. FIG. 18 shows the relation between the distribution of scattered light scattered by a particle and $d/\lambda$ (d: size of the particle, $\lambda$: wavelength of the light emitted by a light source). The light component scattered in the direction of travel of the illuminating light is called a forward scattered light component, and the light component scattered in the direction opposite the direction of travel of the illuminating light is called a backward scattered light component.

When the illuminating light falls on a particle having a certain size, the shorter the wavelength of the illuminating light, the greater will be the forward scattered light component, and the longer the wavelength of the illuminating light, the higher will be the uniformity of distribution of the scattered light components and the greater will be the ratio of the backward scattered light component to all the scattered light components.

Figure 1:
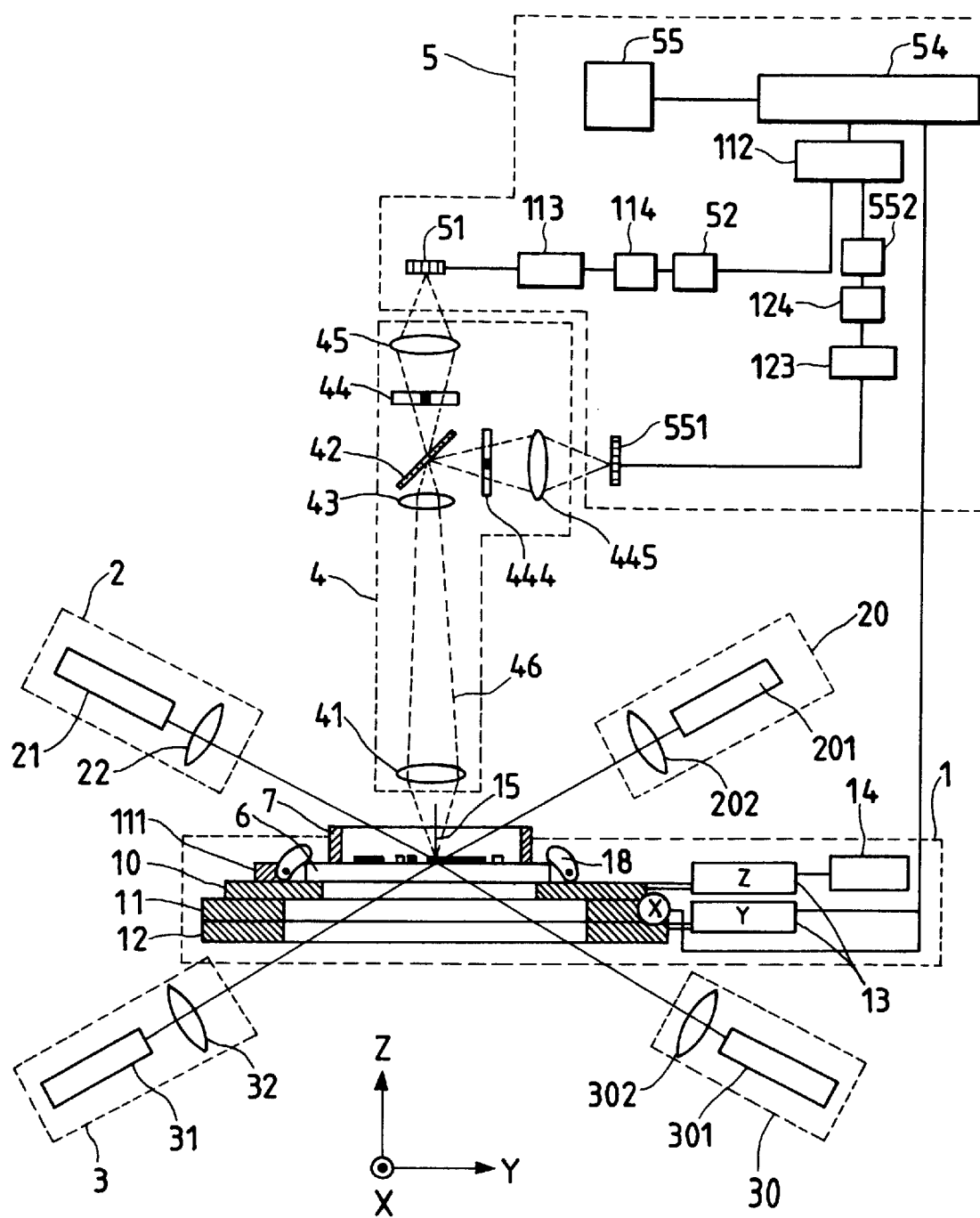
FIG. 1 is a diagrammatic view of a reticle inspecting apparatus in a first embodiment according to the present invention.
Figure 2:
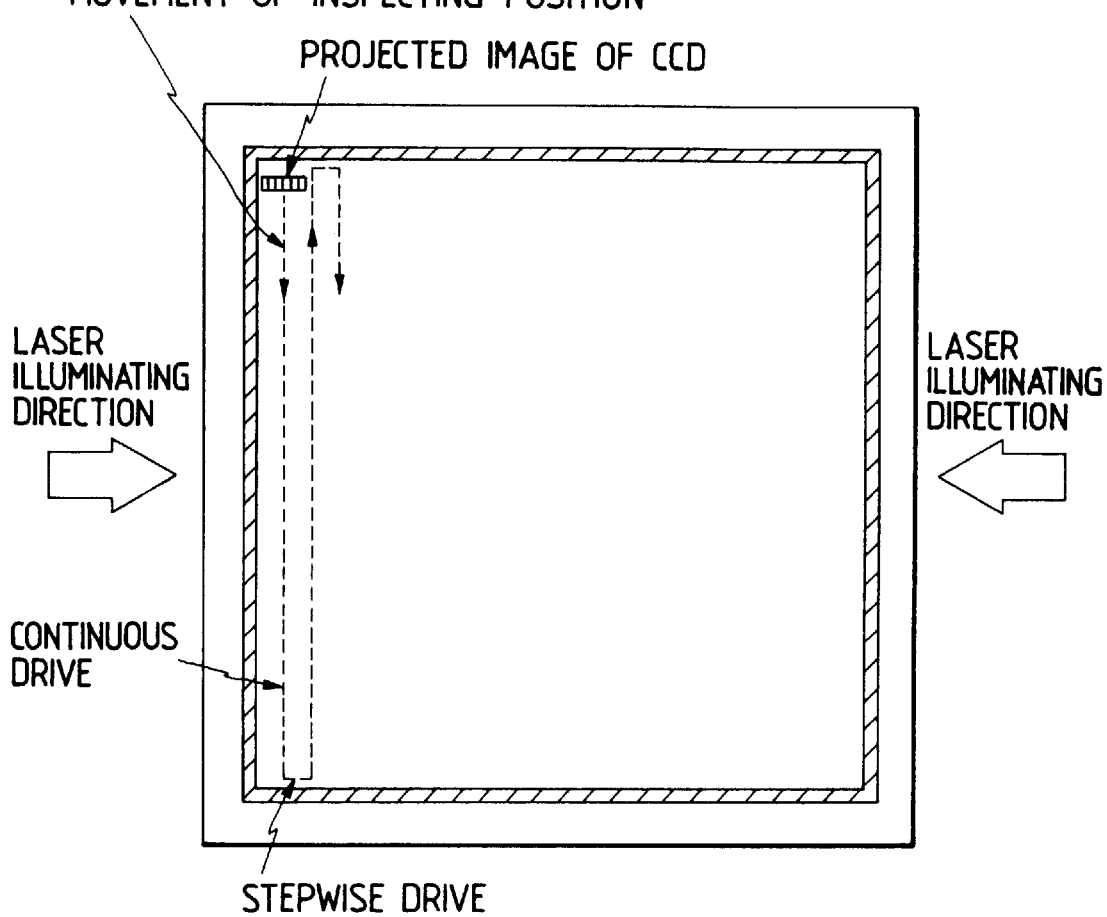
FIG. 2 is a plan view of a reticle for assistance in explaining a reticle scanning method in accordance with the present invention.
Figures 2, 19:
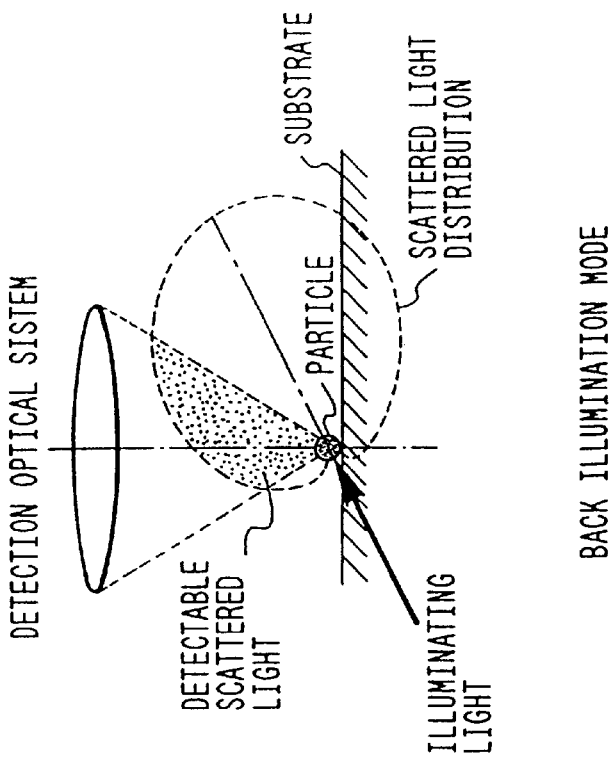
Figures 1, 19:
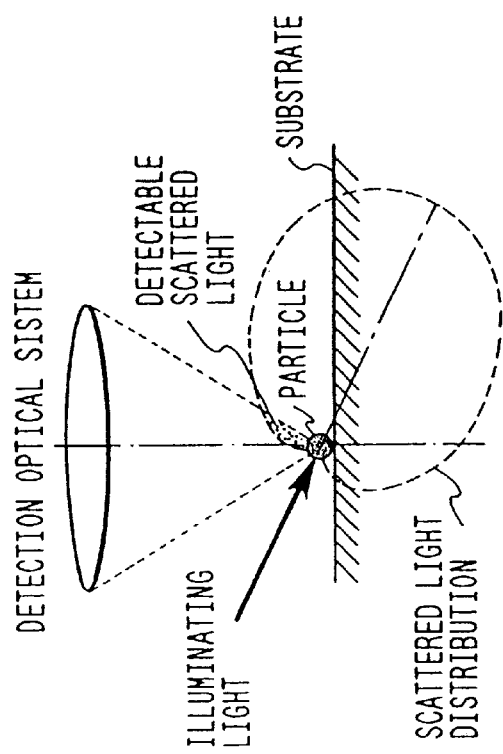

FIG. 19-1 shows the positional relation between the direction of travel of the illuminating light and the detection optical system for the front illumination mode, and FIG. 19-2 shows the positional relation between the direction of travel of the illuminating light and the detection optical system for the back illumination mode. The front illumination mode detects the backward scattered light component, and the back illumination mode detects the forward scattered light component. As shown in FIG. 18, the forward scattered light component is always greater than the backward scattered light component. Therefore, it is effective to detect the forward scattered light component to obtain a high foreign particle detection signal. Thus, it is advantageous to detect the forward scattered light component in the back illumination mode to detect foreign particles in the light-transmissive portions of the reticle, whether the reticle is provided with the phase shifter pattern or not.

A reticle inspecting apparatus for inspecting a reticle, such as a photomask, fabricated by forming a circuit pattern of an opaque film on a transparent (or translucent) substrate, for foreign particles adhering to the substrate is able to provide high foreign particle detection signals by detecting foreign particles in the opaque portions in the front illumination mode and detecting foreign particles in the light-transmissive portions in the back illumination mode.

In either illumination mode, a maximum foreign particle detection signal can be obtained by using illuminating light having an optimum wavelength. Experiments were conducted to determine illuminating light having an optimum wavelength to obtain a maximum foreign particle detection signal through the examination of the dependence of the detecting ability on the wavelength of illuminating light.

In the front illumination mode, the backward scattered light component, and hence the foreign particle detection signal, will increase with the increase of the wavelength of the illuminating light.

FIG. 20 shows the variation of the chromium pattern detection signal provided when the chromium pattern is detected and the variation of the particle detection signal provided when a 0.5 $\mu$m particle on the chromium pattern (opaque portion) is detected in the front illumination mode with the wavelength of the illuminating light. Laser beams of 830 nm, 780 nm, 633 nm, 532 nm, 515 nm and 488 nm, respectively, in wavelength were used as illuminating light beams. In the wavelength range of 488 nm to 830 nm, the longer the wavelength, the higher is the particle detection signal, and the particle detection signal reaches a peak when the wavelength is 780 nm. The chromium pattern detection signal varies with the wavelength in a comparatively narrow range.

Figure 21:
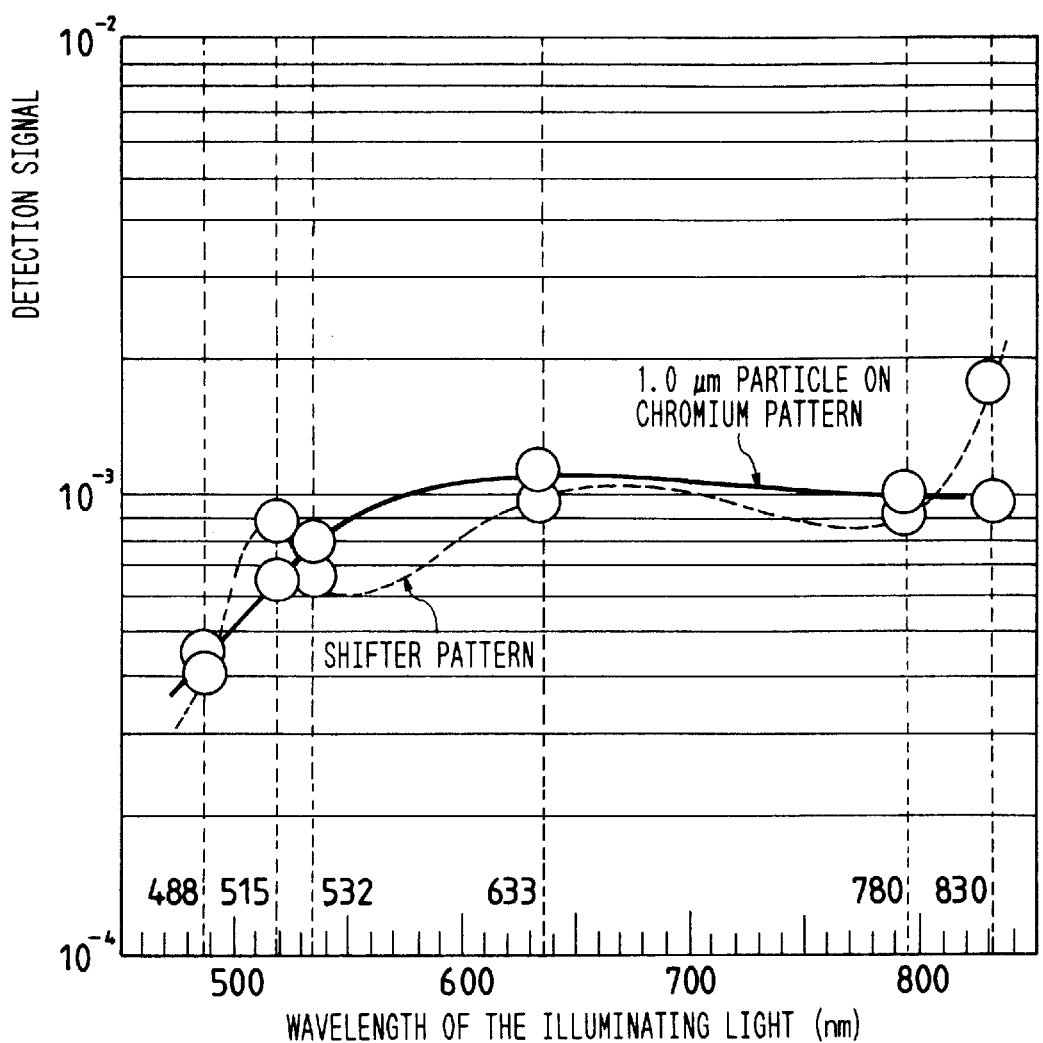
FIG. 21 is a graph showing the respective variations of detection signals provided when a 1.0 $\mu$m particle on the chromium pattern is detected and when the phase shifter pattern is detected, respectively, in the front illumination mode with the wavelength of the illuminating light beam.

FIG. 21 shows the variation of a shifter pattern detection signal provided when the shifter pattern is detected and the variation of the particle detection signal provided when a 1.0 $\mu$m particle on the chromium pattern (opaque portion) is detected in the front illumination mode with the wavelength of the illuminating light. Laser beams of 830 nm, 780 nm, 633 nm, 532 nm, 515 nm and 488 nm, respectively, in wavelength were used as illuminating light beams. In the wavelength range of 488 nm to 830 nm, the longer the wave-length, the higher are both the particle detection signal and the shifter pattern detection signal.

In the back illumination mode, the shorter the wavelength of the illuminating light, the greater is the forward scattered light component and the higher is the particle detection signal.

Figure 22:
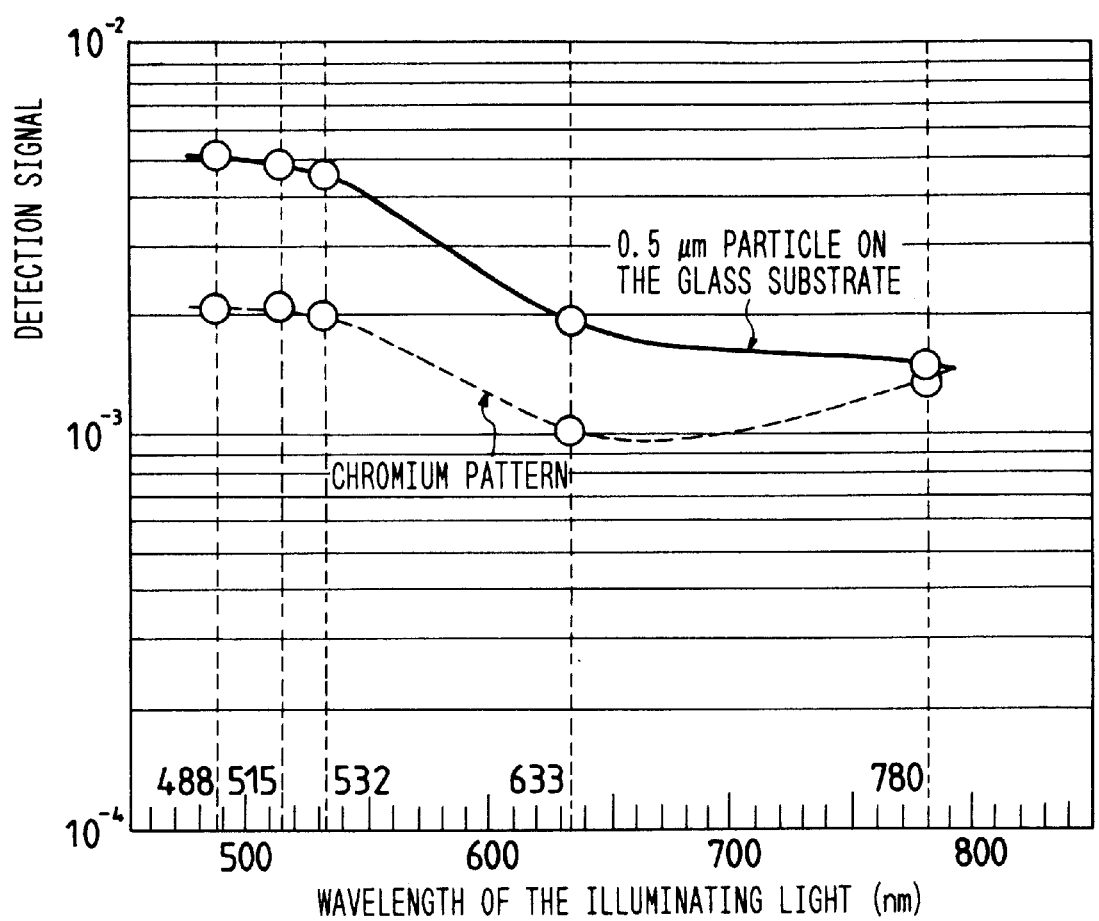
FIG. 22 is a graph showing the respective variations of detection signals provided when a 0.5 $\mu$m particle on a glass substrate is detected and when the chromium pattern is detected, respectively, in the back illumination mode with the wavelength of the illuminating light beam.

FIG. 22 shows the variation of the particle detection signal provided when a 0.5 $\mu$m particle on the glass plate (light-transmissive portion) is detected and the variation of chromium pattern detection signal provided when the chromium pattern is detected in the back illumination mode with the wavelength of the illuminating light. In the back illumination mode, the shifter pattern does not scatter the illuminating light at all. Laser beams of 780 nm, 633 nm, 532 nm, 515 nm and 488 nm, respectively, in wavelength were used as illuminating light beams. The shorter the wavelength, the higher is the particle detection signal. Although the shorter the wavelength, the higher the chromium pattern detection signal, the chromium pattern detection signal varies with the wavelength less sharply than the particle detection signal.

When inspecting a sample provided with a circuit pattern for foreign particles, the relation between the foreign particle detection signal provided when light scattered by a foreign particle is detected and the pattern detection signal provided when light scattered by the circuit pattern is detected must be taken into consideration. This relation is represented by a discrimination ratio defined by:

(Discrimination ratio)=(Output of the detector provided when light scattered by a foreign particle is detected)/ (Output of the detector provided when light scattered by the pattern is detected)

If the discrimination ratio is greater than "1", the foreign particle can be detected through the comparison (binarization) of the scattered light detection signals by an apparatus having a simple configuration. In a practical apparatus, the detection signal is affected by electrical noise, optical noise, vibrations of the mechanical parts, the variation of sensitivity of the detection system and so forth. Therefore, there must be a significant difference between the level of light scattered by the foreign particle and that of light scattered by the chromium pattern; that is, the greater the discrimination ratio, the higher will be the foreign particle detecting ability.

The foregoing experimental results were examined to determine the wavelengths of illuminating light beams to enhance the detecting abilities of the front illumination mode and the back illumination mode to a maximum.

Figure 23:
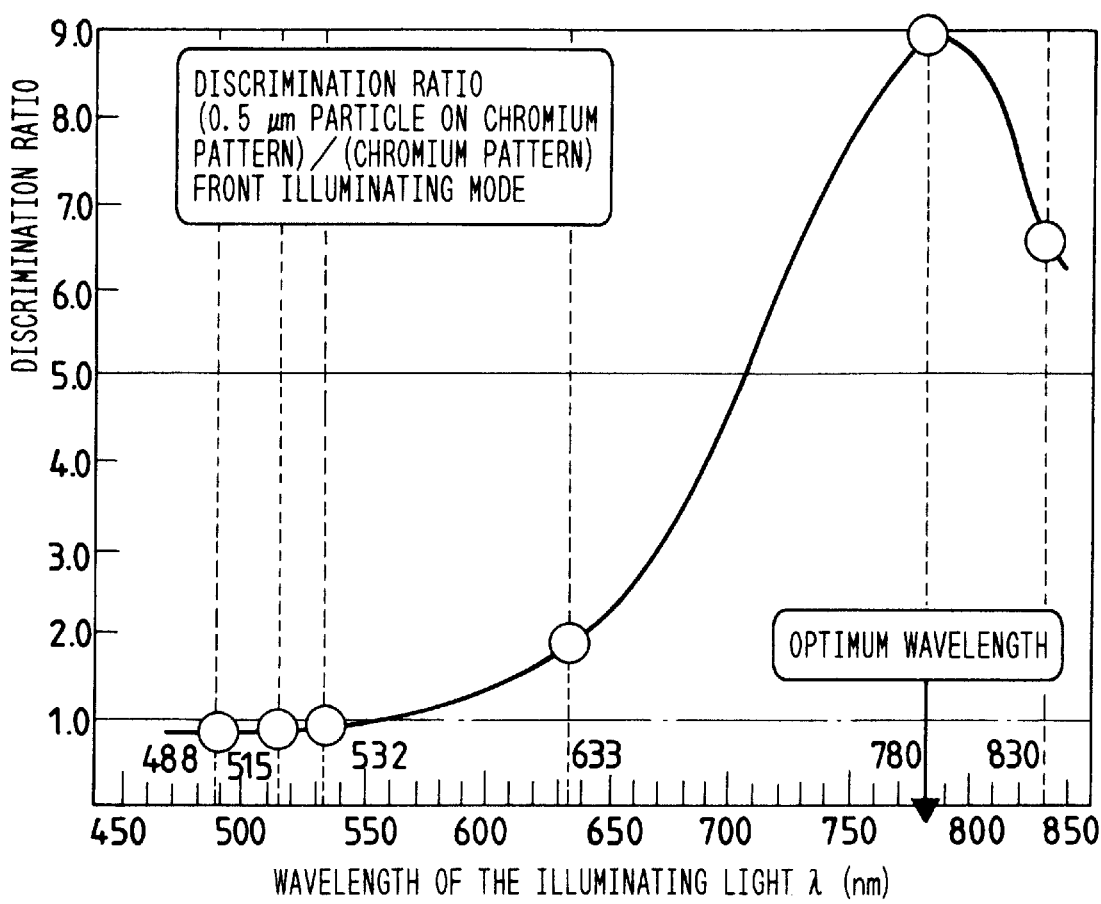
FIG. 23 is a graph showing the variation of the discrimination ratio (0.5 $\mu$m particle on the chromium pattern vs the chromium pattern) with the wavelength of the illuminating light beam used in the front illumination mode.
Figure 24:
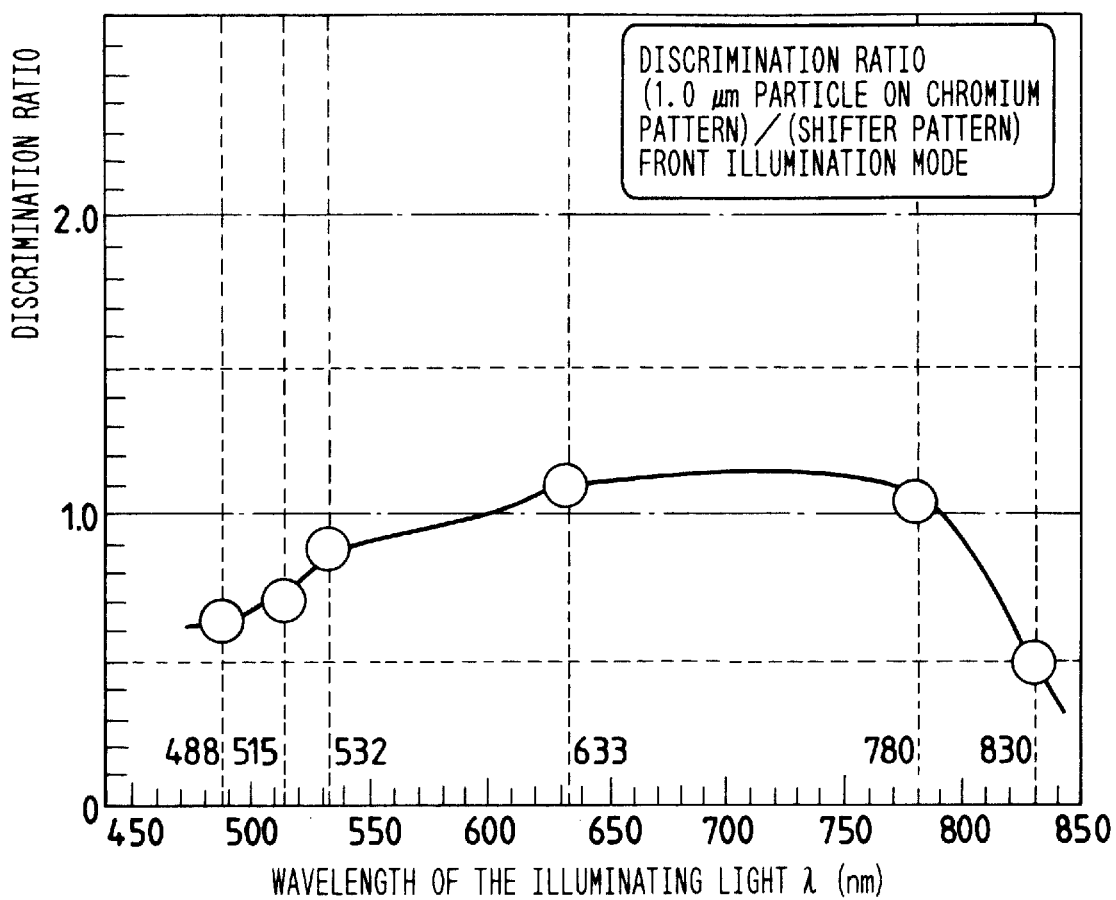
FIG. 24 is a graph showing the variation of the discrimination ratio (1.0 $\mu$m particle on the chromium pattern vs the phase shifter pattern) with the wavelength of the illuminating light beam used in the front illumination mode.

FIGS. 23 and 24 show the variation of the discrimination ratio with the wavelength of the illuminating light beam in the inspection in the front illumination mode.

(1) FIG. 23: A 0.5 μm standard particle on the chromium pattern vs chromium pattern (Maximum value)

(2) FIG. 24: A 1.0 μm standard particle on the chromium pattern vs shifter pattern (Maximum value)

It is known from FIG. 23 that the 0.5 μm standard particle on a reticle not provided with any phase shift film can be most stably detected when an illuminating light beam having a wavelength around 780 nm is used.

It is known from FIG. 24 that the 1.0 μm standard particle on the chromium pattern of a phase shift reticle can be detected by using an illuminating light beam having a wavelength in the range of 600 nm to 800 nm.

From these facts, as seen from FIGS. 23 and 24, it is considered that an illuminating light beam having a wavelength around 780 nm is an optimum illuminating light beam for the front illumination mode.

A light source capable of emitting such an optimum illuminating light beam having a wavelength around 780 nm is a semiconductor laser. It is obvious from FIG. 23 that the discrimination ratio achieved by using this optimum illuminating light beam is higher than that achieved by using a laser beam having a wavelength of 632.8 nm emitted by a red He-Ne laser, which has been widely used, and the optimum illuminating light beam secures stable foreign particle detection.

Figure 25:
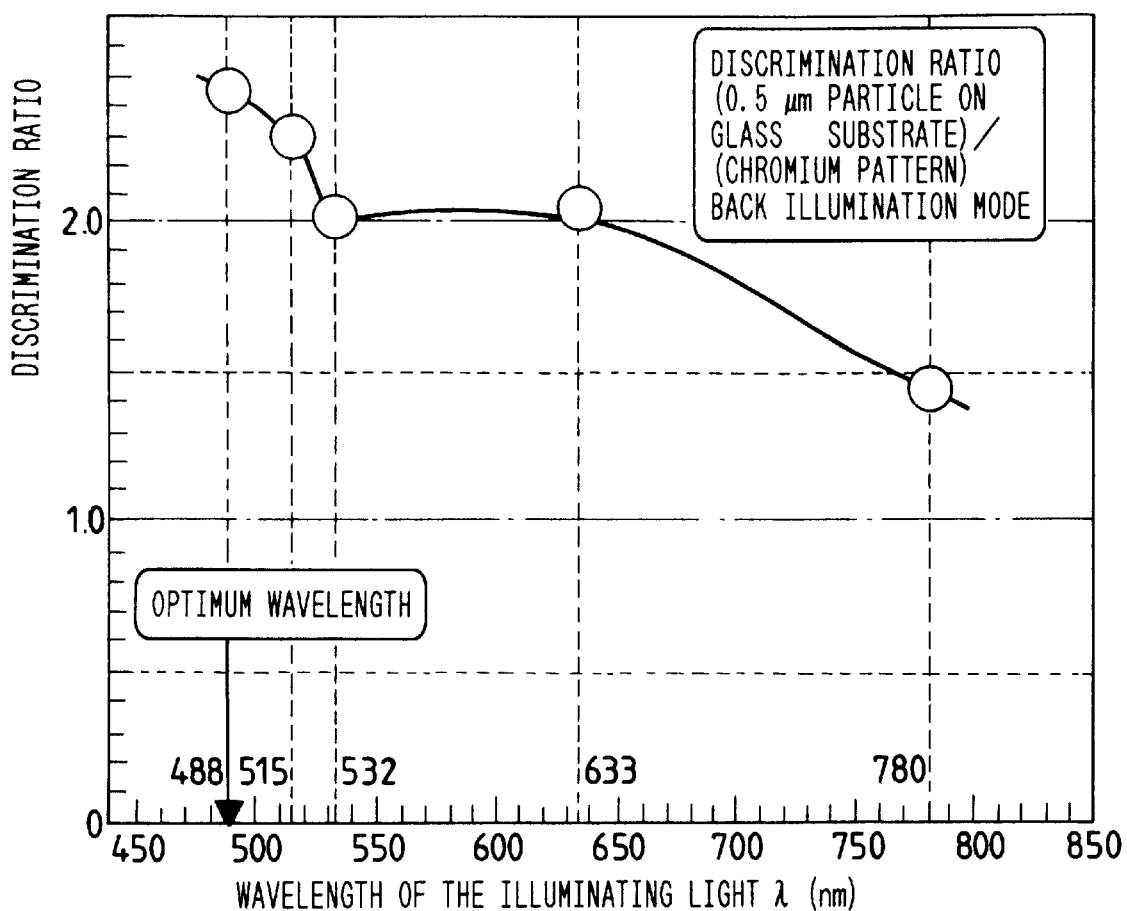
FIG. 25 is a graph showing the variation of the discrimination ratio (0.5 $\mu$m particle on the glass substrate vs the chromium pattern) with the wavelength of the illuminating light beam used in the back illumination mode.

FIG. 25 shows the variation of the discrimination ratio with the wavelength of the illuminating light beam in the inspection in the back illumination mode.

(1) FIG. 25: A 0.5 μm standard particle on the glass substrate vs the chromium pattern (Maximum value)

It is seen from FIG. 25 that the discrimination ratio reaches a maximum when an illuminating light beam having a wavelength of around 488 nm is used in the inspection in the back illumination mode. is A light source that emits light having a wavelength of about 488 nm is the Ar ion laser. The Ar ion laser having a large output capacity can be easily fabricated; for example, an air-cooled Ar ion laser can provide an output as large as several tens of milliwatts, while a water-cooled Ar ion laser can provide an output as large as several watts. Therefore, the detection signal when an Ar ion laser beam is used is higher than that when a red He-Ne laser beam is used.

Thus, from the foregoing, the present invention uses oblique illumination by an illuminating light beam having a wavelength of about 780 nm for the front illumination mode and oblique illumination by an illuminating light beam having a wavelength of about 488 nm in combination for the discriminative detection of foreign particles and a circuit pattern on a sample provided with a phase shift film.

The foregoing optimum wavelengths are selected on an assumption that the size of a minimum foreign particle among those to be detected is 0.5 μm. Since the greater the size of foreign particles, the higher will be the detection signal, i.e., the amount of scattered light, a wavelength that makes the detection signal a maximum when a foreign particle having the minimum size is detected is the optimum wavelength. Since scattering is in similar correspondence in respect of the relation d/λ (d is the size of the particle and λ is the wavelength of the illuminating light beam) Ref from the foregoing experimental results, an optimum wavelength is on the order of 1.6 d for the front illumination mode and on the order of 1.0 d for the back illumination mode, where d is the size of the smallest foreign particle among those to be detected.

Although the backward scattered light component increases if an illuminating light beam having a wavelength greater than the optimum wavelength is used for the front illumination mode, the total amount of scattered light decreases in inverse proportion to the fourth power of the wavelength of the illuminating light beam (Reyleigh scattering), entailing the reduction of the particle detection signal. If an illuminating light beam having a wavelength smaller than the optimum wavelength for the back illumination mode is used for oblique illumination, the forward scattered light component increases excessively and the amount of light that falls on the detection optical system decreases, reducing the particle detection signal. When the size of the smallest foreign particle among those to be detected is 0.5 μm, the wavelength for the front illumination mode must be in the range of 600 nm to 800 nm and the wavelength for the back illumination mode must be in the range of 450 nm to 550 nm.

Referring to FIG. 1, an inspection stage unit 1 comprises a Z-stage 10, provided with a pellicle 7 and capable of being moved in the Z-direction, and a fastening device 18 for fastening a reticle 6 on the Z-stage; an X-stage 11 for moving the Z-stage 10 supporting the reticle 6 in the X-direction; a Y-stage 12 for moving the Z-stage 10 supporting the reticle 6 in the Y-direction; a stage driving system 13 for driving the Z-stage 10, the X-stage 11 and the Y-stage 12 for movement; and a control system 14 for detecting the position of the reticle 6 with respect to the Z-direction to position the reticle 6 for focusing. The stages 10, 11 and 12 are controlled with a necessary accuracy for focusing during the inspection of the reticle 6.

The X-stage 11 and the Y-stage 12 are controlled for movement for scanning along scanning lines as shown in FIG. 2 at an optional moving speed. For example, the X-stage is driven for a periodic movement in a half-cycle time of about 0.2 sec for uniformly accelerated motion, 4.0 sec for uniform motion, 0.2 sec for uniformly decelerated motion and about 0.2 for stopping, at a maximum velocity of about 25 mm/sec in an amplitude of 105 mm. The Y-stage 12 is driven for intermittent movement in the Y-direction in synchronism with the uniformly accelerated motion and the uniformly decelerated motion of the X-stage 11 at a step of 0.5 mm. If the Y-stage 12 is moved 200 times at a step of 0.5 mm, the reticle 6 can be moved 100 mm in about 960 sec, and an area of 100 mm square can be scanned in about 960 sec.

The stage driving system 13 may be provided with an air micrometer, a laser interferometer or a device employing a stripe pattern to position the reticle 6 for focusing. In FIGS. 1 and 2, the X-direction, the Y-direction and the Z-direction are indicated by the arrows X, Y and Z. respectively.

The reticle inspecting apparatus has a first front illuminating unit 2, a second front illuminating unit 20, a first back illuminating unit 3 and a second back illuminating unit 30, which are individual systems having the same configuration. The front illuminating units 2 and 20 are provided respectively with laser light sources 21 and 201 which emit light beams of 780 nm in wavelength. The back illuminating units 3 and 30 are provided respectively with laser light sources 31 and 301 which emit light beams of 488 nm in wavelength. Laser beams emitted by the laser light sources 21, 201, 31 and 301 are condensed respectively by condenser lenses 22, 202, 32 and 302 to illuminate a circuit pattern formed on the front surface of the reticle 6. The incidence angle i of each of the light beams emitted by the laser light sources 2, 20, 3 and 30 on the circuit pattern must be greater than about 30° to avoid the interception of the light beam by the objective lens 41 of a detection optical system 4 and must be smaller than about 80° to avoid the interception of the same by the pellicle 7 mounted on the reticle 6. Therefore, about 30°<i<about 80°.

Since the first front illuminating unit 2, the second front illuminating unit 20, the first back illuminating unit 3 and the second back illuminating unit 30 have the same configuration, only the first front illuminating unit 2 will be described with reference to FIG. 3, in which parts like or corresponding to those shown in FIG. 1 are denoted by the same reference characters. The first front illuminating unit 2 is provided with the condenser lens 22 consisting of a convex lens 223, a cylindrical lens 224, a collimator lens 225 and a condenser lens 226.

The laser light sources 21 and 201 of the front illuminating units 2 and 20 are disposed so that light beams emitted by the laser light sources 21 and 201 are linearly polarized light beams (s-polarized light beams) having an electric vector which remains pointing in the X'-direction. The s-polarized light beams are used because the reflectivity of the s-polarized light beams incident on a glass substrate at an incidence angle i of about 60° is about five times greater than that of the p-polarized light beams (linearly polarized light having the electric vector which remains pointing in Y'-direction), and hence, the s-polarized light beams are more suitable for detecting small particles than the p-polarized light beams.

The laser light sources 31 and 301 of the back illuminating units 3 and 30 are disposed so that light beams emitted by the laser light sources 31 and 301 are s-polarized light beams, because experiments have shown that the discrimination ratio when the s-polarized light beam is used is greater than the discrimination ratio when the p-polarized light beam is used. However, in some cases, the p-polarized light beam is preferred to the s-polarized light beam, taking into consideration the transmittance of the substrate.

The present invention uses spatial filters disposed on the Fourier transform plane of the detection optical system 4 to discriminate between foreign particles and the circuit pattern. The use of a collimated light beam reduces the spread of light diffracted by the circuit pattern to increase the discrimination ratio. However, the use of gathered light of high intensity will raise the output level of the detector and improve the SN ratio.

If the NA of the converging system is about 0.1 and the diameter of the laser beam is reduced to about 10 $\mu$m to increase the intensity of the laser beam emitted by each of the illuminating units 2, 20, 3 and 30, the depth of focus is as small as about 30 $\mu$m, which is smaller than the size (500 $\mu$m) of the entire area S of an inspection field (FIG. 3), and so the entire area S of the inspection field 15 cannot be brought into focus. In this reticle inspecting apparatus, the cylindrical lens 214 is turned about the X'-axis as shown in FIG. 3 to bring the entire area S of the inspection field 15 into focus when the incidence angle i is, for example, 60°. Accordingly, even if the detectors 51 and 551 of a signal processing system 5 are one-dimensional solid state imaging devices and the inspection area of the inspection field 15 has a linear shape, the linear inspection area can be uniformly illuminated to a high illuminance.

When the cylindrical lens 224 is turned about both the X'-axis and the Y'-axis (FIG. 3), the entire area S of the inspection field 15 can be uniformly and linearly illuminated to a high illuminance even if the light beam is projected from an optional direction so as to fall on the reticle at an incidence angle i of 60°.

Referring again to FIG. 1, the detection optical system 4 comprises the objective lens 41 disposed opposite to the front surface of the reticle 6, a field lens 43 disposed near the focal point of the objective lens 41, and a wavelength separating mirror 42. The light incident on the detection optical system 4 is separated into a scattered light component and a diffracted light of the front illuminating units 2 and 20, and those of the back illuminating units 3 and 30. The separated light components travel through spatial filters 44 and 444, disposed on Fourier transform planes with respect to the inspection field 15 on the reticle 6 and each having a band-like screening portion and light-transmissive portions on the opposite sides of the band-like screening portion, and focusing lenses 45 and 445 and form images of the inspection field 15 on the reticle 6 on the detectors 51 and 551 of the signal processing system 5, respectively. The field lens 43 forms an image of a focus position 46 above the objective lens 41 on the spatial filters 44 and 444.

The signal processing system 5 comprises the detectors 51 and 551, a first binarizing circuit 52 and a second binarizing circuit 552, respectively, for binarizing the outputs of the detectors 51 and 551, a microcomputer 54, and a display 55.

Each of the detectors 51 and 551 is, for example, a one-dimensional solid-state imaging device of a charge transfer type. When a defect, such as a foreign particle, is found in the inspection field 15 while the circuit pattern of the reticle 6 is scanned by moving the X-stage 10, the level of the light signal representing the circuit pattern, i.e., the intensity of the incoming light, increases and, consequently, the outputs of the detectors 51 and 551 increase. The one-dimensional solid-state imaging device is advantageous because the inspection field 15 can be expanded without reducing the resolution. The detectors 51 and 551 may be two-dimensional solid-state imaging devices or solid-state image sensors.

A binarizing threshold is set for the binarizing circuits 52 and 552. When the binarizing circuits 52 and 552 receive outputs of the detectors 51 and 551 exceeding a level corresponding to the intensity of reflected light corresponding to the size of a foreign particle to be detected, the binarizing circuits 52 and 552 provide a logical "1".

The shading compensating circuits 113 and 123 and 4-pixel addition circuits 114 and 124 will be described later.

A blocking circuit 112 receives the output signals of the binarizing circuits 52 and 552 and prevents a double count of the two signals, which will be described later.

Upon the reception of a logical "1" from the blocking circuit 112, the microcomputer 54 decides that a defect has been found, stores defect data including information about the respective positions of the X-stage 10 and the Y-stage 11, information about the position of the defect determined by calculation on the basis of the pixels, i.e., the solid-state image sensors of the detectors 51 and 551, corresponding to the defect, and the values of the outputs of the detectors 51 and 551, and displays the defect data on the display 55.

Figure 5:
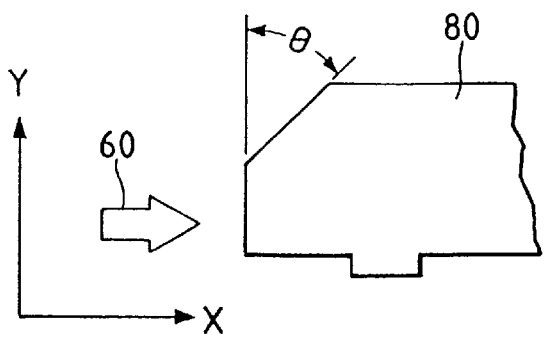
FIG. 5 is a schematic diagram for assistance in explaining an angular circuit pattern.
Figure 6A:
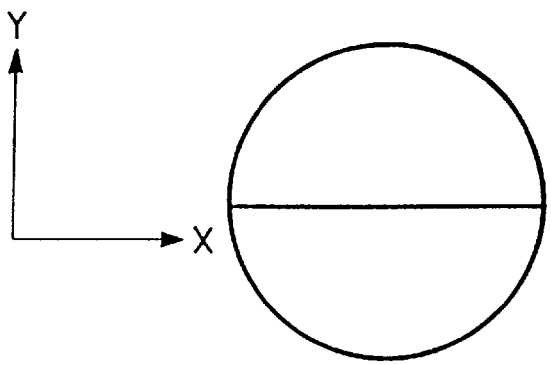
FIGS. 6(a), 6(b) and 6(c) are views showing the distribution of scattered light and that of diffracted light on a Fourier transform plane.
Figure 6B:
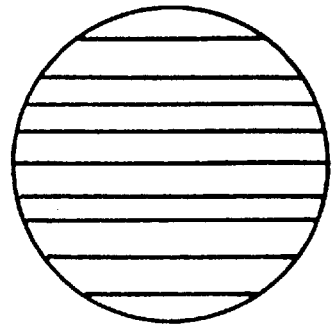
Figure 6C:
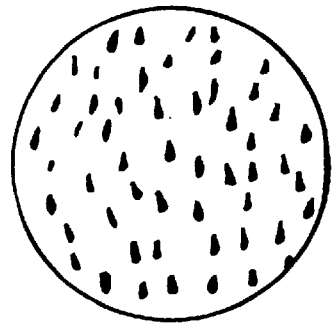
Figure 7A:
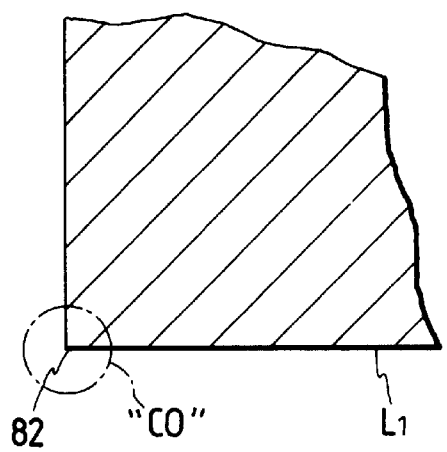
FIGS. 7(A) and 7(B) are a fragmentary plan view of a corner of a circuit pattern and an enlarged view of a portion CO of FIG. 7(A), respectively.
Figure 7B:
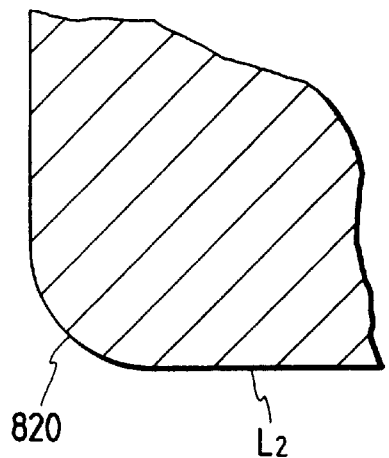
Figure 8:
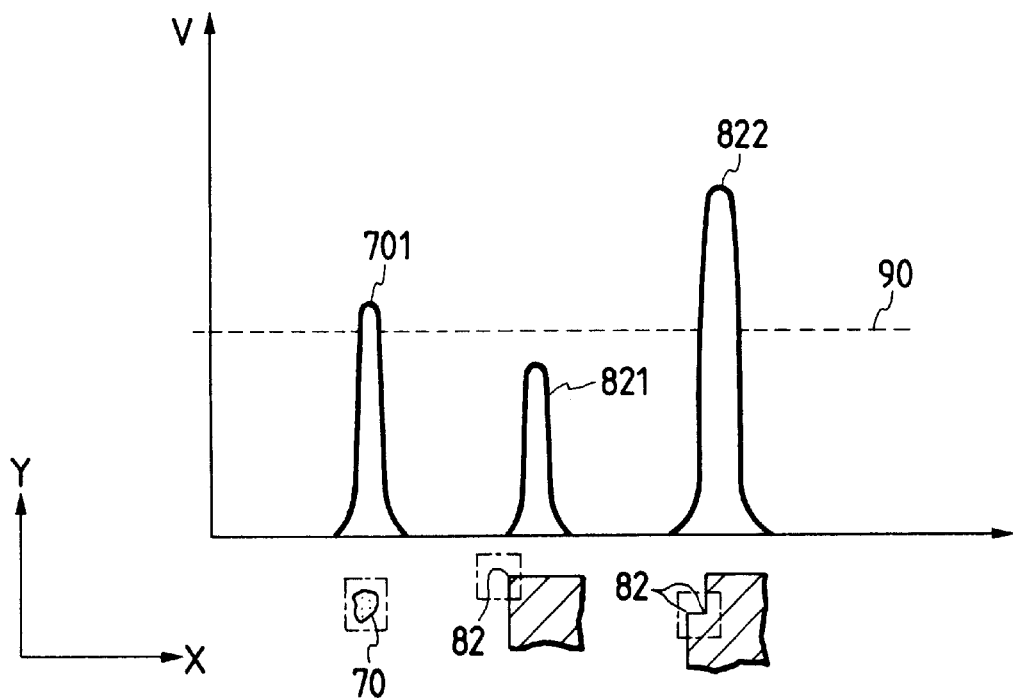
FIG. 8 is a graph for assistance in explaining the relation between a scattered light detection signal provided when light scattered by a foreign particle is detected and a detection signal provided when a circuit pattern is detected.
Figure 9:
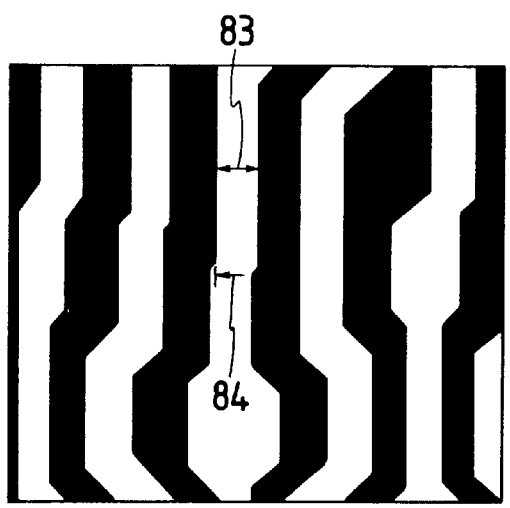
FIG. 9 is a plan view of a minute circuit pattern to be inspected for defects by the reticle inspecting apparatus of the present invention.
Figure 10:
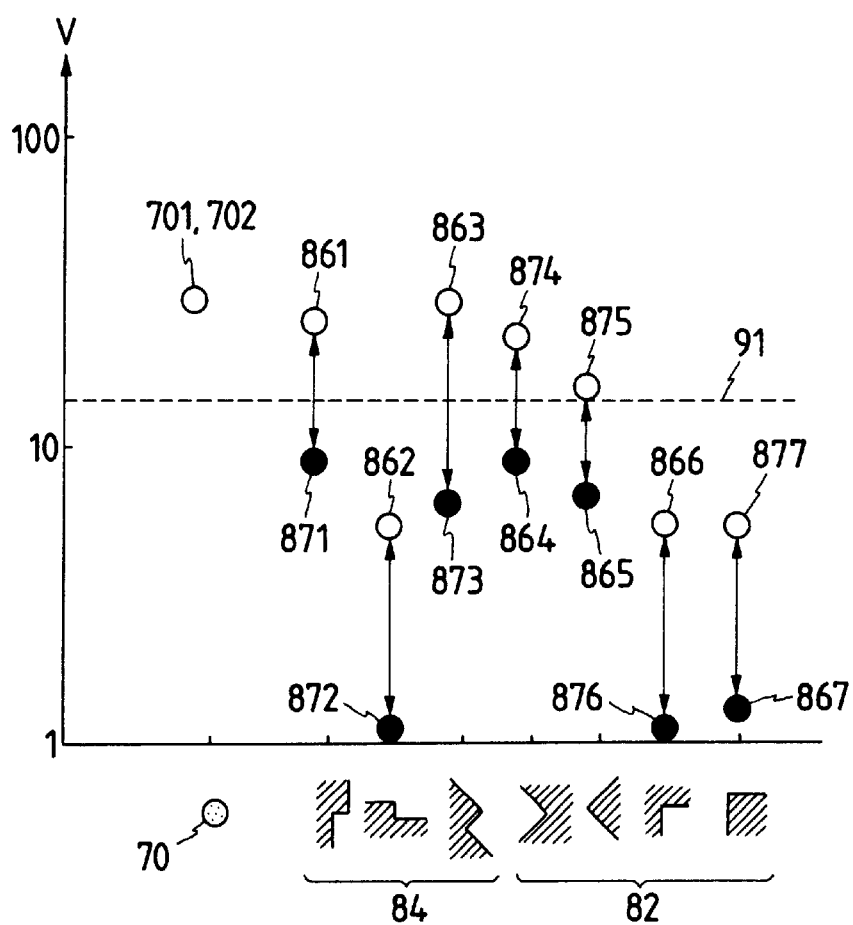
FIG. 10 is a graph showing the levels of detection signals provided when a foreign particle and corners of a circuit pattern are detected.

The operation of the reticle inspecting apparatus will be described with reference to FIGS. 4 to 10, in which parts like or corresponding to those shown in FIG. 1 are denoted by the same reference characters. FIG. 2 is a view for assistance in explaining a reticle scanning method, FIG. 5 is a detail view for assistance in explaining an angular portion of the circuit pattern, FIGS. 6(a)–(e) are views showing the distribution of scattered light and that of diffracted light on the Fourier transform plane, FIG. 7(A) is a fragmentary plan view of a corner of a circuit pattern and FIG. 7(B) is an enlarged view of a portion Co of FIG. 7(A), FIG. 8 is a graph for assistance in explaining the relation between a scattered light detection signal provided when light scattered by a foreign particle is detected and a detection signal provided when a circuit pattern is detected, FIG. 9 is a plan view of a minute circuit pattern, and FIG. 10 is a graph showing the levels of detection signals provided when a foreign particle and corners of the circuit pattern are detected.

Figure 4A:
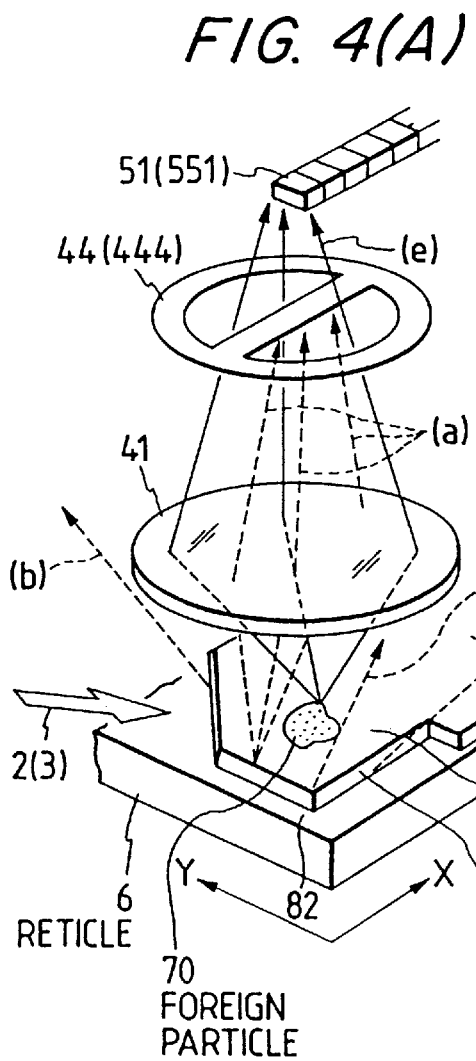
FIGS. 4(A), 4(B), 4(C) and 4(D) are views for assistance in explaining a reticle inspecting method in accordance with the present invention.
Figure 4B:
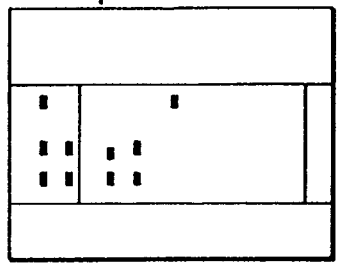

Shown in FIG. 4(A) are a foreign particle 70 on the reticle 6 fastened to the Z-stage 10 by the fastening device 18, a straight portion 81 of a circuit pattern 80, and a corner 82 of the circuit pattern 80.

The reticle 6 is illuminated obliquely by the illuminating unit 2 (or any one of the illuminating units 20, 3 and 30). Directly reflected light and directly transmitted light are not gathered. Only scattered light and diffracted light are gathered by the objective lens 41. Only the light diffracted by an edge of the circuit pattern 80 extending at an angle $\theta=0°$ to a direction perpendicular to the horizontal component 60 of the direction of travel of the illuminating light emitted by the illuminating unit 2 (or any one of the illuminating units 20, 3 and 30), which is called a 0-degree edge, is focused in a band as shown in FIG. 6(a) on the Fourier transform plane of the objective lens 41. The angle $\theta$ of the edges of the circuit pattern 80 is 0°, 45° or 90°. Light (b) diffracted by a 45-degree edge and light (c) diffracted by a 90-degree edge do not fall on the objective lens 41 as shown in FIG. 4(A) and do not affect the inspection of the reticle. Light scattered by the foreign matter 70 is scattered over the entire area of the Fourier transform plane as shown in FIG. 6(e). Therefore, the foreign matter 70 can be discriminated from the circuit pattern 80 by intercepting the light (a) diffracted by the 0-degree pattern shown in FIG. 4(A) by the spatial filters 44 and 44 disposed on the Fourier transform planes and each having a band-shaped screening portion and light-transmissive portions on the opposite sides of the opaque portion.

Thus, this detection optical system 4 has a large NA. When NA=0.5, the aperture area of the detection optical system 4 is about twenty times the aperture area of the conventional detection optical system having a small NA (NA=0.1). Light scattered by a corner portion (FIG. 4(D)) of the circuit pattern 80 cannot completely be intercepted by the linear spatial filter. Therefore, when $10\times20$ $\mu m^2$ detecting pixels are used for detection (FIG. 4(B)), light scattered by a plurality of corner portions fall on the pixels and the detection of only the foreign particle is impossible.

Figure 4C:
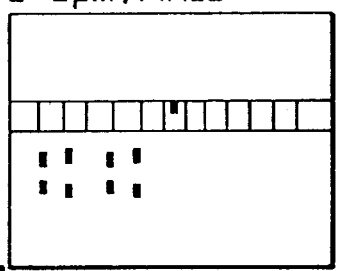
Figure 4D:
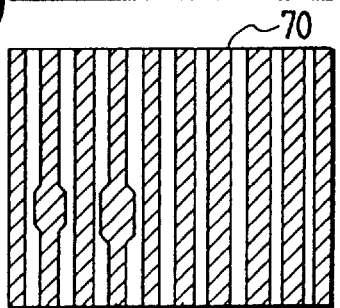

Accordingly, the present invention uses $2\times2$ $\mu m^2$ pixels for higher resolution (FIG. 4(C)) to eliminate the influence of the scattered light and diffracted light, which has been scattered and diffracted, respectively, by the circuit pattern 80, as perfectly as possible. The size of the pixels need not be necessarily $2\times2$ $\mu m^2$. The pixels may be of any size, provided that the size is smaller than the size L of the smallest portion of the circuit pattern 80. When the reticle is exposed by a stepper having a reduction ratio of ⅕ when fabricating a 0.8 $\mu m$ process LSI, pixels of $0.8\times5=4$ $\mu m^2$ or below serve the purpose, and pixels of $0.5\times5=2.5$ $\mu m^2$ or below serve the purpose when fabricating a 0.5 $\mu m$ process LSI.

Practically, the size of the pixels may be greater or smaller than the above-mentioned sizes as long as the pixels are able to reduce the influence of the light scattered by the corner portions of the circuit pattern to a negligibly small extent. Concretely, a desirable size of the pixels is nearly equal to the size of the smallest portion of the circuit pattern. When the size of the pixels is on the order of the size of the smallest portion of the circuit pattern, only less than two corner portions correspond to each pixel, and as is obvious from the results of experiment shown in FIG. 10, the size of the pixels is small enough. Pixels having a size in the range of 1 to 2 $\mu m^2$ are desirable for inspecting a reticle for fabricating a 64 MDRAM.

Since a corner 82 of the circuit pattern 80 shown in FIG. 7(A) has a continuously curved edge 820 as shown in FIG. 7(B), light (d) diffracted by the corner 82 is scattered on the Fourier transform planes as shown in FIG. 6(d) and the spatial filters 44 and 444 are unable to intercept the diffracted light (d) completely. Consequently, the output V of the detector 51 (551) increases as shown in FIG. 8 and the foreign matter 70 cannot be discriminated from the circuit pattern 80 if light diffracted by a plurality of corners 82 falls on the detector 51 (551). As shown in FIG. 8, the output 822 of the detector 51 (551) provided when a plurality of corners 82 are detected is higher than the output 821 of the same provided when a single corner 82 is detected. If the output of the detector 51 (551) is binarized by using a binarizing threshold 90 indicated by a dotted line, the output 701 of the detector 51 (551) representing the foreign particle 70 cannot be discriminated from the output 822 of the detector 51 (551) representing the plurality of corners 82.

To solve the problem described with reference to FIG. 8, the present invention forms an image of the inspection field 15 on the detectors 51 and 551 by means of the objective lens 41 and the focusing lenses 45, determines the sizes of the detectors 51 and 551 and the image forming magnification selectively to determine the size of the inspection field 15 (for example, 2 $\mu m \times 2$ $\mu m$) optionally in order to obviate the simultaneous incidence of light diffracted by a plurality of corners 82 on the detectors 51 and 551. However, this arrangement is not sufficiently effective to discriminate a foreign particle of a size in the submicron range from a corner 82 of the circuit pattern 80. Furthermore, since the behavior of light diffracted by a portion of a size 84 on the submicron order, which is smaller than the size 83 of other portions of the circuit pattern 80 as shown in FIG. 9, is similar to that of light scattered by the foreign particle 70, it is difficult to discriminate the foreign particle 70 from such a minute circuit pattern.

The reticle inspecting apparatus of the present invention is capable of detecting the foreign particle 70 in such a minute circuit pattern having portions of a size 84 in the submicron range. In FIG. 10, 701 and 702 indicate a detection signal provided upon the detection of light scattered by a minute foreign particle 70 of a size in the submicron range; 864, 874, 865, 875, 866, 876, 867 and 877 indicate detection signals provided upon the detection of light scattered by all the corners 82 of the 0-degree, 45-degree and 90-degree edges, and 861, 871, 862, 872, 863 and 873 indicate detection signals provided upon the detection of scattered light scattered by minute portions of sizes 84 in the submicron range. The detection signals 701, 861, 862, 863, 864, 865, 866 and 867 are provided by the detector when the illuminating light beam projected by the first front illuminating unit 2 (or the first back illuminating unit 3) and scattered by the minute circuit pattern is detected, and the detection signals 702, 871, 872, 873, 874, 875, 876 and 877 are provided by the detector when the illuminating light beam projected by the second front illuminating unit 20 (or the second back illuminating unit 30) and scattered by the minute circuit pattern is detected. For example, the detection signals 861←→871 are those provided when the illuminating light beam projected by the first front illuminating unit 2 (or the first back illuminating unit 3) and scattered by a portion of the minute circuit pattern is detected by the detector and when the illuminating light beam projected by the second front illuminating unit 20 (or the second back illuminating unit 30) and scattered by the same portion of the minute circuit pattern is detected by the detector, respectively. As is obvious from FIG. 10, the value of the detection signal provided upon the detection of the foreign particle 70 is less dependent on the direction of projection of the illuminating light beam than that of the detection signal provided upon the detection of a portion of the minute circuit pattern. In FIG. 10, a dotted line 91 represents the threshold for binarization.

As is obvious from FIG. 10, the value of the detection signal provided by the detector upon the detection of a portion of the minute circuit pattern is greatly dependent on the direction of projection of the illuminating light beam; and, when a portion of the surface of the reticle 6 is illuminated obliquely by two illuminating light beams which travel respectively along paths which are symmetrical with respect to a normal to the surface of the reticle 6 at the illuminated portion, either of the detection signals provided upon the detection of the two illuminating light beams scattered by the illuminated portion is necessarily smaller than the detection signal provided upon the detection of the light scattered by the foreign particle of a size in the submicron range, as indicated by the solid circles. When the illuminating light beams are projected obliquely by both the first front illuminating unit 2 and the second front illuminating unit 20, which are disposed symmetrically with respect to a normal to the surface of the reticle 6 at the illuminated position, or by both the first back illuminating unit 3 and the second back illuminating unit 30, which are disposed symmetrically with respect to a normal to the surface of the reticle 6 at the illuminated position, the detection signal is the sum of the detection signal provided upon the detection of the scattered illuminating beam projected by one of the two front (back) illuminating units and scattered by the foreign particle, or a portion of the circuit pattern, and the detection signal provided upon the detection of the scattered illuminating beam projected by the other front (back) illuminating unit and scattered by the same foreign particle, or the same portion of the circuit pattern. Thus, the foreign particle can be illuminated with an illuminance higher than an illuminance to which the circuit pattern is illuminated, whereby the foreign particle 70 of a size in the submicron range can be discriminated from the circuit pattern 80.

When the light scattered by the foreign particle 70 is detected, the microcomputer 54 stores foreign particle data, including information about the respective positions of the X-stage 10 and the Y-stage 11, information about the position of the foreign particle 70 calculated on the basis of the position of the corresponding pixel, and the detection signals of the detectors 51 and 551, in a storage device, and displays the foreign particle data on the display 55, such as a CRT.

Figure 17:
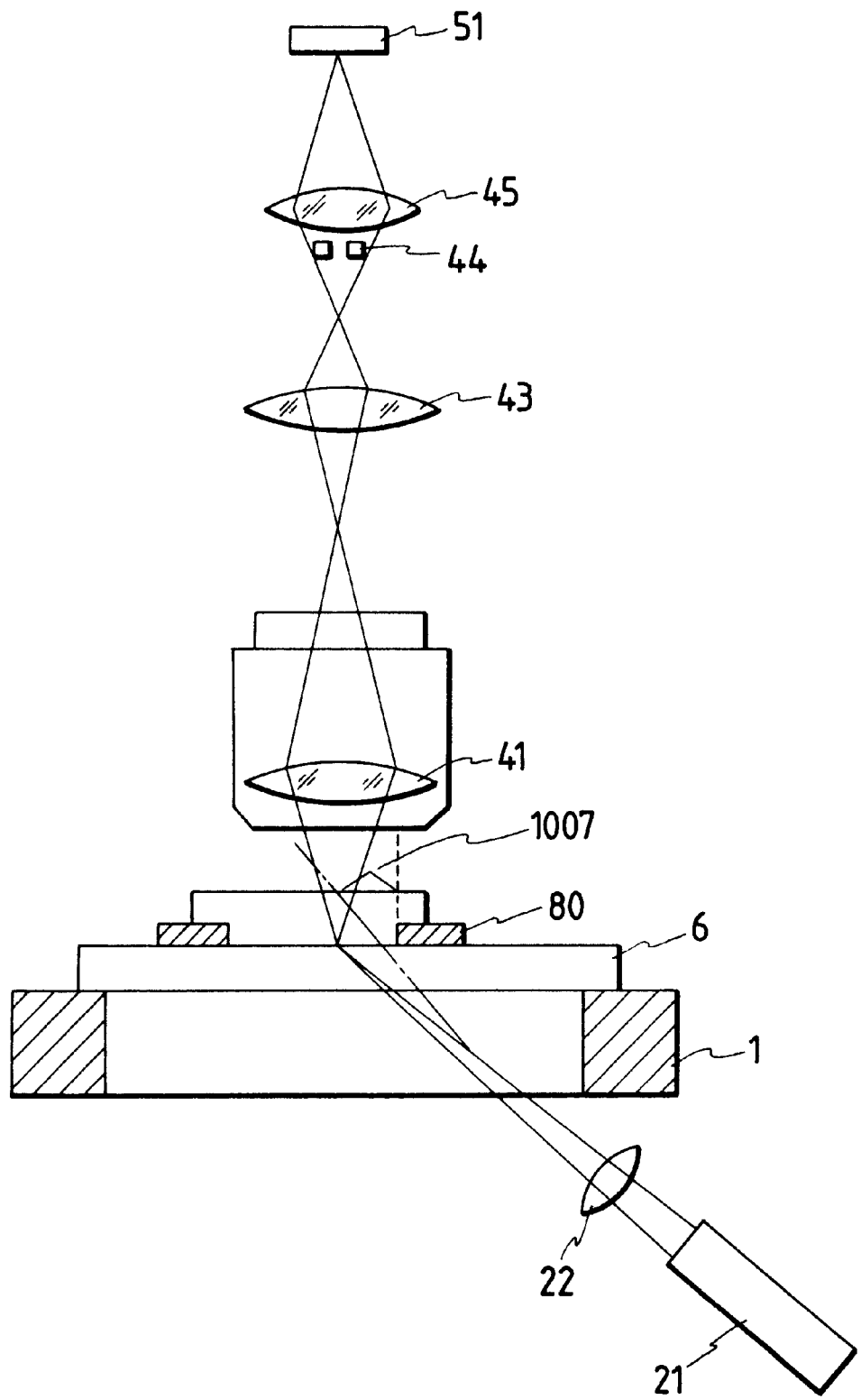
FIG. 17 is a diagrammatic view showing the configuration of a reticle inspecting apparatus embodying the present invention.
Figure 34:
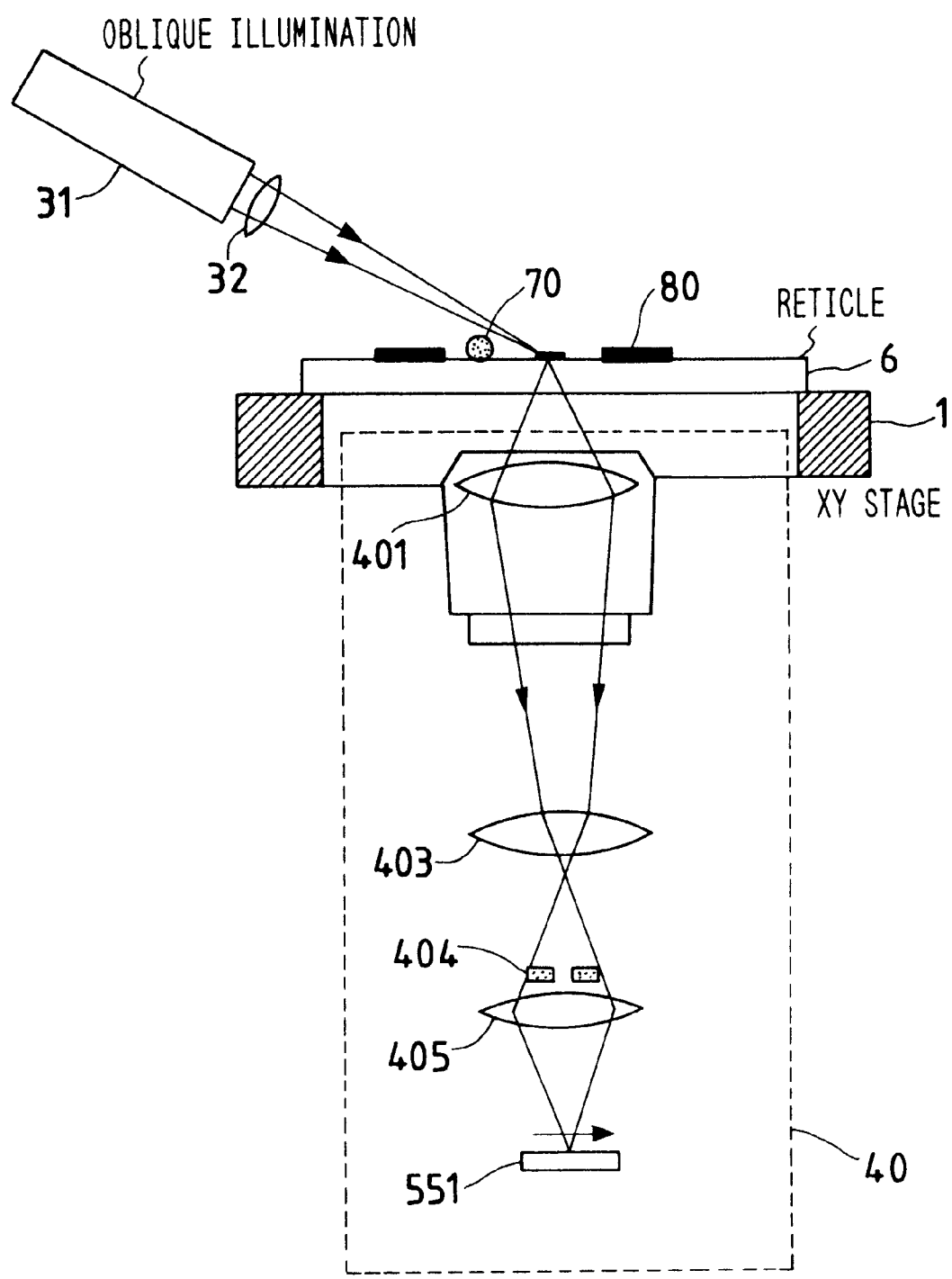
FIG. 34 is a diagrammatic view for a reticle inspecting apparatus in a second embodiment according to the present invention.

FIG. 17 shows a reticle inspecting apparatus of the back illuminating unit. The respective positions of an illuminating unit 3 and a detection optical system 4 included in the reticle inspecting apparatus may be interchanged with respect to the reticle 6. FIG. 34 shows another reticle inspecting apparatus of the back illuminating unit, in which the respective positions of an illuminating unit 31 and a detection optical unit 40 with respect to the reticle 6 are reverse to those of the illuminating unit 3 and the detection optical system 4 of the reticle inspecting apparatus of FIG. 17. The reticle inspecting apparatus of FIG. 17 detects light scattered by a foreign particle on the transparent substrate of the reticle 6, and the reticle inspecting apparatus of FIG. 34 detects light scattered by a foreign particle and transmitted through the transparent substrate of the reticle 6. When the scattered light is transmitted through the transparent substrate of the reticle 6, as in the reticle inspecting apparatus of FIG. 34, the resolution is deteriorated by aberration caused by the substrate of the reticle 6, which makes the stable detection of the foreign particle difficult. Therefore, the image forming optical system of the reticle inspecting apparatus of FIG. 34 needs to be provided with a lens capable of compensating the aberration caused by the substrate of the reticle 6.

Figure 35:
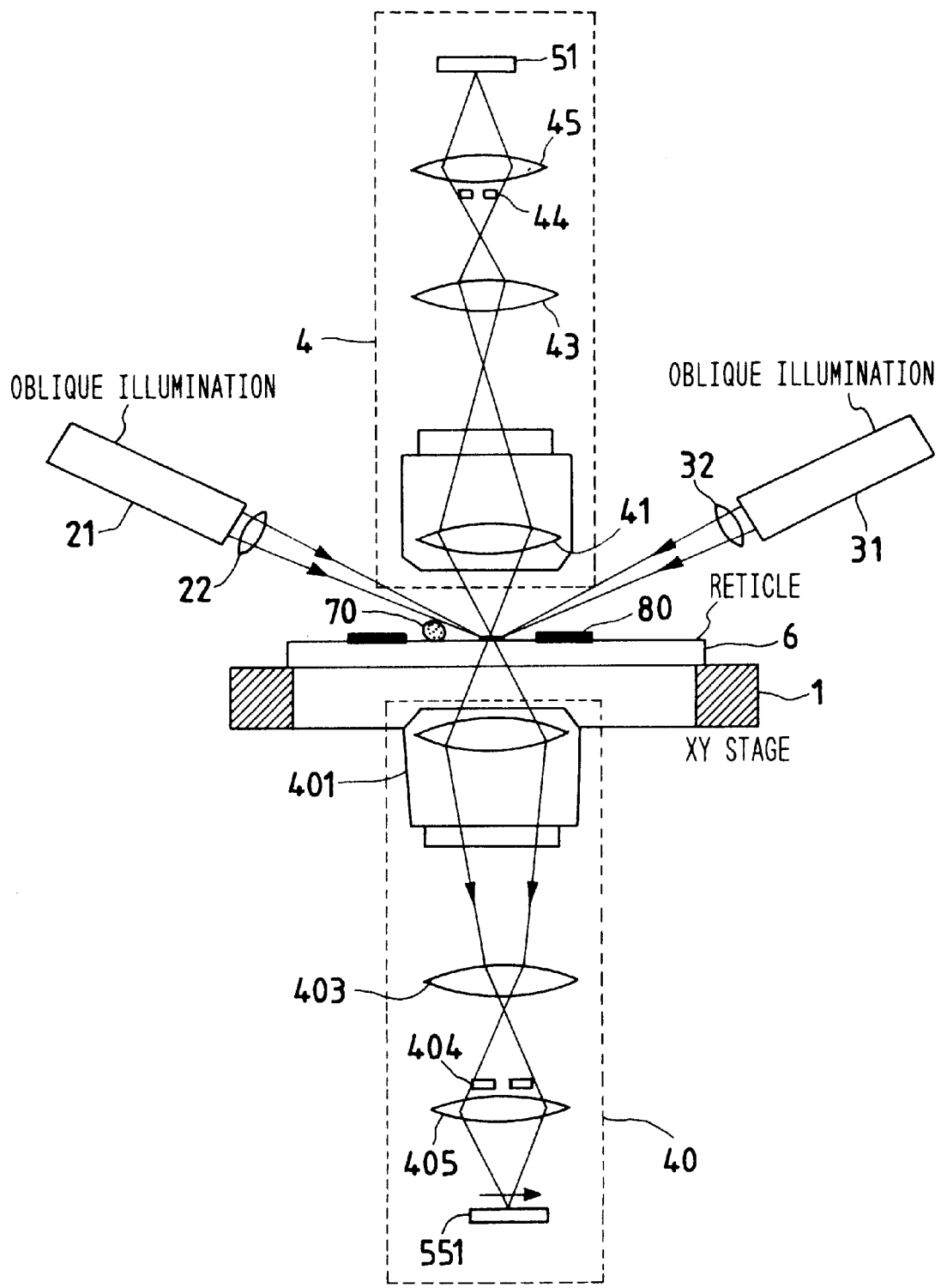
FIG. 35 is a diagrammatic view of a reticle inspective apparatus in a third embodiment according to the present invention.

The reticle inspecting apparatus shown in FIG. 35 is analogous to the reticle inspecting apparatus shown in FIG. 34 in configuration. The reticle inspecting apparatus of FIG. 35 is suitable for inspecting the entire surface of the reticle 6. The reticle inspecting apparatus shown in FIG. 35 comprises a first front illuminating unit 21 and a second front illuminating unit 31, which are disposed on the side of the front surface of the reticle 6, a front detection optical system 4 disposed on the side of the front surface of the reticle 6, and a back detection optical system 40 disposed on the side of the back surface of the reticle 6. The front detection optical system 4 detects light scattered by opaque portions of the reticle 6, i.e., reflected light, and the back detection optical system 40 detects light scattered by light-transmissive portions of the reticle 6, i.e., transmitted light. The front detection optical system 4 and the back detection optical system 40 must be provided respectively with appropriate wavelength filters to detect only reflected light and only transmitted light, respectively.

Foreign particles on the chromium pattern, i.e., the opaque film, of the reticle do not cause defects when an image of the reticle is printed by a photographic process. Foreign particles on exposed portions of the glass substrate cause defects in a photographically printed image of the reticle. Accordingly, foreign particles which may migrate from the chromium pattern to positions outside the chromium pattern, i.e. migratory foreign particles, must be detected. The mobility of foreign particles will be described hereinafter. According to various literature on the mobility of particles, such as Mittal, "Particles on Surface", pp. 129–141, three kinds of forces are to be considered, i.e., a van der Waals force, an electrostatic force and an inertial force. The van der Waals force is an attractive force that attracts a foreign particle to the substrate; the electrostatic force is an attractive force or a repulsive force; and, the inertial force acts on a foreign particle in a direction corresponding to the direction of an acceleration that acts on the foreign particle. When the electrostatic force is on the order of $1/10$ of the dielectric strength of air and the gravitational acceleration is acting on the foreign particle, the van der Waals force is dominant, and the smaller the foreign particle, the more dominant will be the van der Waals force. The foreign particle is supposed to be moved by acceleration (shock) that acts on the reticle during transportation. Therefore, the smaller the foreign particle, the less will be the possibility of migration of the foreign particle.

From the foregoing, the electrostatic force is $1/10^2$ of the van der Waals force and the inertial force is $1/10^6$ of the van der Waals force, if the size of the foreign particle is 1.0 μm; that is, an acceleration 106 times the gravitational acceleration must be applied to the 1.0 μm foreign particle to move the foreign particle. Practically, such a high acceleration never acts on the foreign particle and hence foreign particles of sizes less than 1.0 μm will not move. Thus, the ability to detect foreign particles having sizes not smaller than 1.0 μm on the chromium pattern is sufficient for detecting practically detrimental foreign particles.

The detection of foreign particles on the chromium pattern is important for the following purposes in addition to the detection of migratory foreign particles. In some cases, foreign particles on the chromium pattern cause problems when fabricating a reticle provided with a phase shifter. Generally, a reticle provided with a phase shifter is fabricated by the steps of forming a chromium pattern on a substrate, forming a phase shift film over the entire surface of the substrate by coating or sputtering, and etching the phase shift film in a desired shifter pattern to complete a phase shifter. If there are foreign particles on the chromium pattern before forming the phase shift film, defects, such as bubbles and cracks, will be formed in the phase shift film, and will cause defects in a printed image of the reticle. Accordingly, it is necessary to inspect the entire surface of the substrate before and after the formation of the shifter film for defects, including cracks, bubbles and irregularities in addition to the inspection after the formation of the shifter pattern. The reticle inspecting apparatus in accordance with the present invention is capable of detecting such defects, as well as foreign particles. When inspecting the surface of the substrate before forming the shifter pattern, the reticle inspecting apparatus as shown in FIG. 1 is used for the detection of defects with a high sensitivity because there is no light scattered by the shifter pattern.

The reticle inspecting apparatus shown in FIG. 17 or FIG. 34 is applicable to the inspection of a transparent (or translucent) substrate provided with an opaque film before patterning the opaque film. Since there is no light scattered by a circuit pattern, the spatial filter 44 may be omitted. The detection signal provided upon the detection of the forward scattered light component of the light scattered by a foreign particle in this mode is higher than that provided upon the detection of light reflected by the same foreign particle. When the spatial filter 44 is omitted, the reticle may be scanned in either an XY scanning mode or a rotary scanning mode.

Detection and identification of a foreign particle on the basis of the output of each pixel of a detector of the array type entails the following problems.

Figure 26:
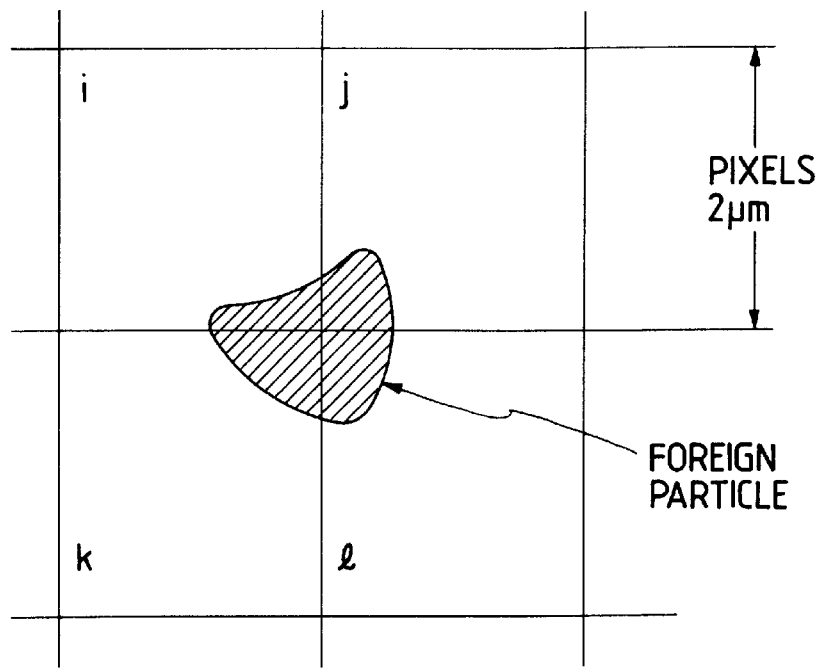
FIG. 26 is a diagrammatic view for assistance in explaining the detection of a foreign particle by a process using a 2×2 $\mu$m pixel instead of a four-pixel addition process.

Suppose that a detector having pixels, of 2×2 $\mu m^2$ is used for the detection and identification of a foreign particle. Then, if the foreign particle is detected by four pixels, as shown in FIG. 26, the light scattered by the foreign particle is distributed to the plurality of pixels and the output of each pixel is in the range of ½ to ¼ (practically about ⅓ due to crosstalk between the pixels) of the output which may be obtained when the foreign particle is detected by a single pixel; and, consequently, the detection probability is reduced. Furthermore, the positional relation between the pixels of the detector and the minute foreign particle is delicate and very liable to change every time the inspection is made, which deteriorate the repeatability of the inspection. Such problems arise also when the foreign particle is detected by two pixels or three pixels, as well as when the foreign particle is detected by four pixels.

Figure 27:
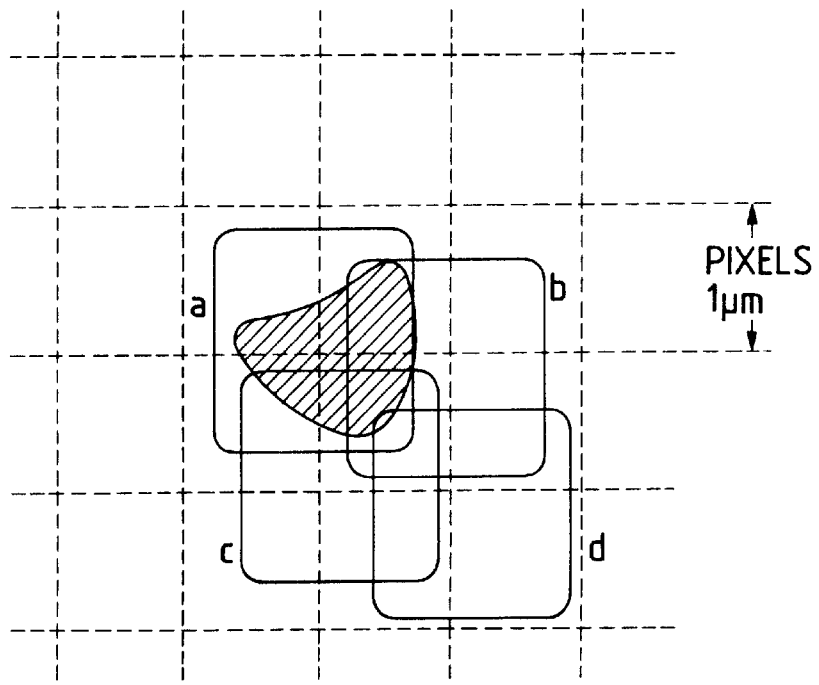
FIG. 27 is a diagrammatic view for assistance in explaining the detection of a foreign particle by a four-pixel addition process using 1×1 $\mu$m pixels.

To overcome the foregoing disadvantage, 1×1 $\mu m^2$ pixels as shown in FIG. 27 are used, and the respective detection signals provided by the four adjacent 1×1 $\mu m^2$ pixels are added electrically to simulate the detection signal of a 2×2 $\mu m^2$ pixel. The sums of the detection signals, each of four adjacent pixels of each of four duplicate pixel groups a, b, c and d, are calculated, and the maximum sum of outputs, i.e., the sum of outputs of the pixels of the pixel group a in FIG. 27, is considered to be equivalent to the output of a 2×2 $\mu m^2$ pixel and is used as a foreign particle detection signal. In this method of detecting a foreign particle, the variation of the detection signal indicating a foreign particle is within ±10% and the repeatability of detection for all the foreign particles is 80% or above.

Figure 28:
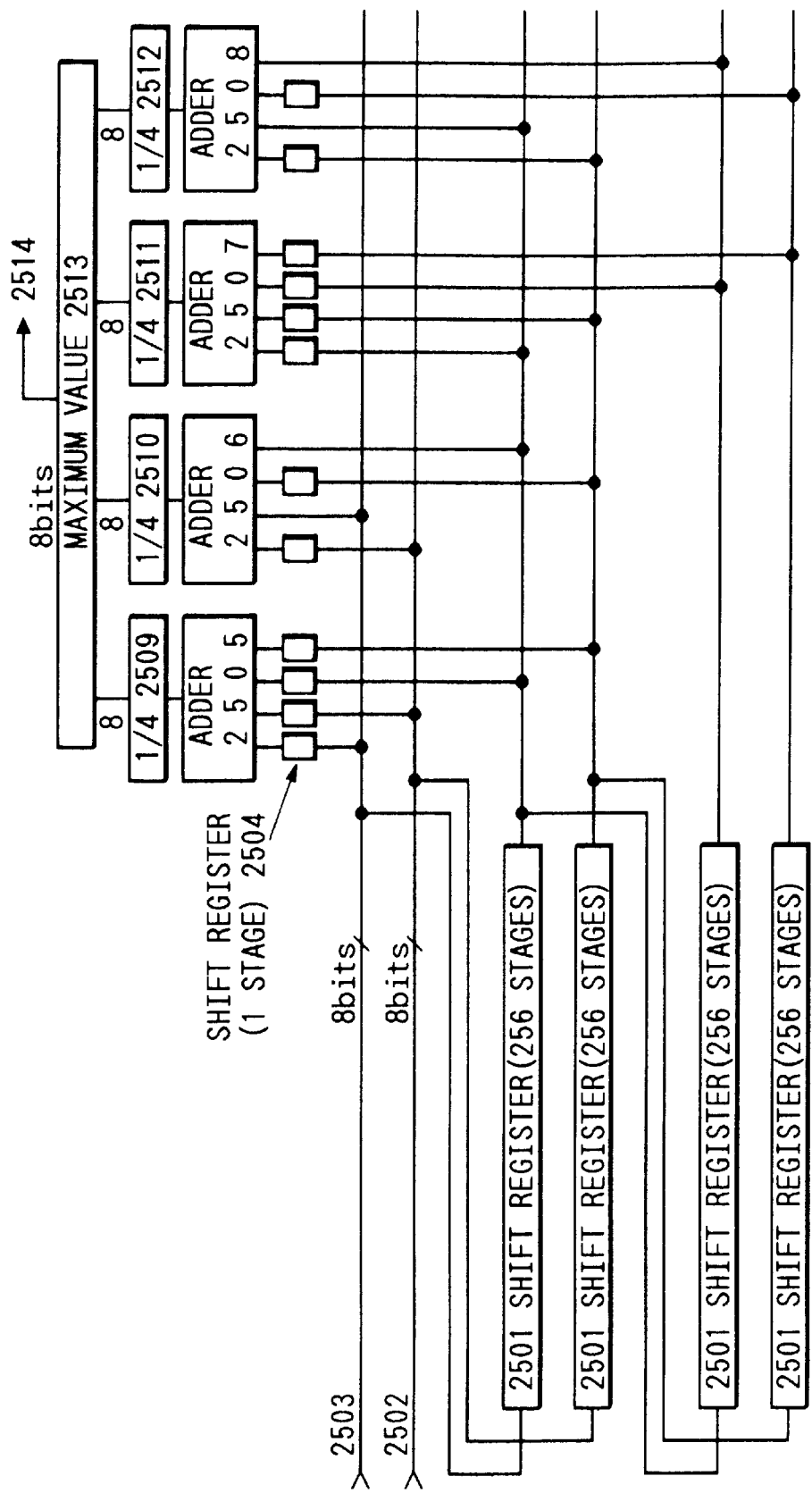
FIG. 28 is a block diagram of a four-pixel addition circuit.

FIG. 28 is a block diagram of a four-pixel addition circuit. This four-pixel addition circuit is used in combination with a one-dimensional imaging device provided with an array of 512 1 $\mu m^2$ pixels, which provides the output 2502 of even-numbered pixels and the output 2503 of odd-numbered pixels provided separately. The outputs of four 1×1 $\mu m^2$ pixels (2×2 pixels) shifted by one pixel in four directions are added by 256-stage shift registers 2501, one-stage shift registers 2504 and adders 2505 to 2508, and dividers 2509 to 2512 calculate the mean values of the outputs of the pixels. A maximum value selecting circuit 2513 selects the maximum mean value as a foreign particle detection signal 2514 from among the four mean values.

Figure 29:
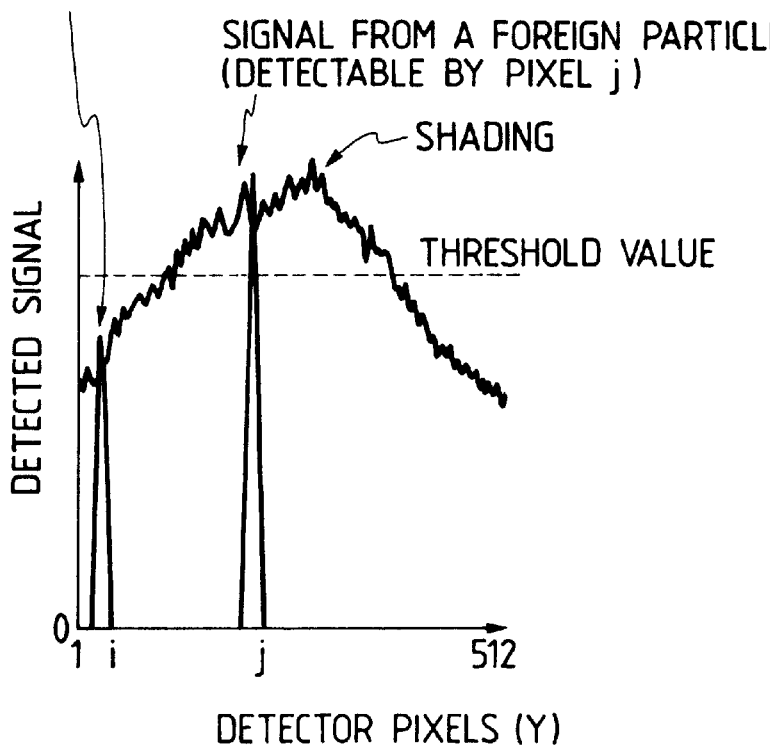
FIG. 29 is a graph for assistance in explaining the effect of shading on the detection of foreign particles.

The reticle inspecting apparatus of the present invention actualizes only foreign particles optically for detection, and binarizes the detection signal when the detection signal is greater than the threshold to detect a foreign particle. However, the detection signal is subject to change due to (1) the difference between the pixels in sensitivity (about ±15%) and (2) the difference between the pixels in output level attributable to the distribution of illuminance on the reticle (shading). Therefore, the different pixels provide different detection signals for the same foreign particle, as shown in FIG. 29, and the level of the output signal is dependent on the position of the pixel with respect to the direction along the Y-axis. Thus, it is impossible to detect a foreign particle stably through the binarization of the detection signal exceeding the threshold.

Figure 30A:
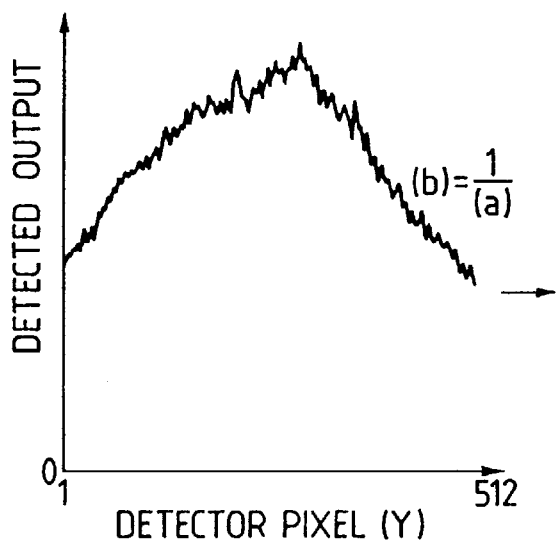
FIGS. 30(a), 30(b) and 30(c) are graphs for assistance in explaining the principle of shading, showing measured data of shading as measured, compensated data of shading and compensated measured data of shading, respectively.
Figure 30B:
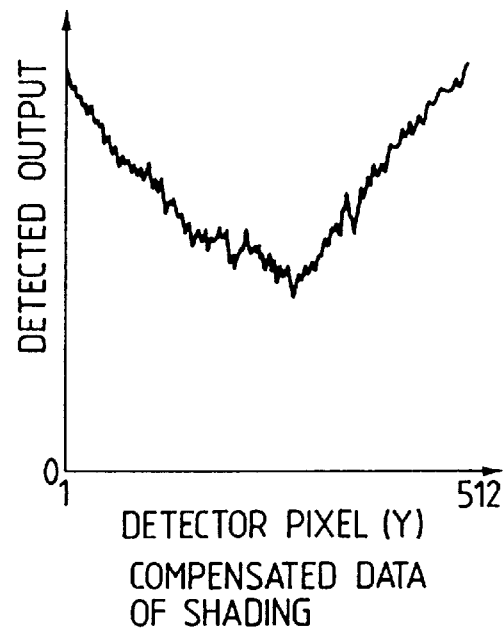

The present invention measures the shading effect of the causes (1) and (2) (FIG. 30(*a*)) beforehand by using a standard reticle 111 (FIG. 1), calculates the reciprocal of the measured shading effect to determine shading compensating data (FIG. 30(*b*)) and controls the gain of an amplifier for amplifying the detection signal of the detector for the respective outputs of the pixels to obtain compensated outputs of the pixels (FIG. 30(*c*)) to eliminate the influence of the shading effect. The standard reticle 111 may be mounted on or disposed near the Z-stage 10 of the inspection stage unit 1, or may be mounted on the Z-stage only when measuring the shading effect.

The standard reticle 111 has a surface having minute irregularities and a uniform scattering characteristic. For example, the standard reticle 111 may be a glass plate having a surface having minute irregularities formed by grinding, a glass plate having a surface to which standard particles of a specific size are attached uniformly or a plate provided with an aluminum film formed by sputtering. Practically, it is difficult to form minute irregularities corresponding to a 1×1 $\mu m^2$ pixel uniformly for the standard reticle 111. Therefore, the shading effect measurement is repeated many times, for example 1000 times and determines the compensated data on the basis of the mean value of the measured data.

Since only portions of the surface of the standard reticle 111 having minute irregularities scatter light and light is not scattered by the entire surface of the standard reticle 111, the addition of measured values obtained by repeating the measurement 1000 times is not equivalent to, and is far smaller than, the addition of 1000 distributions of illuminance over the entire illuminated area of the surface of the standard reticle 111. Therefore the simple mean value, such as the mean values of measured data obtained by dividing the sum of measured data by the number of the repetitions of the measurement, is excessively small for accurate calculation. Under such a condition, the mean value may be determined by dividing the sum of the measured data by a divisor, for example, 200, which is a fraction of the number of the repetitions of the measurement, for example, 1000.

Figure 30C:
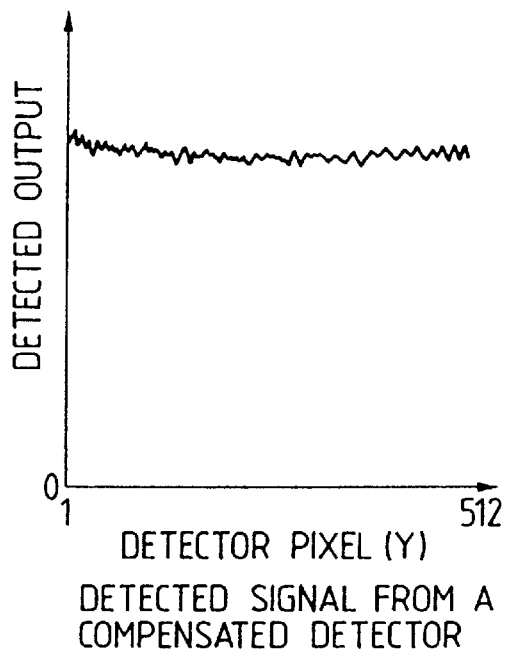

As is obvious from a comparative examination of FIGS. 30(a) and 30(c), the shading of about 50% (FIG. 30(a)) is reduced to 5% or below by correction. The adverse effect of the optical components of causes of variation in the compensated data attributable to the time-dependent variation of the performance of the illuminating system and the detection optical system can be eliminated by determining and renewing the compensated data every time the inspection is performed.

Figure 31:
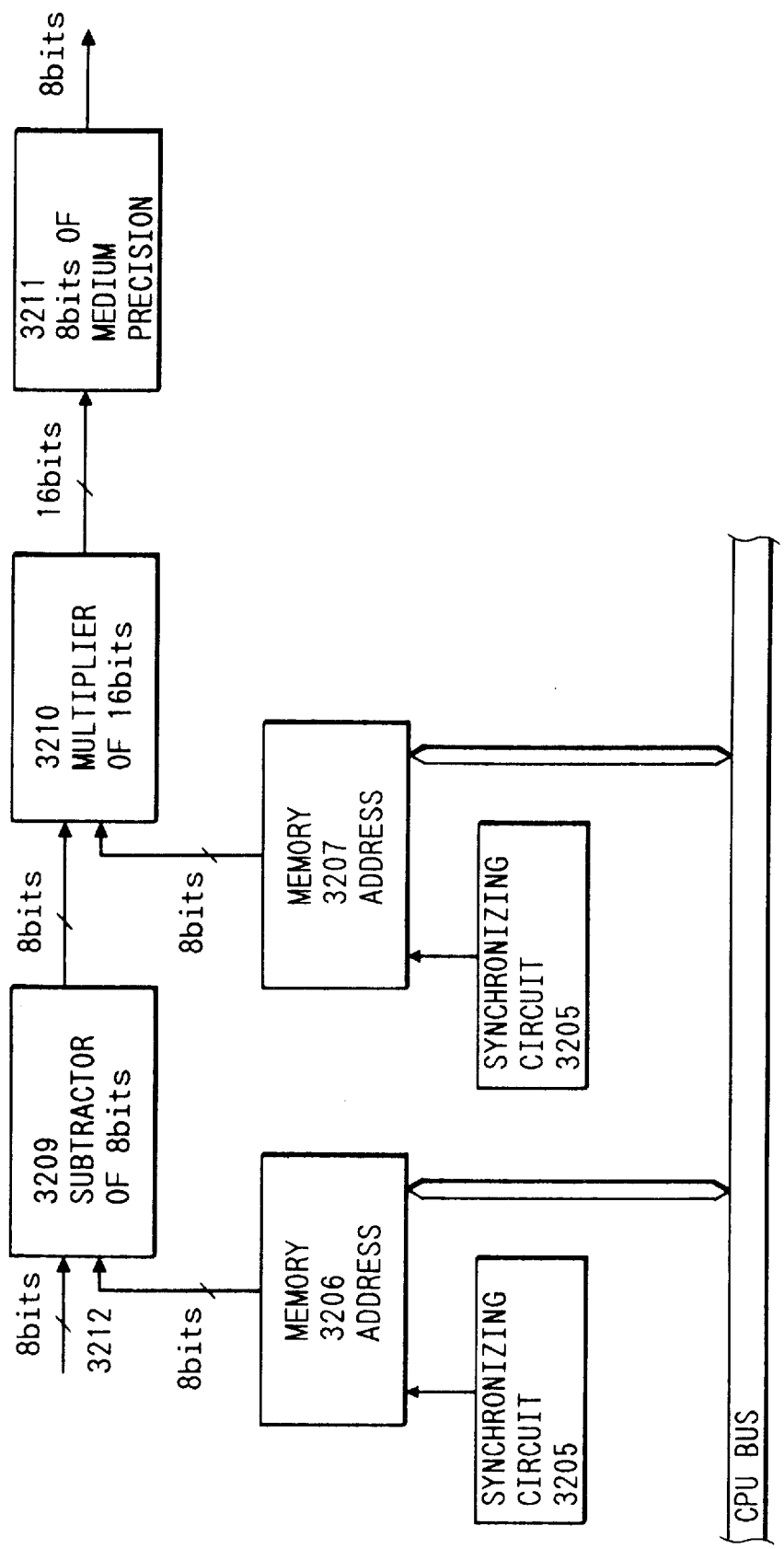
FIG. 31 is a block diagram of a shading compensating circuit.

As shown in FIG. 31, a shading compensating circuit for compensating shading comprises a subtracter 3209, which subtracts data representing the dark current of each pixel and read from a memory 3206 controlled by a synchronizing circuit 3205 from an 8-bit value 3212 (256 steps) obtained through the A/D conversion of a detection signal provided by the one-dimensional imaging device; a multiplier 3210, which multiplies a shading compensation factor by data for each pixel read from a memory 3207 controlled by a synchronizing circuit 3205; and a medium bit signal output circuit 3211, which changes the number of bits of a calculated 16-bit value, which is twice the number of bits, i.e., eight bits, of the 8-bit value 3212 obtained through the A/D conversion of the detection signal provided by the one-dimensional imaging device, for the initial number of bits, i.e., eight bits. Although this shading compensating circuit is a digital circuit that deals with digital values, analog data may be used for compensation.

If 2×2 $\mu m^2$ pixels are used for detecting foreign particles having sizes greater than 2 $\mu m$, the number of pixels used for detecting the foreign particles will not be equal to the actual number of pixels representing the detected foreign particles. When 2×2 $\mu m^2$ pixels are used for detecting a foreign particle of 10 $\mu m$, twenty-five pixels ($10^2/^2=25$) will provide detection signals and the twenty-five detection signals must be examined to observe the detected foreign particle.

The conventional reticle inspecting method examines the positional relation between the pixels which have detected foreign particles by software and decides that one foreign particle is detected by grouping pixels, when the pixels which have detected foreign particles are adjacent pixels, to avoid the necessity of examining so many detection signals. This conventional method, however, needs software processing and requires much time for processing many detection signals, for example, about ten minutes for processing 1000 detection signals.

The present invention divides the entire inspection region into a plurality of field blocks (blocking) which can be simultaneously observed, such as field blocks each of 32×32 $\mu m^2$, and regards all the detection signals corresponding to each field block as detection signals obtained by detecting one and the same foreign particle. Thus, even a large foreign particle can be caught in the field block for observation regardless of its shape.

Although blocking is functionally equivalent to grouping, blocking can be easily achieved by hardware. The present invention carries out blocking in a real-time mode by hardware, reduces the inspection time and enhances the throughput of the reticle inspecting apparatus. The reticle inspecting apparatus of the present invention is able to examine 1000 detection signals in ⅔ times the time required by the conventional reticle inspecting apparatus.

Figure 32:
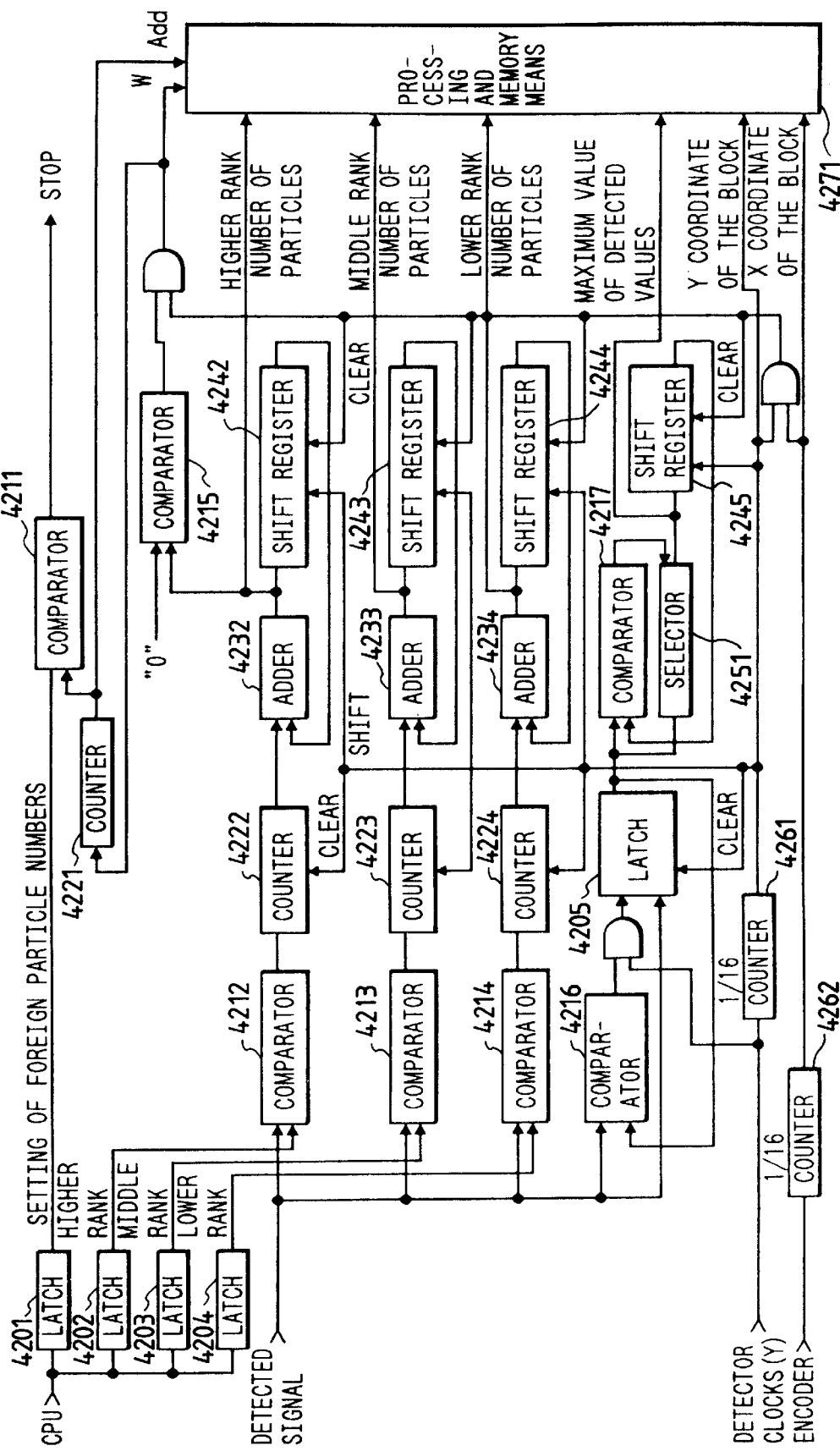
FIG. 32 is a block diagram of a block processing circuit.

Referring to FIG. 32, a blocking circuit classifies detection signals provided by the detector according to magnitude into detection signals of three ranks, namely, those of a large rank (large foreign particle detection signals) corresponding to large foreign particles, those of a medium rank (medium foreign particle detection signals) corresponding to medium foreign particles and those of a small rank (small foreign particle detection signals) corresponding to small foreign particles; counts the respective numbers of large foreign particle detection signals, medium foreign particle detection signals and small foreign particle detection signals in each pixel block of 256 pixels (=16×16 pixels); and, only when the number of foreign particles in each pixel block is 1 or above, writes the respective numbers of the large, medium and small foreign particles included in each pixel block, the maximum detection signal among those provided by the pixels of each block and the coordinates of each block in a storage device.

A CPU sets a latch 4201 to a maximum number of foreign particles as an upper limit number of foreign particles to be detected. If the number of foreign particles exceeds the maximum number, the inspection is interrupted because the further inspection of a reticle having so many foreign particles is unnecesary. A counter counts the number of detected foreign particles and a comparator 4211 compares the count of the counter 4221 with the maximum number to which the latch 4201 is set. If the count of the counter 4221 is greater than the maximum number, the inspection is interrupted.

The CPU sets a latch 4202 to a high threshold for discriminating detection signals indicating large foreign particles from those indicating medium and small foreign particles. When the level of a detection signal is higher than the high threshold, it is decided that the detection signal indicates the detection of a large foreign particle. A comparator 4212 compares the detection signal with the threshold; and, if the detection signal is higher than the threshold, the count of a counter 4222 for counting the number of large foreign particles is incremented by one.

The CPU sets a latch 4203 to a medium threshold for discriminating detection signals indicating medium foreign particles from those indicating small foreign particles. A comparator 4213 compares a detection signal with the medium threshold; and, if the detection signal is higher than the medium threshold, it is decided that the detection signal indicates a medium foreign particle, and the count of a counter 4223 is incremented by one.

The CPU sets a latch 4204 to a low threshold for discriminating detection signals indicating small foreign particles from those indicating matters other than foreign particles. A comparator 4214 compares a detection signal with the low threshold; and, if the detection signal is higher than the low threshold, it is decided that the detection signal indicates a small foreign particle, and the count of a counter 4224 is incremented by one.

In the foregoing foreign particle counting operation, the number of large particles is counted by all the counters, namely, the counter 4222 for counting large foreign particles, the counter 4223 for counting medium foreign particles and the counter 4224 for counting small foreign particles; and, the number of medium foreign particles is counted by both the counter 4223 for counting medium foreign particles and the counter 4224 for counting small foreign particles. Accordingly, the number of small foreign particles is determined by subtracting the number of medium foreign particles from the output of the counter 4224 for counting small foreign particles, and the number of medium particles is determined by subtracting the number of large foreign particles from the output of the counter 4223 for counting medium foreign particles. The respective numbers of large foreign particles, medium foreign particles and small foreign particles may be determined when displaying or otherwise providing the result of inspection. The detection signals may be compared by two comparators to discriminate between detection signals indicating large, medium and small foreign particles. For example, only detection signals between a high threshold for large foreign particles and a medium threshold for medium foreign particles are selected as those indicating medium foreign particles, and only detection signals between the medium threshold and a low threshold for small foreign particles are selected as those indicating small foreign particles.

Adders 4232, 4233 and 4234, and shift registers 4242, 4243 and 4244 block the array of one-dimensional detector, such as a CCD detector, into two-dimensional blocks, each of, for example, 16×16=256 pixels. The number of steps of the shift register is equal to (The number of pixels of the CCD array)/(The number of pixels on one side of the block). In this case, the number of pixels of the CCD array is 256 and the number of pixels on one side of the block is 16; and hence, the number of steps of the shift register is 256/16=16. Although the number of steps of the shift register is equal to the number of pixels on one side of the block in this example, the coincidence of those numbers is an accident and the number of steps of the register and that of the pixels on one side of the block need not necessarily be equal to each other. However, if the value of (The number of pixels of the CCD array)/(The number of pixels on one side of the block) is not an integer, a blocking circuit having a complex configuration is necessary. Therefore, it is desirable to determine the number of pixels of the CCD array and the number of pixels on one side of the block so that the value of (The number of pixels of the CCD array)/(The number of pixels on one side of the block) is an integer.

The contents of the counter 4222 for counting the number of large foreign particles is cleared (reset to zero) every time detection signals provided by the pixels on one side of each block (sixteen pixels) are counted. A clear signal is obtained by dividing a clock which is provided for each of the pixels arranged along the Y-axis of the detector by sixteen by means of a frequency divider (counter) 4261. In this case, a transfer clock of the CCD array may be used as the clock for each of the pixels arranged along the Y-axis. The count of the counter 4222 immediately before clearing, i.e., the count of detection signals for the sixteen pixels arranged along the Y-axis, is added to a value that appears at the output terminal of the 16-step shift register 4242 for large foreign particles by the adder 4232, and the output signal of the adder 4232 is applied to the input terminal of the 16-step shift register 4242 for large foreign particles. Then, the content of the 16-step shift register 4242 is shifted by one step by the clear signal obtained by dividing the clock that is provided for each of the sixteen pixels arranged along the Y-axis. Therefore, the content of the 16-step shift register 4242 is shifted by one step for every sixteen pixels arranged along the Y-axis. The content of the 16-step shift register 4242 appears at the output terminal every time the content of the same is shifted by sixteen steps. At this time, the CCD array is shifted a distance corresponding to one pixel along the X-axis, and the number of large foreign particles detected by the sixteen pixels arranged along the Y-axis is added to the content of the 16-step shift register 4242 by the adder 4232. The content of the 16-step shift register 4242 is cleared by a signal obtained by dividing a pulse provided by an encoder provided every time the CCD array is shifted a distance corresponding to one pixel along the X-axis by sixteen by means of a frequency divider (counter) 4262; that is, the content of the 16-step shift register 4242 is cleared every time the CCD array is shifted a distance corresponding to sixteen pixels arranged along the X-axis. Accordingly, the content of the 16-step shift register 4242 for large foreign particles corresponds to the number of large particles detected by the 16×16=256 pixels. When a comparator 4215 decides that the number of large foreign particles is not zero, a signal representing the number of foreign particles and the coordinates of the block are given to a processing and memory means 4271, in which the number of foreign particles represented by the count of the counter 4224 is equal to the sum of the respective numbers of detected large, medium and small foreign particles. Modes of operation of the blocking circuit for medium foreign particles and for small foreign particles are the same as that for large foreign particles described above.

A circuit for selecting the maximum detection signal from among those included in each block processes 16×16=256 pixels by a maximum detection signal selecting procedure, which is the same as the foreign particle counting procedure for counting the number of detected foreign particles, except that the former procedure uses a latch 4205 for holding the maximum detection signal provided by one of the sixteen pixels arranged along the Y-axis instead of the latches 4201, 4202 and 4203 and the counters 4222, 4223 and 4224, and a comparator 4217 and a selector 4251 instead of the adders 4232, 4233 and 4234, by using a clear signal for sixteen pixels arranged along the Y-axis, and a 16-step shift register 4245.

Figure 33:
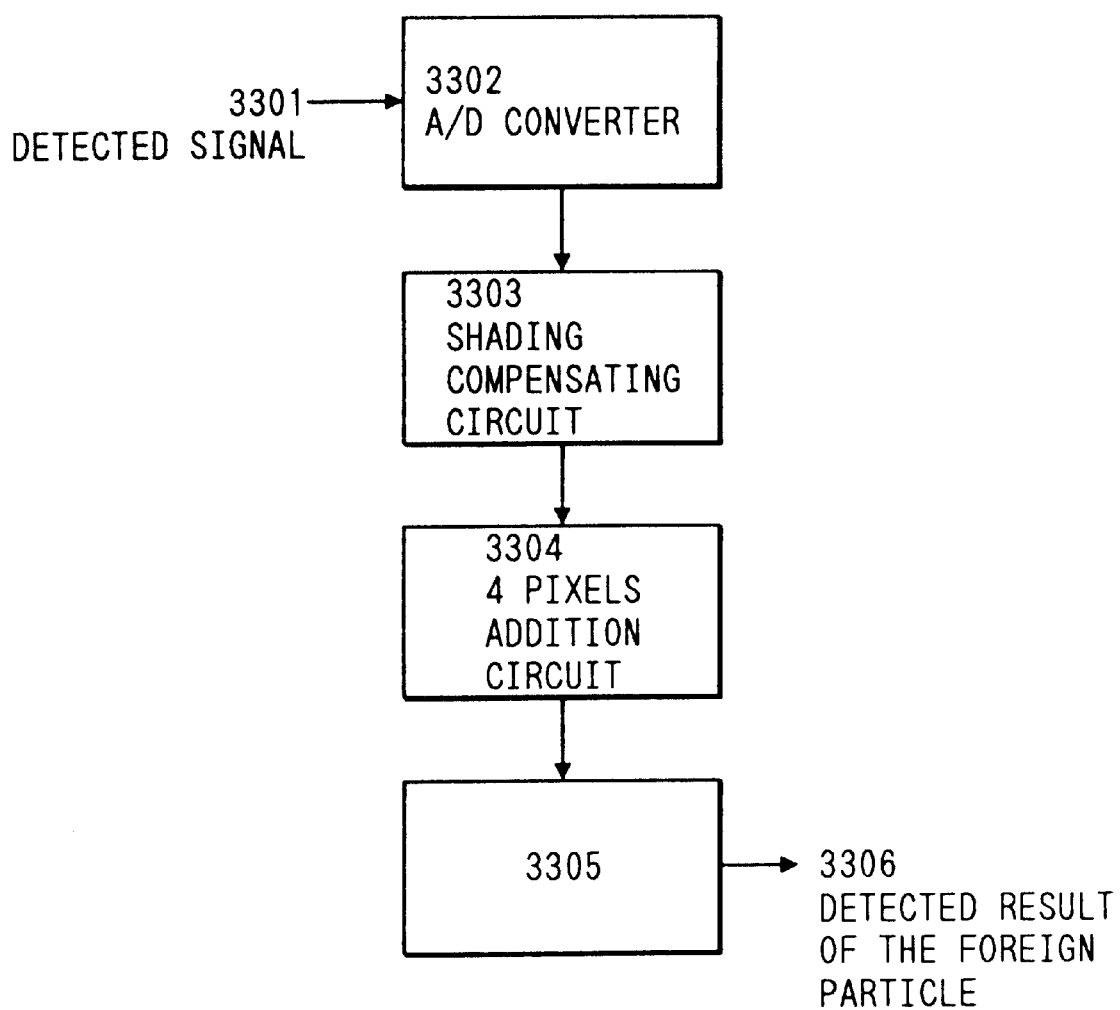
FIG. 33 is a block diagram showing the functional relation between a shading compensating circuit, a four-pixel addition circuit and a block processing circuit.

FIG. 33 shows the functional relation between an A/D converter 3302, a shading compensating circuit 3303, a 4-pixel addition circuit 3304 and a blocking circuit 3305. In FIG. 33 indicated at 3301 is a detection signal and at 3306 is the result of foreign particle detection.

The variable spatial filter 44 (444) will be described concretely hereinafter.

Figure 37:
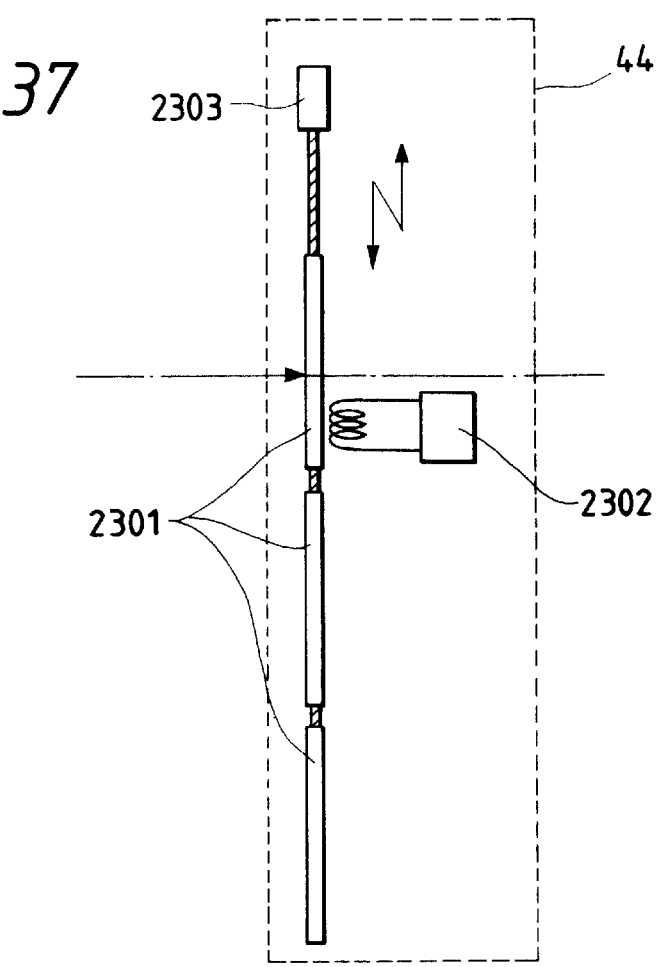
FIG. 37 is a schematic side view of a variable spatial filter formed of a photochromic material.
Figure 38:
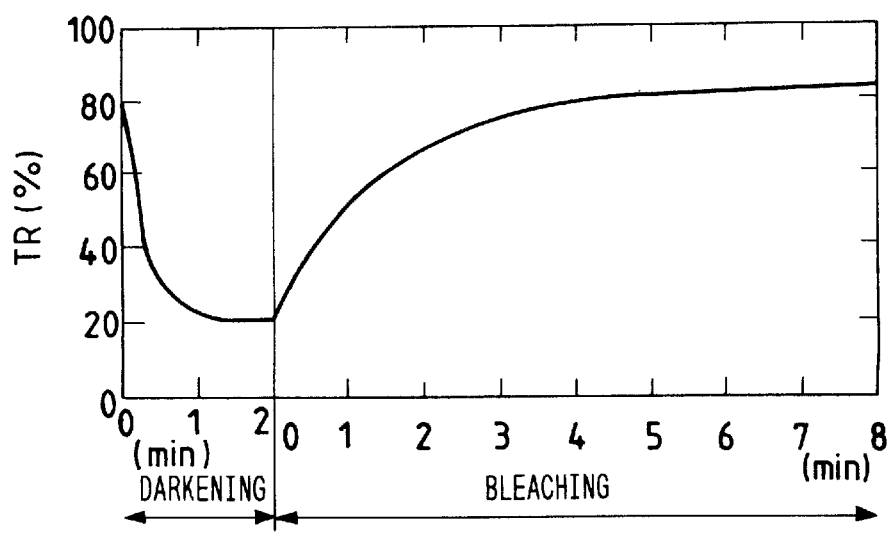
FIG. 38 is a graph for assistance in explaining the characteristics of a photochromic material.

The variable spatial filter 44 (444) shown in FIG. 37 is a spatial light modulator which does not need developing. This spatial light modulator employs a photochromic glass plate 2301 fabricated by doping a glass plate with silver salt. The transmittance of the photochromic glass plate 2301 can be reversibly changed by irradiating the same with light. The photochromic glass plate 2301 has a substantially permanent life. As shown in FIG. 38, the transmittance TR (%) of the photochromic glass plate 2301 decreases by 20% (darkening) in about one minute when the photochromic glass plate 2301 is irradiated with illuminating light having a wavelength of, for example, 488 nm, and the same is restored to its original transmittance (bleaching) in about five to ten minutes after the illuminating light has been removed. The bleaching of the photochromic glass plate 2301 is promoted when the same is heated. These characteristics are used for detecting foreign particles.

(1) A periodic circuit pattern formed in a reticle is placed in the inspection field.

(2) The periodic circuit pattern is illuminated with illuminating light for about one minute to expose the photochromic glass plate 2301 to a Fourier transform image of the periodic circuit pattern, so that portions of the photochromic glass plate 2301 corresponding to the periodic circuit pattern darkens.

(3) The reticle is scanned for inspection, in which scattered light scattered by foreign particles travels through transparent portions of the photochromic glass plate 2301. Since the photochromic glass plate 2301 is irradiated instantaneously with the light scattered by foreign particles, portions irradiated with the same scattered light do not darken and do not affect the detection of the next foreign particle. Since light diffracted by the periodic circuit pattern, which occupies most part of the surface of the reticle, falls continuously on the photochromic glass plate 2301 during most of the time for inspection, the dark Fourier transform image of the periodic circuit pattern is maintained on the photochromic glass plate 2301.

(4) The photochromic glass plate 2301 is heated by a heating unit 2302 after the completion of inspection to bleach the photochromic glass plate 2301 to prepare the photochromic glass plate 2301 for the next inspection.

Although the photochromic glass plate 2301 in this example is heated by the heating unit 2302 to bleach the same quickly, the photochromic glass plate 2301 need not necessarily be heated. The heating unit 2302 may be omitted when a plurality of photochromic glass plates 2301, for example, two photochromic glass plates 2301, disposed on the same plane and a moving mechanism 2303 for moving the photochromic glass plates 2301 are used. One of the two photochromic glass plates 2301 is positioned at its working position for inspection, the photochromic glass plate 2301 is moved away from the working position to a standby position after the completion of inspection of a reticle, and the other photochromic glass plate 2301 is positioned at the working position for the inspection of the next reticle. The Fourier transform image formed on the former photochromic glass plate disappears and the photochromic glass plate 2 bleaches naturally while the latter photochromic glass plate is used. The use of the photochromic glass plate as the spatial filter 44 (444) eliminates troublesome photographic processes for fabricating a photographic spatial filter. An image of a linear spatial filter may be formed on the variable spatial filter by multiple exposure to omit the linear spatial filters 44 and 444.

Figure 39:
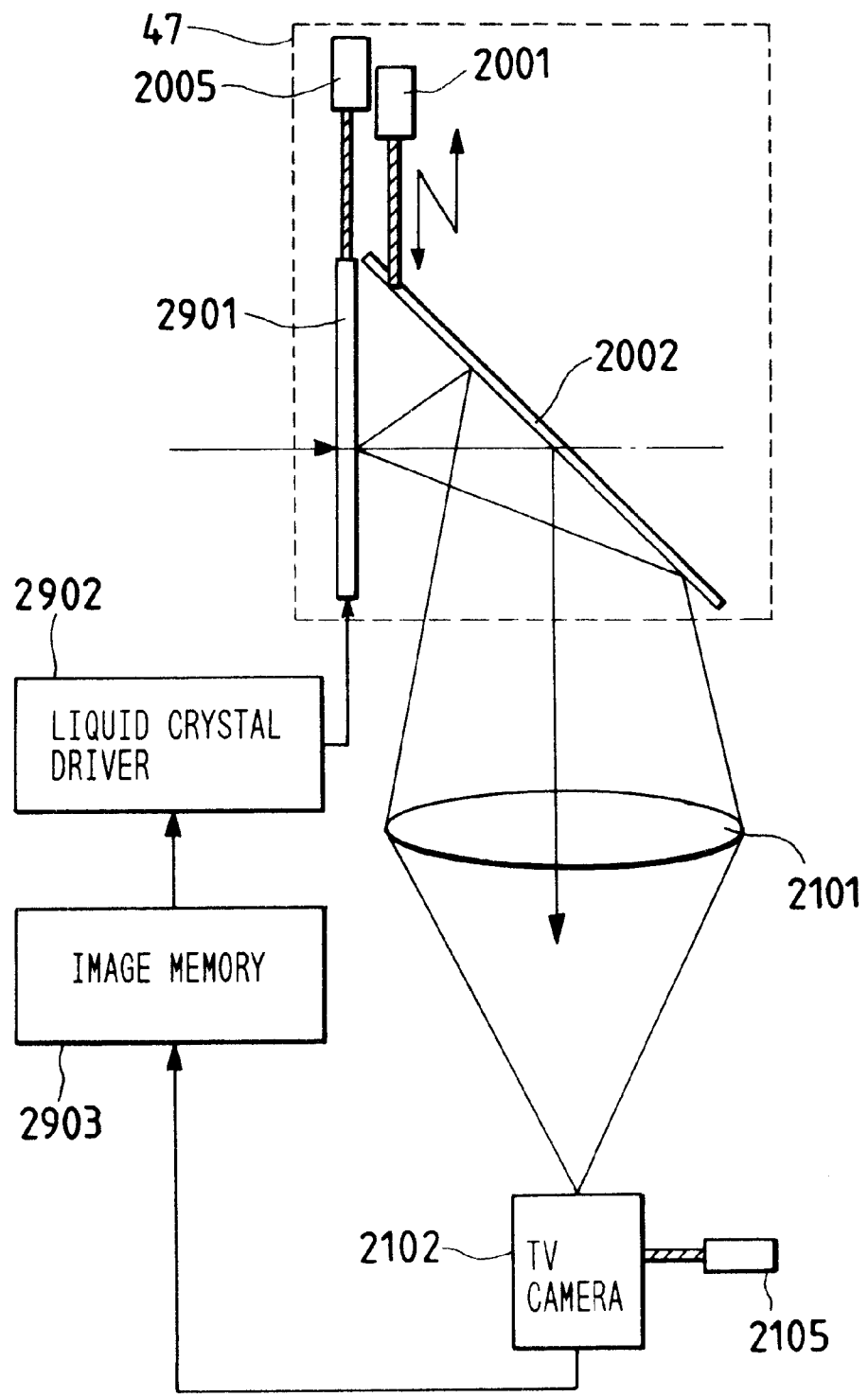
FIG. 39 is a diagrammatic view of a liquid crystal spatial optical modulator device used as a variable spatial filter.

An electrical addressing spatial light modulator may be employed instead of the light addressing spatial light modulator. FIG. 39 shows a variable spatial filter 47 employing a liquid crystal spatial light modulator 2901 as an electrical addressing spatial light modulator. The liquid crystal spatial light modulator 2901 is regarded as a matrix of (several hundred minute shutters)×(several hundred minute shutters). Since the liquid crystal spatial light modulator 2901 uses the double refraction characteristics of the liquid crystal, attention must be paid to the relation between the plane of polarization of the illuminating light and that of light to be intercepted by the liquid crystal.

The shutters of the liquid crystal spatial light modulator 2901 are controlled by an external liquid crystal driver 2902 with electric signals. The liquid crystal spatial light modulator itself does not have either a light detecting function or a signal storage function. Accordingly, as shown in FIG. 39, a mirror 2002 is positioned behind the liquid crystal spatial light modulator 2001 for recording by a mirror moving mechanism 2001 to deflect the light transmitted through the liquid crystal spatial light modulator 2901, an image of the liquid crystal spatial light modulator 2901 is formed on a TV camera 2102 or the like by an image forming lens 2101 to detect a Fourier transform image to be recorded by the image by the TV camera 2102, the detected Fourier transform image is stored temporarily in an image memory 2903, and then the Fourier transform image is given to the liquid crystal driver 2902. A half mirror may be used instead of the mirror 2002. The configuration shown in FIG. 39 enables the confirmation of the positioning of the reticle by means of the TV camera 2102.

Figure 40:
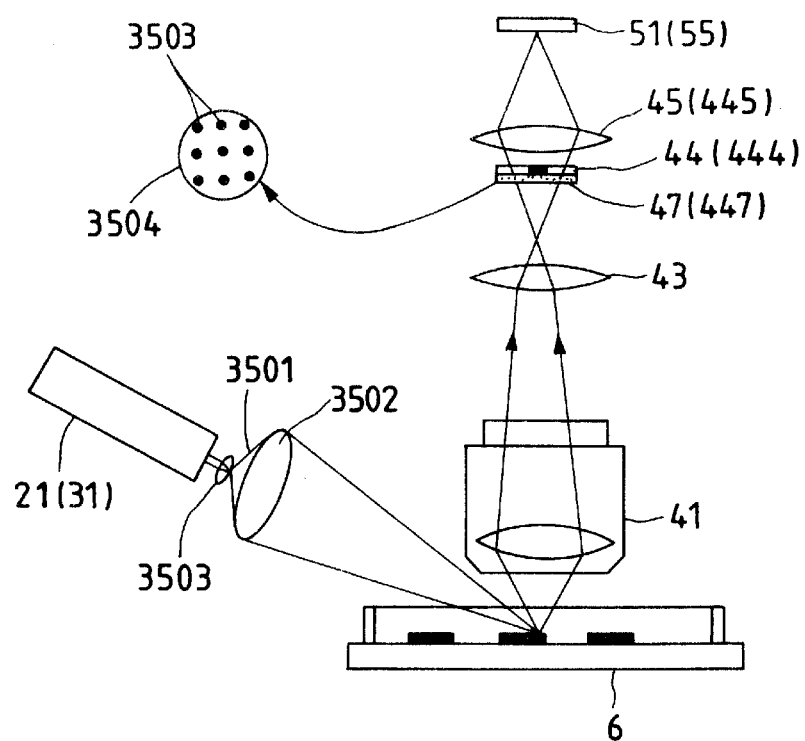
FIG. 40 is a diagrammatic view for assistance in explaining the size of luminescent spots in a Fourier transform image of a periodic pattern under high NA illumination.
Figure 41:
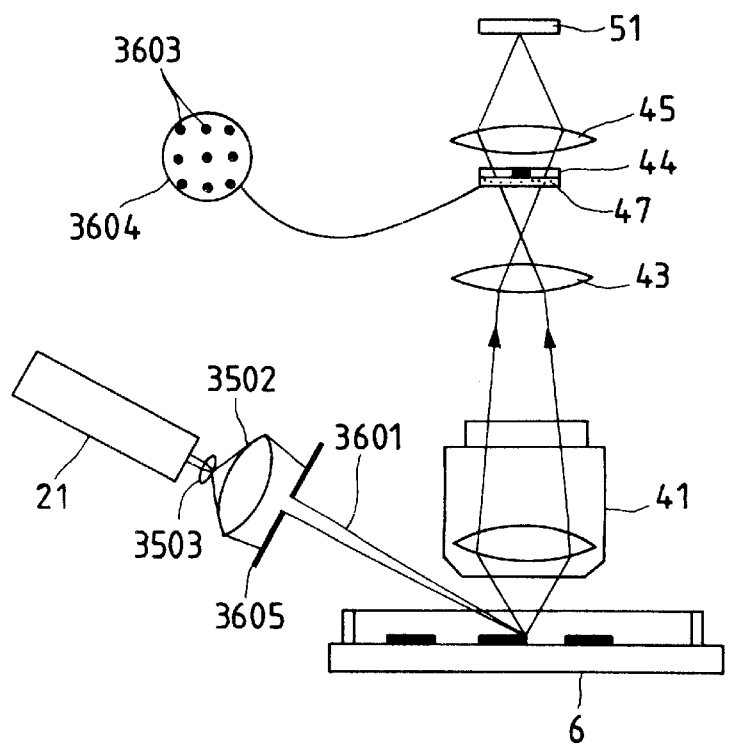
FIG. 41 is a diagrammatic view for assistance in explaining the size of luminescent spots in a Fourier transform image of a periodic pattern under low NA illumination.

Incidentally, when a periodic circuit pattern is illuminated with a convergent light beam, the Fourier transform image of the periodic circuit pattern is formed by discrete bright spots. The size of the bright spots is large when the convergent light beam has a large N.A. (Numerical Aperture) and is small when the convergent light beam has a small N.A. (Numerical Aperture). If the focal length of a condenser lens is fixed, a light beam 3501 having a large diameter formed by a beam expander or the like is gathered by a condenser lens 3502 in a convergent light beam to use the convergent light beam as an illuminating light beam, as shown in FIG. 40. A Fourier transform image 3504 of the periodic circuit pattern consists of discrete, large bright spots 3503, as illustrated in an enlarged view in FIG. 40. On the other hand, if a light beam 3601 having a small diameter is formed by a lens system 3503 or by an aperture plate 3605 having a small aperture and the light beam is us ed as an illuminating light beam, a Fourier transform image 3604 of the periodic circuit pattern consists of discrete, small bright spots 3603. This phenomenon is dependent on the NA of the condensing optical system and the size of the bright spots can be adjusted by fixing the diameter of the light beam and varying the focal length of the lens or by varying both the diameter of the light beam and the focal length of the lens. The size of the bright spots is thus adjusted to form the Fourier transform image with comparatively large bright spots for recording the Fourier transform image on the spatial filter and to form the Fourier transform image with comparatively small bright spots for inspection. The difference between there respective sizes of the comparatively large bright spots and the comparatively small bright spots is a margin of accuracy in positioning the spatial filter.

FIGS. 42(A) to 42(I) illustrate various reticles with a phase shifter which can be inspected by the reticle inspecting apparatus of the present invention.

As is apparent from the foregoing description, according to the present invention, a reticle inspecting apparatus comprises a detection optical system which illuminates the front surface of a reticle obliquely with a light beam having a wavelength around 780 nm, illuminates the back surface of the reticle obliquely with a light beam having a wavelength around 488 nm, gathers scattered light, separates the gathered light by direction of illumination and wavelength by an optical system having a NA of 0.4 or above and disposed on the side of the front surface of the reticle, shades diffracted light diffracted by a circuit pattern formed on the front surface of the reticle with a spatial filter disposed on a Fourier transform plane and forms an image on a detector, a circuit which corrects detection signals provided by the detector according to the irregularity of illumination, a circuit which adds detection signals provided by 2×2 $\mu m^2$ pixels, and a circuit which selects the maximum from among four sums obtained by shifting the detector in four directions by a distance corresponding to one pixel. The reticle inspecting apparatus thus constructed is capable of easily and stably detecting defects, such as foreign particles having sizes on the submicron order and adhering to a substrate provided with a circuit pattern, such as a photomask, particularly, a reticle provided with a phase shift film for improving printing resolution, and of discriminating the defects from the circuit pattern by means of simple, optical systems.

What is claimed is:

1. An inspecting apparatus for inspecting a specimen having, at least a transparent or translucent substrate, a circuit pattern formed on the front surface of the substrate, and for detecting defects, such as foreign particles adhering to the front surface of the specimen, said inspecting apparatus comprising:

an inspection stage unit having a stage for supporting the specimen thereon for movement in directions along at least an X-axis and a Y-axis, and a stage driving system for driving the stage for movement;

an illuminating system which illuminates the substrate provided with the circuit pattern in a front illumination mode with light of a first wavelength and in a back illumination mode with light of a second wavelength, wherein the first wavelength is greater than the second wavelength and greater than the size of a smallest defect to be detected among the defects to be detected;

a detection optical system gathering scattered light and diffracted light which have been scattered and diffracted, respectively, by the specimen, separating the gathered light by direction of illumination, and forming images of gathered light on detectors; and a signal processing system having a signal processing unit which processes data concerning defects on the specimen on the basis of output signals of the detectors and displays information of the processed data concerning defects.

2. An inspecting apparatus according to claim 1, wherein the first wavelength is between 600 nm and 800 nm and the second wavelength is between 450 nm and 550 nm.

3. An inspecting apparatus according to claim 1, wherein the first wavelength is 780 nm and the second wavelength is 488 nm.

4. An inspecting apparatus according to claim 1, wherein the size of the smallest defect to be detected is represented by d and the second wavelength is represented by about 1.0 d and the first wavelength is represented by about 1.6 d.

5. An inspecting Apparatus according to claim 4, wherein the second wavelength is about 450 nm to about 550 nm and the first wavelength is about 600 nm to about 800 nm.

6. A reticle inspecting apparatus according to claim 5, wherein the second wavelength of the light in the first predetermined range is 488 nm and the first wavelength of the light in the second predetermined range is 780 nm.

7. A reticle inspecting apparatus for inspecting a reticle having, at least a transparent or translucent substrate, a circuit pattern formed on the front surface of the substrate and a phase shifter formed of a light-transmissive film on the front surface of the substrate, for defects, such as foreign particles adhering to the front surface of the reticle, said reticle inspecting apparatus comprising:

an inspection stage unit having a stage for supporting the reticle thereon for movement in directions along an X-axis, a Y-axis and a Z-axis, and a stage driving system for driving the stage for movement;

an illuminating system for the reflected illumination of the front surface of the substrate provided with the circuit pattern with an illuminating light beam having a wavelength of 1.6 d, where d is the size of the smallest defects among those to be detected, and for the transmitted illumination of the front surface of the substrate provided with the circuit pattern with an illuminating light beam having a wavelength of 1.0 d;

a detection optical system disposed so as not to gather directly reflected light and directly transmitted light and so as to gather scattered light and diffracted light which has been scattered and diffracted, respectively, by the reticle, said detection optical system being capable of separating the gathered light by direction of illumination, and being provided with detectors and spatial filters, disposed respectively on Fourier transform planes to intercept light diffracted by straight edges of the circuit pattern, for forming images of the gathered light on the detectors; and a signal processing system having a signal processing unit which calculates data concerning defects in the reticle on the basis of output signals of the detectors and displays the calculated data.

8. An inspecting apparatus for inspecting a specimen having, at least a transparent or translucent substrate, a circuit pattern formed on the front surface of the substrate, and for detecting defects, such as foreign particles adhering to light-transmissive portions of the substrate, said inspecting apparatus comprising:

an illuminating system for illuminating the specimen with an illuminating light beam in a back illumination mode having a first wavelength of about the same as the size of a smallest defect among the defects to be detected, for transmitted illumination, and with an illuminating light beam in a front illumination mode having a second wavelength greater than the first wavelength and greater than the size of the smallest defect among the defects to be detected; and a detection optical system disposed so as not to gather directly transmitted light and so as to gather scattered light and diffracted light which have been scattered and diffracted, respectively, by the specimen, and being provided with detectors that receive gathered light.

9. An inspecting apparatus according to claim 8, wherein the first wavelength is between 450 nm and 550 nm and the second wavelength is between 600 nm and 800 nm.

10. An inspecting apparatus according to claim 8, wherein the size of the smallest defect to be detected is represented by d, the first wavelength is represented by about 1.0 d and the second wavelength is represented by about 1.6 d.

11. An inspecting apparatus according to claim 10, wherein the first wavelength is between 450 nm and 550 nm and the second wavelength is between 600 nm and 800 nm.

12. A method of inspecting a specimen having, at least a transparent or translucent substrate, a circuit pattern formed on the front surface of the substrate, and a phase shifter formed of a light-transmissive film on the front surface of the substrate, and detecting defects, such as foreign particles adhering to the front surface of the specimen, said method comprising the steps of:

moving an inspection stage fixedly supporting the reticle thereon in directions along at least an X-axis and a Y-axis;

illuminating the substrate provided with the circuit pattern in a front illumination mode with light of a first wavelength and in a back illumination mode with light of a second wavelength, wherein the first wavelength is greater than the second wavelength and greater than the size of a smallest defect to be detected among the defects to be detected;

gathering scattered light and diffracted light which have been scattered and diffracted, respectively, by the specimen and separating the gathered light by direction of illumination by a detection optical system;

forming images of the gathered light on detectors included in the detection optical system;

processing data concerning defects on the basis of output signals of the detectors; and displaying information of the processed data concerning defects.

13. A method of inspecting a specimen according to claim 12, wherein the first wavelength is between 600 nm and 800 nm and the second wavelength is between 450 nm and 550 nm.

14. A method of inspecting a specimen according to claim 12, wherein the size of the smallest defect to be detected is represented by d and the second wavelength predetermined range is represented by about 1.0 d and the first wavelength of the light in the second predetermined range is represented by about 1.6 d.

15. A method of inspecting a specimen according to claim 14, wherein the second wavelength is about 450 nm to about 550 nm and the first wavelength is about 600 nm to about 800 nm.

16. A method of inspecting a specimen according to claim 15, wherein the second wavelength of the light is 488 nm and the first wavelength of the light is 780 nm.

17. A method of inspecting a reticle having, at least a transparent or translucent substrate, a circuit pattern formed on the front surface of the substrate, and a phase shifter formed of a light-transmissive film on the front surface of the substrate, for defects, such as foreign particles adhering to the front surface of the reticle, said method comprising the steps of:

optionally moving an inspection stage fixedly supporting the reticle thereon in directions along an X-axis, a Y-axis and a Z-axis;

illuminating the front surface of the reticle with an illuminating light beam having a wavelength of about 1.6 d, where d is the size of the smallest defects among those to be detected, for reflected illumination and with an illuminating light beam having a wavelength of about 1.0 d for transmitted illumination by an illuminating system;

gathering scattered light and diffracted light which have been scattered and diffracted, respectively, by the reticle and separating the gathered light by direction of illumination by a detection optical system;

intercepting light diffracted by straight edges of the circuit pattern with spatial filters included in the detection optical system and disposed respectively on Fourier transform planes;

forming images of the gathered light on detectors included in the detection optical system;

calculating data concerning defects on the basis of output signals of the detectors; and displaying the calculated data.

18. A method of inspecting a specimen having, at least a transparent or translucent substrate, a circuit pattern formed on the front surface of the substrate, and detecting defects, such as foreign particles adhering to the front surface of the specimen, said method comprising the steps of:

illuminating the specimen with an illuminating light beam in a back illumination mode having a wavelength of about the same as a size of the smallest defect among the defects to be detected, for transmitted illumination, and with an illuminating light beam in a front illumination mode having a wavelength greater than the wavelength in the back illumination mode and greater than the size of the smallest defect among the defects to be detected;

gathering scattered light and diffracted light which have been scattered and diffracted, respectively, by the specimen on detectors by a detection optical systems;

processing data concerning defects on the basis of output signals of the detectors; and displaying the processed data.

19. A method of inspecting a specimen according to claim 18, wherein the size of the smallest defect to be detected is represented by d and the second wavelength is represented by about 1.0 d and the first wavelength is represented by about 1.6 d.

20. A method of inspecting a reticle according to claim 19, wherein the second wavelength of the light in the first predetermined range is about 450 nm to about 550 nm.

21. A method of inspecting a reticle according to claim 20, wherein the second wavelength is 488 nm.

22. A method of inspecting a specimen according to claim 18, wherein the first wavelength is between 600 nm and 800 nm and the second wavelength is between 450 nm and 550 nm.

* * * * *